US010377809B2

(12) United States Patent
Bulik et al.

(10) Patent No.: US 10,377,809 B2
(45) Date of Patent: *Aug. 13, 2019

(54) MODIFIED GLYCOPROTEINS

(71) Applicant: Momenta Pharmaceuticals, Inc., Cambridge, MA (US)

(72) Inventors: Dorota A. Bulik, Malden, MA (US); Carlos J. Bosques, Arlington, MA (US); Brian Edward Collins, Arlington, MA (US); Maurice Gaston Hains, Brockton, MA (US); Nathaniel J. Washburn, Littleton, MA (US); James Meador, Framingham, MA (US); Sean Smith, Littleton, MA (US); Naveen Bhatnagar, Framingham, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 80 days.

This patent is subject to a terminal disclaimer.

(21) Appl. No.: 15/483,545

(22) Filed: Apr. 10, 2017

(65) Prior Publication Data

US 2017/0247426 A1 Aug. 31, 2017

Related U.S. Application Data

(63) Continuation of application No. 14/118,269, filed as application No. PCT/US2012/038628 on May 18, 2012, now Pat. No. 9,650,433.

(60) Provisional application No. 61/638,134, filed on Apr. 25, 2012, provisional application No. 61/488,523, filed on May 20, 2011.

(51) Int. Cl.
*C07K 14/70* (2006.01)
*C07K 14/705* (2006.01)
*C07K 16/00* (2006.01)

(52) U.S. Cl.
CPC ........ *C07K 14/70521* (2013.01); *C07K 16/00* (2013.01); *C07K 2317/41* (2013.01); *C07K 2319/30* (2013.01); *C07K 2319/40* (2013.01); *C07K 2319/74* (2013.01); *C07K 2319/91* (2013.01)

(58) Field of Classification Search
None
See application file for complete search history.

(56) References Cited

U.S. PATENT DOCUMENTS

| 5,047,335 | A | 9/1991 | Paulson et al. |
| 5,278,299 | A | 1/1994 | Wong et al. |
| 5,510,261 | A | 4/1996 | Goochee et al. |
| 6,194,551 | B1 | 2/2001 | Idusogie et al. |
| 9,650,433 | B2 | 5/2017 | Bulik et al. |

| 2006/0088906 | A1 | 4/2006 | DeFrees et al. |
| 2008/0260738 | A1 | 10/2008 | Moore et al. |
| 2009/0288178 | A1 | 11/2009 | Jarvis |

FOREIGN PATENT DOCUMENTS

| WO | WO-99/51642 A1 | 10/1999 |
| WO | WO-2008/057634 A2 | 5/2008 |
| WO | WO-2009/132130 A2 | 10/2009 |
| WO | WO-2010/071824 A2 | 6/2010 |

OTHER PUBLICATIONS

Anthony, R. et al., Recapitulation of IVIG anti-inflammatory activity with a recombinant IgG Fc, Science, 320(5874):373-376 (2008).
Arnold, J. et al., Human serum IgM glycosylation: identification of glycoforms that can bind to mannan-binding lectin, Journal of Biological Chemistry, 280(32):29080-29087 (2005).
Beck, A. et al., Trends in glycosylation, glycoanalysis and glycoengineering of therapeutic antibodies and Fc-fusion proteins, Current Pharmaceutical Biotechnology, 9(6):482-501 (2008).
Bowman, K. and Bertozzi, C., Carbohydrate sulfotransferases: mediators of extracellular communication, Chemistry and Biology, 6(1):R9-R22 (1999).
Cassel, D. et al., Differential expression of Fc gamma RIIA, Fc gamma RIIB and Fc gamma RIIC in hematopoietic cells: analysis of transcripts, Molecular Immunology, 30(5):451-460 (1993).
Chen, Y. et al., Glycosite Analysis in Glycoproteomics by Mass Spectrometry, Current Proteomics, 7:158-167 (2010).
Dall'Acqua, W. et al., Increasing the Affinity of a Human IgG1 for the Neonatal Fc Receptor: Biological Consequences, The Journal of Immunology, 169:5171-5180 (2002).
Daëron, M., Fc receptor biology, Annual Review of Immunology, 15:203-234 (1997).
Duncan, A. et al., Localization of the binding site for the human high-affinity Fc receptor on IgG, Nature, 332(6164):563-564 (1988).
Falany, Charles N., Enzymology of human cytosolic sulfotransferases, The FASEB Journal, 11(4):206-216 (1997).
Ferrara, C. et al., Unique carbohydrate-carbohydrate interactions are required for high affinity binding between FcγRIII and antibodies lacking core fucose, Proceedings of the National Academy of Sciences, 108(31):12669-12674 (2011).
GenBank Accession No. NP_003645, CHST1 (2015).
GenBank Accession No. NP_004264, CHST3 (2015).
GenBank Accession No. NP_005760, CHST4 (2015).
GenBank Accession No. NP_063939, CHST7 (2015).
GenBank Accession No. NP_067628, CHST6 (2015).
GenBank Accession No. NP_078809, CHST5 (2015).
GenBank Accession No. Q9Y4C5, CHST2 (2015).
Gessner, J. et al., The IgG Fc receptor family, Annals of Hematology, 76(6):231-248 (1998).

(Continued)

*Primary Examiner* — Nelson B Moseley, II
(74) *Attorney, Agent, or Firm* — Choate Hall & Stewart LLP; Brenda Herschbach Jarrell; Rolando Medina

(57) ABSTRACT

Sulfated glycoproteins, and methods of making and using such sulfated glycoproteins, are described.

13 Claims, 13 Drawing Sheets
Specification includes a Sequence Listing.

(56) References Cited

OTHER PUBLICATIONS

Ghetie, V. and Ward, E., Multiple roles for the major histocompatibility complex class I-related receptor FcRn, Annual Review of Immunology, 18:739-66 (2000).

Girard, J. et al., Sulfation in high endothelial venules: cloning and expression of the human PAPS synthetase, The FASEB Journal, 12(7):603-612 (1998).

Grunwell, J. and Bertozzi, C., Carbohydrate sulfotransferases of the GalNAc/Gal/GlcNAc6ST family, Biochemistry, 41(44):13117-13126 (2002).

Hemmerich, S. and Rosen, S., Carbohydrate sulfotransferases in lymphocyte homing. Glycobiology, 10(9):849-856 (2000).

Huang, C. et al., Structural basis of tyrosine sulfation and VH-gene usage in antibodies that recognize the HIV type 1 coreceptor-binding site on gp120, Proceedings of the National Academy of Sciences USA, 101(9):2706-2711 (2004).

Idusogie, E. et al., Mapping of the C1q binding site on rituxan, a chimeric antibody with a human IgG1 Fc, Journal of Immunology, 164(8):4178-4184 (2000).

International Search Report for PCT/US2012/038628, dated Oct. 15, 2012 (5 pages).

Jefferis, R. et al., IgG-Fc-mediated effector functions: molecular definition of interaction sites for effector ligands and the role of glycosylation, Immunology Review, 163:59-76 (1998).

Jefferis, Roy, Glycosylation as a strategy to improve antibody-based therapeutics, Nature Reviews Drug Discovery, 8(3):226-234 (2009).

Kaneko, Y. et al., Anti-inflammatory activity of immunoglobulin G resulting from Fc sialylation, Science, 313(5787):670-673 (2006).

Klaassen, C. and Boles, J., Sulfation and sulfotransferases 5: the importance of 3'-phosphoadenosine 5'-phosphosulfate (PAPS) in the regulation of sulfation, The FASEB Journal, 11(6):404-418 (1997).

Kurogochi, M. et al., Sialic acid-focused quantitative mouse serum glycoproteomics by multiple reaction monitoring assay, Molecular & Cellular Proteomics, 9(11):2354-2368 (2010).

Lehrnbecher, T. et al., Variant genotypes of the low-affinity Fcgamma receptors in two control populations and a review of low-affinity Fcgamma receptor polymorphisms in control and disease populations, Blood, 94(12):4220-4232 (1999).

Li, H. et al., The isolation and characterization of cDNA encoding the mouse bifunctional ATP sulfurylase-adenosine 5'-phosphosulfate kinase, Journal of Biological Chemistry, 270(49):29453-29459 (1995).

Masuda, K. et al., Mutational deglycosylation of the Fc portion of immunoglobulin G causes 0-sulfation of tyrosine adjacently preceding the originally glycosylated site, FEBS Letters, 584(15):3474-3479 (2010).

Mattu, T. et al., the glycosylation and structure of human serum IgA1, Fab, and Fc regions and the role of N-glycosylation on Fc? receptor interactions, Journal of Biological Chemistry, 273(4):2260-2272 (1998).

Mizushima, T. et al., Structural basis for improved efficacy of therapeutic antibodies on defucosylation of their Fc glycans, Genes to Cells, 16:1071-1080 (2011).

Nettleton, M. and Kochan, J., Role of glycosylation sites in the IgE Fc molecule, International Archives of Allergy and Immunology, 107(1-3):328-329 (1995).

Nimmerjahn, F. and Ravetch, J., Fcgamma receptors: old friends and new family members, Immunity., 4(1):19-28 (2006).

Ravetch, J. and Bolland, S., IgG Fc receptors, Annual Review of Immunology, 19:275-290 (2001).

Ravetch, J. and Kinet, J., Fc receptors, Annual Review of Immunology, 9:457-492 (1991).

Reichert, Janice M., Monoclonal Antibodies as Innovative Therapeutics, Current Pharmaceutical Biotechnology, 9:423-430 (2008).

Rikke, B. and Roy, A., Structural relationships among members of the mammalian sulfotransferase gene family, Biochimica et Biophysica Acta, 1307(3):331-338 (1996).

Schroeder, H. and Cavacini, L., Structure and function of immunoglobulins, Journal of Allergy and Clinical Immunology, 125(2 Suppl 2):S41-52 (2010).

Seko, A. et al., Ectopic expression of a GlcNAc 6-O-sulfotransferase, GlcNAc6ST-2, in colonic mucinous adenocarcinoma, Glycobiology, 12(6):379-388 (2002).

Shields, R. et al., High resolution mapping of the binding site on human IgG1 for Fc gamma RI, Fc gamma RII, Fc gamma RIII, and FcRn and design of IgG1 variants with improved binding to the Fc gamma R, Journal of Biological Chemistry, 276(9):6591-6604 (2001).

Sibéril, S., et al., Molecular aspects of human FcgammaR interactions with IgG: functional and therapeutic consequences, Immunology Letters, 106(2):111-118 (2006).

Stadlmann, J. et al., Analysis of immunoglobulin glycosylation by LC-ESI-MS of glycopeptides and oligosaccharides, Proteomics, 8(14):2858-2871 (2008).

Supplementary European Search Report for EP12790362, 3 pages (dated Jun. 22, 2015).

Ward E. and Ghetie, V., The effector functions of immunoglobulins: implications for therapy, Therapeutic Immunology, 2(2):77-94 (1995).

Woof, J. et al., Localisation of the monocyte-binding region on human immunoglobulin G, Molecular Immunology, 23(3):319-330 (1986).

Wright, A. and Morrison, S., Effect of glycosylation on antibody function: implications for genetic engineering, Trends in Biotechnology, 15(1):26-32 (1997).

Written Opinion for PCT/US2012/038628, dated Oct. 15, 2012 (14 pages).

Xue, J. et al., IgG-Fc N-glycosylation at Asn297 and IgA O-glycosylation in the hinge region in health and disease, Glycoconjugate Journal, 30:735-745 (2013).

SEQUENCE LISTING

<160> NUMBER OF SEQ ID NOS: 5

<210> SEQ ID NO 1
<211> LENGTH: 470
<212> TYPE: PRT
<213> ORGANISM: Artificial Sequence
<220> FEATURE:
<223> OTHER INFORMATION: WT rituximab

<400> SEQUENCE: 1

```
Met Gly Trp Ser Leu Ile Leu Leu Phe Leu Val Ala Val Ala Thr Arg
1               5                   10                  15

Val Leu Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80
```

```
Gln Lys Phe Lys Gly Lys Ala Thr Leu Thr Ala Asp Lys Ser Ser Ser
                85                  90                  95
Thr Ala Tyr Met Gln Leu Ser Ser Leu Thr Ser Glu Asp Ser Ala Val
            100                 105                 110
Tyr Tyr Cys Ala Arg Ser Thr Tyr Tyr Gly Gly Asp Trp Tyr Phe Asn
        115                 120                 125
Val Trp Gly Ala Gly Thr Thr Val Thr Val Ser Ala Ala Ser Thr Lys
130                 135                 140
Gly Pro Ser Val Phe Pro Leu Ala Pro Ser Ser Lys Ser Thr Ser Gly
145                 150                 155                 160
Gly Thr Ala Ala Leu Gly Cys Leu Val Lys Asp Tyr Phe Pro Glu Pro
                165                 170                 175
Val Thr Val Ser Trp Asn Ser Gly Ala Leu Thr Ser Gly Val His Thr
            180                 185                 190
Phe Pro Ala Val Leu Gln Ser Ser Gly Leu Tyr Ser Leu Ser Ser Val
        195                 200                 205
Val Thr Val Pro Ser Ser Ser Leu Gly Thr Gln Thr Tyr Ile Cys Asn
210                 215                 220
Val Asn His Lys Pro Ser Asn Thr Lys Val Asp Lys Lys Ala Glu Pro
225                 230                 235                 240
Lys Ser Cys Asp Lys Thr His Thr Cys Pro Pro Cys Pro Ala Pro Glu
                245                 250                 255
Leu Leu Gly Gly Pro Ser Val Phe Leu Phe Pro Pro Lys Pro Lys Asp
            260                 265                 270
Thr Leu Met Ile Ser Arg Thr Pro Glu Val Thr Cys Val Val Val Asp
        275                 280                 285
Val Ser His Glu Asp Pro Glu Val Lys Phe Asn Trp Tyr Val Asp Gly
290                 295                 300
Val Glu Val His Asn Ala Lys Thr Lys Pro Arg Glu Glu Gln Tyr Asn
305                 310                 315                 320
Ser Thr Tyr Arg Val Val Ser Val Leu Thr Val Leu His Gln Asp Trp
                325                 330                 335
Leu Asn Gly Lys Glu Tyr Lys Cys Lys Val Ser Asn Lys Ala Leu Pro
            340                 345                 350
Ala Pro Ile Glu Lys Thr Ile Ser Lys Ala Lys Gly Gln Pro Arg Glu
        355                 360                 365
Pro Gln Val Tyr Thr Leu Pro Pro Ser Arg Asp Glu Leu Thr Lys Asn
370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                405                 410                 415
Thr Pro Pro Val Leu Asp Ser Asp Gly Ser Phe Phe Leu Tyr Ser Lys
            420                 425                 430
Leu Thr Val Asp Lys Ser Arg Trp Gln Gln Gly Asn Val Phe Ser Cys
        435                 440                 445
Ser Val Met His Glu Ala Leu His Asn His Tyr Thr Gln Lys Ser Leu
450                 455                 460
Ser Leu Ser Pro Gly Lys
465                 470

<210> SEQ ID NO 2
<211> LENGTH: 470
<212> TYPE: PRT
```

<213> ORGANISM: Artificial Sequence
<220> FEATURE:
<223> OTHER INFORMATION: Mutant 1- F241A, F243A

<400> SEQUENCE: 2

```
Met Gly Trp Ser Leu Ile Leu Leu Phe Leu Val Ala Val Ala Thr Arg
1               5                   10                  15

Val Leu Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
        115                 120                 125

Val Trp Gly Ala Gly Thr Thr Val Thr Val Ser Ala Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Ala Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Ala Leu Ala Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
```

```
385                 390                 395                 400
Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
    450                 455                 460

Ser Leu Ser Pro Gly Lys
465             470

<210> SEQ ID NO 3
<211> LENGTH: 470
<212> TYPE: PRT
<213> ORGANISM: Artificial Sequence
<220> FEATURE:
<223> OTHER INFORMATION: Mutant 2- F243A, R301A

<400> SEQUENCE: 3

Met Gly Trp Ser Leu Ile Leu Leu Phe Leu Val Ala Val Ala Thr Arg
1               5                   10                  15

Val Leu Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
        115                 120                 125

Val Trp Gly Ala Gly Thr Thr Val Thr Val Ser Ala Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Ala Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Ala Pro Pro Lys Pro Lys Asp
            260                 265                 270

Thr Leu Met Ile Ser Arg Thr Pro Glu Val Thr Cys Val Val Val Asp
```

```
                 275                 280                 285
Val Ser His Glu Asp Pro Glu Val Lys Phe Asn Trp Tyr Val Asp Gly
            290                 295                 300
Val Glu Val His Asn Ala Lys Thr Lys Pro Arg Glu Glu Gln Tyr Asn
305                 310                 315                 320
Ser Thr Tyr Arg Val Val Ser Val Leu Thr Val Leu His Gln Asp Trp
                325                 330                 335
Leu Asn Gly Lys Glu Tyr Lys Cys Lys Val Ser Asn Lys Ala Leu Pro
            340                 345                 350
Ala Pro Ile Glu Lys Thr Ile Ser Lys Ala Lys Gly Gln Pro Arg Glu
        355                 360                 365
Pro Gln Val Tyr Thr Leu Pro Pro Ser Arg Asp Glu Leu Thr Lys Asn
    370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                405                 410                 415
Thr Pro Pro Val Leu Asp Ser Asp Gly Ser Phe Phe Leu Tyr Ser Lys
            420                 425                 430
Leu Thr Val Asp Lys Ser Arg Trp Gln Gln Gly Asn Val Phe Ser Cys
        435                 440                 445
Ser Val Met His Glu Ala Leu His Asn His Tyr Thr Gln Lys Ser Leu
    450                 455                 460
Ser Leu Ser Pro Gly Lys
465                 470

<210> SEQ ID NO 4
<211> LENGTH: 470
<212> TYPE: PRT
<213> ORGANISM: Artificial Sequence
<220> FEATURE:
<223> OTHER INFORMATION: Mutant 3- K246A, T260A

<400> SEQUENCE: 4

Met Gly Trp Ser Leu Ile Leu Leu Phe Leu Val Ala Val Ala Thr Arg
1               5                   10                  15
Val Leu Ser Gln Val Gln Leu Gln Gln Pro Gly Ala Glu Leu Val Lys
            20                  25                  30
Pro Gly Ala Ser Val Lys Met Ser Cys Lys Ala Ser Gly Tyr Thr Phe
        35                  40                  45
Thr Ser Tyr Asn Met His Trp Val Lys Gln Thr Pro Gly Arg Gly Leu
    50                  55                  60
Glu Trp Ile Gly Ala Ile Tyr Pro Gly Asn Gly Asp Thr Ser Tyr Asn
65                  70                  75                  80
Gln Lys Phe Lys Gly Lys Ala Thr Leu Thr Ala Asp Lys Ser Ser Ser
                85                  90                  95
Thr Ala Tyr Met Gln Leu Ser Ser Leu Thr Ser Glu Asp Ser Ala Val
            100                 105                 110
Tyr Tyr Cys Ala Arg Ser Thr Tyr Tyr Gly Gly Asp Trp Tyr Phe Asn
        115                 120                 125
Val Trp Gly Ala Gly Thr Thr Val Thr Val Ser Ala Ala Ser Thr Lys
    130                 135                 140
Gly Pro Ser Val Phe Pro Leu Ala Pro Ser Ser Lys Ser Thr Ser Gly
145                 150                 155                 160
Gly Thr Ala Ala Leu Gly Cys Leu Val Lys Asp Tyr Phe Pro Glu Pro
```

```
                    165                 170                 175
Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
        210                 215                 220

Val Asn His Lys Pro Ser Asn Thr Lys Val Asp Lys Lys Ala Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Ala Pro Lys Asp
            260                 265                 270

Thr Leu Met Ile Ser Arg Thr Pro Glu Val Ala Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 5
<211> LENGTH: 470
<212> TYPE: PRT
<213> ORGANISM: Artificial Sequence
<220> FEATURE:
<223> OTHER INFORMATION: Mutant 4- T260A, R301A

<400> SEQUENCE: 5

Met Gly Trp Ser Leu Ile Leu Leu Phe Leu Val Ala Val Ala Thr Arg
1               5                   10                  15

Val Leu Ser Gln Val Gln Leu Gln Gln Pro Gly Ala Glu Leu Val Lys
                20                  25                  30

Pro Gly Ala Ser Val Lys Met Ser Cys Lys Ala Ser Gly Tyr Thr Phe
            35                  40                  45

Thr Ser Tyr Asn Met His Trp Val Lys Gln Thr Pro Gly Arg Gly Leu
```

```
            50                  55                  60
Glu Trp Ile Gly Ala Ile Tyr Pro Gly Asn Gly Asp Thr Ser Tyr Asn
 65                  70                  75                  80

Gln Lys Phe Lys Gly Lys Ala Thr Leu Thr Ala Asp Lys Ser Ser Ser
                 85                  90                  95

Thr Ala Tyr Met Gln Leu Ser Ser Leu Thr Ser Glu Asp Ser Ala Val
                100                 105                 110

Tyr Tyr Cys Ala Arg Ser Thr Tyr Gly Gly Asp Trp Tyr Phe Asn
                115                 120                 125

Val Trp Gly Ala Gly Thr Thr Val Thr Val Ser Ala Ala Ser Thr Lys
                130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
                195                 200                 205

Val Thr Val Pro Ser Ser Leu Gly Thr Gln Thr Tyr Ile Cys Asn
                210                 215                 220

Val Asn His Lys Pro Ser Asn Thr Lys Val Asp Lys Lys Ala Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Ala Cys Val Val Val Asp
                275                 280                 285

Val Ser His Glu Asp Pro Glu Val Lys Phe Asn Trp Tyr Val Asp Gly
                290                 295                 300

Val Glu Val His Asn Ala Lys Thr Lys Pro Arg Glu Glu Gln Tyr Asn
305                 310                 315                 320

Ser Thr Tyr Ala Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
                355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445
```

```
Ser Val Met His Glu Ala Leu His Asn His Tyr Thr Gln Lys Ser Leu
    450                 455                 460
Ser Leu Ser Pro Gly Lys
465                 470
```

MODIFIED GLYCOPROTEINS

CROSS REFERENCE TO RELATED APPLICATIONS

This application is a continuation of U.S. application Ser. No. 14/118,269, filed Dec. 30, 2013, which is the National Stage of International Application No. PCT/US2012/038628, filed May 18, 2012, which claims the benefit of U.S. Provisional Application No. 61/488,523, filed May 20, 2011, and of U.S. Provisional Application No. 61/638,134, filed Apr. 25, 2012, the contents of all of which are hereby incorporated by reference herein in their entireties.

REFERENCE TO SEQUENCE LISTING

The specification includes a Sequence Listing in the form of an ASCII compliant text file named "Sequence Listing.txt", which was created on Jun. 7, 2012 and has a size of 20.4 kilobytes. The content of the aforementioned "Sequence Listing.txt" file is hereby incorporated by reference in its entirety.

FIELD OF THE INVENTION

The invention relates generally to glycobiology and glycoproteins.

BACKGROUND

Therapeutic glycoproteins are an important class of therapeutic biotechnology products, and therapeutic antibodies (including murine, chimeric, humanized and human antibodies and fragments thereof) account for the majority of therapeutic biologic products.

SUMMARY

The invention is based, in part, on the discovery that sulfation of N-linked glycans of an antibody molecule can affect its activity and/or function. Accordingly, the invention features glycoproteins (e.g., antibodies or Fc-receptor fusion proteins) that include a sulfated CH2 domain of an immunoglobulin Fc region, as well as methods of making them, and methods of using them.

In one aspect, the invention features a glycoprotein comprising a sulfated immunoglobulin Fc region, or a sulfated Fc fragment thereof. In some embodiments, the sulfated Fc region or the sulfated Fc fragment comprises one or more N-glycosylation sites of an Fc region. In certain embodiments, the sulfated Fc region comprises one or more of a CH2 immunoglobulin domain, a CH3 immunoglobulin domain, and a CH4 immunoglobulin domain. In particular embodiments, the sulfated Fc region comprises a CH2 domain of an IgG heavy chain. In some embodiments, the sulfated Fc region comprises one or more N-glycosylation sites of an IgA, IgD, IgE, IgG, or IgM antibody heavy chain. In yet other embodiments, the Fc region comprises Asn297 of an IgG heavy chain.

In some embodiments, the glycoprotein is an isolated glycoprotein. In other embodiments, the glycoprotein is a purified glycoprotein. In other embodiments, the glycoprotein is a non-naturally occurring or a synthetic glycoprotein.

In certain embodiments, the glycoprotein comprises an Fc region or an Fc fragment comprising a sulfated glycan. In certain embodiments, the sulfated glycan is linked to one or more of a CH2 immunoglobulin domain, a CH3 immunoglobulin domain, and a CH4 immunoglobulin domain. In particular embodiments, the sulfated glycan is linked to a CH2 domain of an IgG heavy chain. In some embodiments, the sulfated glycan is linked to one or more N-glycosylation sites of an IgA, IgD, IgE, IgG, or IgM antibody heavy chain. In yet other embodiments, the sulfated glycan is linked to Asn297 of an IgG heavy chain.

In some embodiments, the sulfated glycan comprises a branched glycan. In certain embodiments, the sulfated glycan comprises one or more of a sulfated N-acetylglucosamine, a sulfated galactose, or a sulfated N-acetylgalactosamine.

In some embodiments, the glycoprotein is a modified glycoprotein comprising one or more amino acid substitutions of a reference glycoprotein. In some embodiments, the modified glycoprotein comprises a modified amino acid sequence of a reference glycoprotein and comprises a modified glycan, wherein the reference glycoprotein comprises an immunoglobulin Fc region, or Fc fragment, comprising a reference glycan, wherein the modified glycoprotein comprises one or more amino acid substitutions of the Fc region, or Fc fragment, of the reference glycoprotein. In some embodiments, the one or more amino acid substitutions result in increased sulfation of the modified glycan relative to the reference glycan.

In some embodiments, at least one of the amino acids substituted is F241, F243, K246, T260, or R301 of an IgG heavy chain. In some embodiments, at least one of the amino acid substitutions is F241A, F243A, K246A, T260A, or R301A.

In some embodiments, the modified glycoprotein comprises two or more amino acid substitutions of the Fc region, or Fc fragment, of the reference glycoprotein. In some embodiments, the two or more amino acid substitutions result in increased sulfation of the modified glycan relative to the reference glycan. In some embodiments, at least two of the amino acid substitutions are selected from F241A, F243A, K246A, T260A, and R301A. In particular embodiments, at least two of the amino acid substitutions are F241A and F243A; F241A and K246A; F241A and T260A; F241A and R301A; F243A and K246A; F243A and T260A; F243A and R301A; K246A and T260A; K246A and R301A; or T260A and R301A.

In some embodiments, the modified glycan has an altered glycan composition (e.g., an altered glycan composition described herein) relative to the reference glycan.

In some embodiments, the modified glycoprotein comprises a modified glycan that is sulfated at a higher level relative to the reference glycan.

In some embodiments, the glycoprotein is present in a population of glycoproteins, wherein at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 40%, at least about 50%, at least about 60%, at least about 70%, at least about 80%, at least about 90%, at least about 95%, or at least about 100% of the glycoproteins of the population comprise a sulfated Fc region or a sulfated Fc fragment.

In certain embodiments, the glycan is singly sulfated. In other embodiments, the glycan is doubly sulfated.

In some embodiments, the glycoprotein comprises two Fc regions, wherein one of the Fc regions is sulfated. In other embodiments, the glycoprotein comprises two Fc regions wherein both Fc regions are sulfated.

In other embodiments, the glycoprotein comprising a sulfated Fc region or sulfated Fc fragment, or the modified glycoprotein (e.g., comprising one or more amino acid substitutions) comprising a sulfated Fc region or sulfated Fc fragment, has a different, e.g., a detectably higher or lower, activity, such as an immune cell activating activity, e.g., Fc receptor affinity, Fc receptor specificity, complement activation activity, signaling activity, targeting activity, effector function, half-life, clearance, pro-inflammatory, anti-inflammatory, or transcytosis activity than a corresponding wild type or reference glycoprotein without a sulfated Fc region or sulfated Fc fragment. In some embodiments, the effector function is antibody dependent cellular cytotoxicity, complement dependent cytotoxicity, programmed cell death, or cellular phagocytosis.

In certain embodiments, the Fc receptor is an FcγRI, FcγRIIA, FcγRIIB, FcγRIIIA, FcγRIIIB, FcγRIV, or FcRn receptor. In some embodiments, the glycoprotein binds to an immune cell, e.g., a macrophage, neutrophil, dendritic cell, B cell, natural killer cell (NKC), or eosinophil.

In some embodiments, the glycoprotein comprising a sulfated Fc region or sulfated Fc fragment is an antibody comprising a sulfated Fc region or sulfated Fc fragment. In certain embodiments, the antibody is an IgA, IgD, IgE, IgG, or IgM antibody. In particular embodiments, the antibody is an IgG1, IgG2, or IgG3 antibody.

In certain embodiments, the antibody comprising a sulfated Fc region or sulfated Fc fragment is a sulfated version of abciximab, adalimumab, alemtuzumab, basiliximab, bevacizumab, cetuximab, certolizumab, daclizumab, eculizumab, efalizumab, gemtuzumab, ibritumomab, infliximab, muromonab, natalizumab, omalizumab, palivizumab, panitumumab, ranibizumab, rituximab, tositumomab, or trastuzumab, comprising a sulfated Fc region or sulfated Fc fragment.

In yet other embodiments, the glycoprotein comprising a sulfated Fc region or sulfated Fc fragment is conjugated to a heterologous moiety. In some embodiments, the heterologous moiety is a polypeptide, nucleic acid, or small molecule. In particular embodiments, the glycoprotein conjugated to a heterologous moiety is sulfated a sulfated version of alefacept, sulfated abatacept, sulfated etanercept, sulfated rilonacept, or sulfated denileukin diftitox, comprising a sulfated Fc region or sulfated Fc fragment.

In another aspect, the invention features a glycoprotein comprising an Fc region or an Fc fragment comprising a sulfated glycan. In some embodiments, the glycoprotein is an isolated glycoprotein. In other embodiments, the glycoprotein is a purified glycoprotein. In other embodiments, the glycoprotein is a non-naturally occurring or a synthetic glycoprotein.

In certain embodiments, the sulfated glycan is linked to one or more of a CH2 immunoglobulin domain, a CH3 immunoglobulin domain, and a CH4 immunoglobulin domain of the Fc region. In particular embodiments, the sulfated glycan is linked to a CH2 domain of an IgG heavy chain. In some embodiments, the sulfated glycan is linked to one or more N-glycosylation sites of an IgA, IgD, IgE, IgG, or IgM antibody heavy chain. In yet other embodiments, the sulfated glycan is linked to Asn297 of an IgG heavy chain.

In some embodiments, the sulfated glycan comprises a branched glycan. In certain embodiments, the sulfated glycan comprises one or more of a sulfated N-acetylglucosamine, a sulfated galactose, or a sulfated N-acetylgalactosamine.

In some embodiments, the glycoprotein is a modified glycoprotein comprising one or more amino acid substitutions of a reference glycoprotein. In some embodiments, the modified glycoprotein comprises a modified amino acid sequence of a reference glycoprotein and comprises a modified glycan, wherein the reference glycoprotein comprises an immunoglobulin Fc region, or Fc fragment, comprising a reference glycan, wherein the modified glycoprotein comprises one or more amino acid substitutions of the Fc region, or Fc fragment, of the reference glycoprotein. In some embodiments, the one or more amino acid substitutions result in increased sulfation of the modified glycan relative to the reference glycan.

In some embodiments, at least one of the amino acids substituted is F241, F243, K246, T260, or R301 of an IgG heavy chain. In some embodiments, at least one of the amino acid substitutions is F241A, F243A, K246A, T260A, or R301A.

In some embodiments, the modified glycoprotein comprises two or more amino acid substitutions of the Fc region, or Fc fragment, of the reference glycoprotein. In some embodiments, the two or more amino acid substitutions result in increased sulfation of the modified glycan relative to the reference glycan. In some embodiments, at least two of the amino acid substitutions are selected from F241A, F243A, K246A, T260A, and R301A. In particular embodiments, at least two of the amino acid substitutions are F241A and F243A; F241A and K246A; F241A and T260A; F241A and R301A; F243A and K246A; F243A and T260A; F243A and R301A; K246A and T260A; K246A and R301A; or T260A and R301A.

In some embodiments, the modified glycan has an altered glycan composition (e.g., an altered glycan composition described herein) relative to the reference glycan.

In some embodiments, the modified glycoprotein comprises a modified glycan that is sulfated at a higher level relative to the reference glycan.

In some embodiments, the glycoprotein is present in a population of glycoproteins, wherein at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 40%, at least about 50%, at least about 60%, at least about 70%, at least about 80%, at least about 90%, at least about 95%, or at least about 100% of the glycoproteins of the population comprise a sulfated glycan.

In certain embodiments, the glycan is singly sulfated. In other embodiments, the glycan is doubly sulfated.

In some embodiments, the glycoprotein comprises two Fc regions, wherein the sulfated glycan is linked to one of the Fc regions. In other embodiments, the glycoprotein comprises two Fc regions wherein sulfated glycans are linked to both Fc regions.

In other embodiments, the sulfated glycoprotein or sulfated modified glycoprotein (e.g., comprising one or more amino acid substitutions) has a different, e.g., a detectably higher or lower, activity, such as an immune cell activating activity, e.g., Fc receptor affinity, Fc receptor specificity, complement activation activity, signaling activity, targeting activity, effector function, half-life, clearance, pro-inflammatory, anti-inflammatory, or transcytosis activity than a corresponding wild type or reference glycoprotein without a sulfated glycan. In some embodiments, the effector function is antibody dependent cellular cytotoxicity, complement dependent cytotoxicity, programmed cell death, or cellular phagocytosis.

In certain embodiments, the Fc receptor is an FcγRI, FcγRIIA, FcγRIIB, FcγRIIIA, FcγRIIIB, FcγRIV, or FcRn receptor. In some embodiments, the glycoprotein binds to an immune cell, e.g., a macrophage, neutrophil, dendritic cell, B cell, natural killer cell (NKC), or eosinophil.

In some embodiments, the glycoprotein comprising a sulfated glycan is an antibody comprising a sulfated glycan. In certain embodiments, the antibody is an IgA, IgD, IgE, IgG, or IgM antibody. In particular embodiments, the antibody is an IgG1, IgG2, or IgG3 antibody.

In certain embodiments, the antibody comprising a sulfated glycan is a sulfated version of abciximab, adalimumab, alemtuzumab, basiliximab, bevacizumab, cetuximab, certolizumab, daclizumab, eculizumab, efalizumab, gemtuzumab, ibritumomab, infliximab, muromonab, natalizumab, omalizumab, palivizumab, panitumumab, ranibizumab, rituximab, tositumomab, or trastuzumab, comprising a sulfated glycan.

In yet other embodiments, the glycoprotein comprising a sulfated glycan is conjugated to a heterologous moiety. In some embodiments, the heterologous moiety is a polypeptide, nucleic acid, or small molecule. In particular embodiments, the glycoprotein conjugated to a heterologous moiety is a sulfated version of alefacept, abatacept, etanercept, rilonacept, or denileukin diftitox, comprising a sulfated glycan.

In another aspect, the invention features a method of sulfating a glycoprotein. The method comprises providing a glycoprotein comprising an immunoglobulin Fc region, or Fc fragment, comprising a glycan; and contacting the glycoprotein with a glycan sulfotransferase, the sulfotransferase sulfating the glycan of the glycoprotein. In some embodiments, the glycoprotein is an isolated glycoprotein. In other embodiments, the glycoprotein is a purified glycoprotein. In other embodiments, the glycoprotein is a non-naturally occurring or a synthetic glycoprotein.

In some embodiments, the glycan sulfotransferase is a CHST2, CHST4, CHST5, or CHST7 sulfotransferase.

In other embodiments, the glycan is linked to one or more of a CH2 immunoglobulin domain, a CH3 immunoglobulin domain, and a CH4 immunoglobulin domain of the Fc region. In particular embodiments, the glycan is linked to a CH2 domain of an IgG heavy chain. In some embodiments, the glycan is linked to one or more N-glycosylation sites of an IgA, IgD, IgE, IgG, or IgM antibody heavy chain. In yet other embodiments, the glycan is linked to Asn297 of an IgG heavy chain.

In some embodiments, the glycan comprises a branched glycan. In certain embodiments, the glycan comprises one or more of a N-acetylglucosamine, a galactose, or a N-acetylgalactosamine.

In some embodiments, the glycoprotein is a modified glycoprotein comprising one or more amino acid substitutions of a reference glycoprotein. In some embodiments, the modified glycoprotein comprises a modified amino acid sequence of a reference glycoprotein and comprises a modified glycan, wherein the reference glycoprotein comprises an immunoglobulin Fc region, or Fc fragment, comprising a reference glycan, wherein the modified glycoprotein comprises one or more amino acid substitutions of the Fc region, or Fc fragment, of the reference glycoprotein. In some embodiments, the one or more amino acid substitutions result in increased sulfation of the modified glycan relative to the reference glycan.

In some embodiments, at least one of the amino acids substituted is F241, F243, K246, T260, or R301 of an IgG heavy chain. In some embodiments, at least one of the amino acid substitutions is F241A, F243A, K246A, T260A, or R301A.

In some embodiments, the modified glycoprotein comprises two or more amino acid substitutions of the Fc region, or Fc fragment, of the reference glycoprotein. In some embodiments, the two or more amino acid substitutions result in increased sulfation of the modified glycan relative to the reference glycan. In some embodiments, at least two of the amino acid substitutions are selected from F241A, F243A, K246A, T260A, and R301A. In particular embodiments, at least two of the amino acid substitutions are F241A and F243A; F241A and K246A; F241A and T260A; F241A and R301A; F243A and K246A; F243A and T260A; F243A and R301A; K246A and T260A; K246A and R301A; or T260A and R301A.

In some embodiments, the modified glycan has an altered glycan composition (e.g., an altered glycan composition described herein) relative to the reference glycan.

In some embodiments, the modified glycoprotein comprises a modified glycan that is sulfated at a higher level relative to the reference glycan.

In some embodiments, the glycoprotein is provided in a population of glycoproteins, and the glycan sulfotransferase sulfates a glycan of at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 40%, at least about 50%, at least about 60%, at least about 70%, at least about 80%, at least about 90%, at least about 95%, or at least about 100% of the glycoproteins of the population.

In certain embodiments, the glycan is singly sulfated. In other embodiments, the glycan is doubly sulfated.

In some embodiments, the glycoprotein comprises two Fc regions and the sulfotransferase sulfates a glycan linked to one of the Fc regions. In other embodiments, the glycoprotein comprises two Fc regions and the sulfotransferase sulfates glycans linked to both Fc regions.

In other embodiments, the glycoprotein comprising a sulfated glycan, or the modified glycoprotein (e.g., comprising one or more amino acid substitutions) comprising a sulfated glycan, has a different, e.g., a detectably higher or lower, activity, such as an immune cell activating activity, e.g., Fc receptor affinity, Fc receptor specificity, complement activation activity, signaling activity, targeting activity, effector function, half-life, clearance, pro-inflammatory, anti-inflammatory, or transcytosis activity than a corresponding wild type or reference glycoprotein without a sulfated glycan. In some embodiments, the effector function is antibody dependent cellular cytotoxicity, complement dependent cytotoxicity, programmed cell death, or cellular phagocytosis.

In certain embodiments, the Fc receptor is an FcγRI, FcγRIIA, FcγRIIB, FcγRIIIA, FcγRIIIB, FcγRIV, or FcRn receptor. In some embodiments, the glycoprotein binds to an immune cell, e.g., a macrophage, neutrophil, dendritic cell, B cell, natural killer cell (NKC), or eosinophil.

In some embodiments, the glycoprotein is an antibody. In certain embodiments, the antibody is an IgA, IgD, IgE, IgG, or IgM antibody. In particular embodiments, the antibody is an IgG1, IgG2, or IgG3 antibody.

In certain embodiments, the antibody is abciximab, adalimumab, alemtuzumab, basiliximab, bevacizumab, cetuximab, certolizumab, daclizumab, eculizumab, efalizumab, gemtuzumab, ibritumomab, infliximab, muromonab, natalizumab, omalizumab, palivizumab, panitumumab, ranibizumab, rituximab, tositumomab, or trastuzumab.

In yet other embodiments, the glycoprotein is conjugated to a heterologous moiety. In some embodiments, the heterologous moiety is a polypeptide, nucleic acid, or small molecule. In particular embodiments, the glycoprotein conjugated to a heterologous moiety is alefacept, abatacept, etanercept, rilonacept, or denileukin diftitox.

In another aspect, the invention features a method of sulfating a glycoprotein. The method comprises expressing in a cell a recombinant glycoprotein comprising an immunoglobulin Fc region, or an Fc fragment, comprising a glycan; and expressing in the cell a recombinant glycan sulfotransferase, the sulfotransferase sulfating the glycan of the glycoprotein.

In some embodiments, the glycan sulfotransferase is a heterologously expressed glycan sulfotransferase. In certain embodiments, the glycan sulfotransferase is a CHST2, CHST4, CHST5, or CHST7 sulfotransferase.

In other embodiments, the glycan is linked to one or more of a CH2 immunoglobulin domain, a CH3 immunoglobulin domain, and a CH4 immunoglobulin domain of the Fc region. In particular embodiments, the glycan is linked to a CH2 domain of an IgG heavy chain. In some embodiments, the glycan is linked to one or more N-glycosylation sites of an IgA, IgD, IgE, IgG, or IgM antibody heavy chain. In yet other embodiments, the glycan is linked to Asn297 of an IgG heavy chain.

In some embodiments, the glycan comprises a branched glycan. In certain embodiments, the glycan comprises one or more of a N-acetylglucosamine, a galactose, or a N-acetylgalactosamine.

In some embodiments, the glycoprotein is a modified glycoprotein comprising one or more amino acid substitutions of a reference glycoprotein. In some embodiments, the modified glycoprotein comprises a modified amino acid sequence of a reference glycoprotein and comprises a modified glycan, wherein the reference glycoprotein comprises an immunoglobulin Fc region, or Fc fragment, comprising a reference glycan, wherein the modified glycoprotein comprises one or more amino acid substitutions of the Fc region, or Fc fragment, of the reference glycoprotein. In some embodiments, the one or more amino acid substitutions result in increased sulfation of the modified glycan relative to the reference glycan.

In some embodiments, at least one of the amino acids substituted is F241, F243, K246, T260, or R301 of an IgG heavy chain. In some embodiments, at least one of the amino acid substitutions is F241A, F243A, K246A, T260A, or R301A.

In some embodiments, the modified glycoprotein comprises two or more amino acid substitutions of the Fc region, or Fc fragment, of the reference glycoprotein. In some embodiments, the two or more amino acid substitutions result in increased sulfation of the modified glycan relative to the reference glycan. In some embodiments, at least two of the amino acid substitutions are selected from F241A, F243A, K246A, T260A, and R301A. In particular embodiments, at least two of the amino acid substitutions are F241A and F243A; F241A and K246A; F241A and T260A; F241A and R301A; F243A and K246A; F243A and T260A; F243A and R301A; K246A and T260A; K246A and R301A; or T260A and R301A.

In some embodiments, the modified glycan has an altered glycan composition (e.g., an altered glycan composition described herein) relative to the reference glycan.

In some embodiments, the modified glycoprotein comprises a modified glycan that is sulfated at a higher level relative to the reference glycan.

In some embodiments, the method comprises expressing a population of glycoproteins, and the sulfotransferase sulfates a glycan of at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 40%, at least about 50%, at least about 60%, at least about 70%, at least about 80%, at least about 90%, at least about 95%, or at least about 100% of the glycoproteins of the population.

In certain embodiments, the glycan is singly sulfated. In other embodiments, the glycan is doubly sulfated.

In some embodiments, the glycoprotein comprises two Fc regions and the sulfotransferase sulfates a glycan linked to one of the Fc regions. In other embodiments, the glycoprotein comprises two Fc regions and the sulfotransferase sulfates glycans linked to both Fc regions.

In other embodiments, the glycoprotein comprising a sulfated glycan, or the modified glycoprotein (e.g., comprising one or more amino acid substitutions) comprising a sulfated glycan, has a different, e.g., a detectably higher or lower, activity, such as an immune cell activating activity, e.g., Fc receptor affinity, Fc receptor specificity, complement activation activity, signaling activity, targeting activity, effector function, half-life, clearance, pro-inflammatory, anti-inflammatory, or transcytosis activity than a corresponding wild type or reference glycoprotein without a sulfated glycan. In some embodiments, the effector function is antibody dependent cellular cytotoxicity, complement dependent cytotoxicity, programmed cell death, or cellular phagocytosis.

In certain embodiments, the Fc receptor is an FcγRI, FcγRIIA, FcγRIIB, FcγRIIIA, FcγRIIIB, FcγRIV, or FcRn receptor. In some embodiments, the glycoprotein binds to an immune cell, e.g., a macrophage, neutrophil, dendritic cell, B cell, natural killer cell (NKC), or eosinophil.

In some embodiments, the glycoprotein is an antibody. In certain embodiments, the antibody is an IgA, IgD, IgE, IgG, or IgM antibody. In particular embodiments, the antibody is an IgG1, IgG2, or IgG3 antibody.

In certain embodiments, the antibody is abciximab, adalimumab, alemtuzumab, basiliximab, bevacizumab, cetuximab, certolizumab, daclizumab, eculizumab, efalizumab, gemtuzumab, ibritumomab, infliximab, muromonab, natalizumab, omalizumab, palivizumab, panitumumab, ranibizumab, rituximab, tositumomab, or trastuzumab.

In yet other embodiments, the glycoprotein is conjugated to a heterologous moiety. In some embodiments, the heterologous moiety is a polypeptide, nucleic acid, or small molecule. In particular embodiments, the glycoprotein conjugated to a heterologous moiety is alefacept, abatacept, etanercept, rilonacept, or denileukin diftitox.

In some embodiments, the cell is an animal cell, a mammalian cell, a bacterial cell, an insect cell, a fungal cell, or a yeast cell.

In another aspect, the invention features a method of selectively targeting a glycoprotein to a cell or tissue. The method comprises: providing a glycoprotein comprising a sulfated immunoglobulin Fc region, or a sulfated Fc fragment thereof; and contacting the glycoprotein with a cell or tissue comprising a target Fc receptor, thereby selectively targeting the glycoprotein to the cell or tissue. In certain embodiments, the sulfated Fc region comprises one or more of a CH2 immunoglobulin domain, a CH3 immunoglobulin domain, and a CH4 immunoglobulin domain. In particular embodiments, the sulfated Fc region comprises a CH2 domain of an IgG heavy chain. In some embodiments, the sulfated Fc region comprises one or more N-glycosylation sites of an IgA, IgD, IgE, IgG, or IgM antibody heavy chain. In yet other embodiments, the Fc region comprises Asn297 of an IgG heavy chain.

In some embodiments, the glycoprotein is an isolated glycoprotein. In other embodiments, the glycoprotein is a purified glycoprotein. In other embodiments, the glycoprotein is a non-naturally occurring or a synthetic glycoprotein.

In certain embodiments, the glycoprotein comprises an Fc region or an Fc fragment comprising a sulfated glycan. In certain embodiments, the sulfated glycan is linked to one or more of a CH2 immunoglobulin domain, a CH3 immunoglobulin domain, and a CH4 immunoglobulin domain. In particular embodiments, the sulfated glycan is linked to a CH2 domain of an IgG heavy chain. In some embodiments, the sulfated glycan is linked to one or more N-glycosylation sites of an IgA, IgD, IgE, IgG, or IgM antibody heavy chain. In yet other embodiments, the sulfated glycan is linked to Asn297 of an IgG heavy chain.

In some embodiments, the sulfated glycan comprises a branched glycan. In certain embodiments, the sulfated glycan comprises one or more of a sulfated N-acetylglucosamine, a sulfated galactose, or a sulfated N-acetylgalactosamine.

In some embodiments, the glycoprotein is a modified glycoprotein comprising one or more amino acid substitutions of a reference glycoprotein. In some embodiments, the modified glycoprotein comprises a modified amino acid sequence of a reference glycoprotein and comprises a modified glycan, wherein the reference glycoprotein comprises an immunoglobulin Fc region, or Fc fragment, comprising a reference glycan, wherein the modified glycoprotein comprises one or more amino acid substitutions of the Fc region, or Fc fragment, of the reference glycoprotein. In some embodiments, the one or more amino acid substitutions result in increased sulfation of the modified glycan relative to the reference glycan.

In some embodiments, at least one of the amino acids substituted is F241, F243, K246, T260, or R301 of an IgG heavy chain. In some embodiments, at least one of the amino acid substitutions is F241A, F243A, K246A, T260A, or R301A.

In some embodiments, the modified glycoprotein comprises two or more amino acid substitutions of the Fc region, or Fc fragment, of the reference glycoprotein. In some embodiments, the two or more amino acid substitutions result in increased sulfation of the modified glycan relative to the reference glycan. In some embodiments, at least two of the amino acid substitutions are selected from F241A, F243A, K246A, T260A, and R301A. In particular embodiments, at least two of the amino acid substitutions are F241A and F243A; F241A and K246A; F241A and T260A; F241A and R301A; F243A and K246A; F243A and T260A; F243A and R301A; K246A and T260A; K246A and R301A; or T260A and R301A.

In some embodiments, the modified glycan has an altered glycan composition (e.g., an altered glycan composition described herein) relative to the reference glycan.

In some embodiments, the modified glycoprotein comprises a modified glycan that is sulfated at a higher level relative to the reference glycan.

In some embodiments, the glycoprotein is provided in a population of glycoproteins, wherein at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 40%, at least about 50%, at least about 60%, at least about 70%, at least about 80%, at least about 90%, at least about 95%, or at least about 100% of the glycoproteins of the population comprise a sulfated Fc region or a sulfated Fc fragment.

In certain embodiments, the glycan is singly sulfated. In other embodiments, the glycan is doubly sulfated.

In some embodiments, the glycoprotein comprises two Fc regions, wherein one of the Fc regions is sulfated. In other embodiments, the glycoprotein comprises two Fc regions wherein both Fc regions are sulfated.

In other embodiments, the glycoprotein comprising a sulfated Fc region or sulfated Fc fragment, or the modified glycoprotein (e.g., comprising one or more amino acid substitutions) comprising a sulfated Fc region or sulfated Fc fragment, has a different, e.g., a detectably higher or lower, activity, such as an immune cell activating activity, e.g., Fc receptor affinity, Fc receptor specificity, complement activation activity, signaling activity, targeting activity, effector function, half-life, clearance, pro-inflammatory, anti-inflammatory, or transcytosis activity than a corresponding wild type or reference glycoprotein without a sulfated Fc region or a sulfated Fc fragment. In some embodiments, the effector function is antibody dependent cellular cytotoxicity, complement dependent cytotoxicity, programmed cell death, or cellular phagocytosis.

In certain embodiments, the Fc receptor is an FcγRI, FcγRIIA, FcγRIIB, FcγRIIIA, FcγRIIIB, FcγRIV, or FcRn receptor. In some embodiments, the glycoprotein binds to an immune cell, e.g., a macrophage, neutrophil, dendritic cell, B cell, natural killer cell (NKC), or eosinophil.

In some embodiments, the glycoprotein comprising a sulfated Fc region or sulfated Fc fragment is an antibody comprising a sulfated Fc region or sulfated Fc fragment. In certain embodiments, the antibody is an IgA, IgD, IgE, IgG, or IgM antibody. In particular embodiments, the antibody is an IgG1, IgG2, or IgG3 antibody.

In certain embodiments, the antibody comprising a sulfated Fc region or sulfated Fc fragment is a sulfated version of abciximab, adalimumab, alemtuzumab, basiliximab, bevacizumab, cetuximab, certolizumab, daclizumab, eculizumab, efalizumab, gemtuzumab, ibritumomab, infliximab, muromonab, natalizumab, omalizumab, palivizumab, panitumumab, ranibizumab, rituximab, tositumomab, or trastuzumab, comprising a sulfated Fc region or sulfated Fc fragment.

In yet other embodiments, the glycoprotein comprising a sulfated Fc region or sulfated Fc fragment is conjugated to a heterologous moiety. In some embodiments, the heterologous moiety is a polypeptide, nucleic acid, or small molecule. In particular embodiments, the glycoprotein conjugated to a heterologous moiety is a sulfated version of alefacept, abatacept, etanercept, rilonacept, or denileukin diftitox, comprising a sulfated Fc region or sulfated Fc fragment.

In another aspect, the invention features a method of selectively targeting a glycoprotein to a cell or tissue. The method comprises: providing a glycoprotein comprising an immunoglobulin Fc region, or Fc fragment, comprising a sulfated glycan; and contacting the glycoprotein with a cell or tissue comprising a target Fc receptor, thereby selectively targeting the glycoprotein to the cell or tissue. In some embodiments, the glycoprotein is an isolated glycoprotein. In other embodiments, the glycoprotein is a purified glycoprotein. In other embodiments, the glycoprotein is a non-naturally occurring or a synthetic glycoprotein.

In certain embodiments, the sulfated glycan is linked to one or more of a CH2 immunoglobulin domain, a CH3 immunoglobulin domain, and a CH4 immunoglobulin domain of the Fc region. In particular embodiments, the sulfated glycan is linked to a CH2 domain of an IgG heavy chain. In some embodiments, the sulfated glycan is linked to one or more N-glycosylation sites of an IgA, IgD, IgE, IgG, or IgM antibody heavy chain. In yet other embodiments, the sulfated glycan is linked to Asn297 of an IgG heavy chain.

In some embodiments, the sulfated glycan comprises a branched glycan. In certain embodiments, the sulfated glycan comprises one or more of a sulfated N-acetylglucosamine, a sulfated galactose, or a sulfated N-acetylgalactosamine.

In some embodiments, the glycoprotein is a modified glycoprotein comprising one or more amino acid substitutions of a reference glycoprotein. In some embodiments, the modified glycoprotein comprises a modified amino acid sequence of a reference glycoprotein and comprises a modified glycan, wherein the reference glycoprotein comprises an immunoglobulin Fc region, or Fc fragment, comprising a reference glycan, wherein the modified glycoprotein comprises one or more amino acid substitutions of the Fc region, or Fc fragment, of the reference glycoprotein. In some embodiments, the one or more amino acid substitutions result in increased sulfation of the modified glycan relative to the reference glycan.

In some embodiments, at least one of the amino acids substituted is F241, F243, K246, T260, or R301 of an IgG heavy chain. In some embodiments, at least one of the amino acid substitutions is F241A, F243A, K246A, T260A, or R301A.

In some embodiments, the modified glycoprotein comprises two or more amino acid substitutions of the Fc region, or Fc fragment, of the reference glycoprotein. In some embodiments, the two or more amino acid substitutions result in increased sulfation of the modified glycan relative to the reference glycan. In some embodiments, at least two of the amino acid substitutions are selected from F241A, F243A, K246A, T260A, and R301A. In particular embodiments, at least two of the amino acid substitutions are F241A and F243A; F241A and K246A; F241A and T260A; F241A and R301A; F243A and K246A; F243A and T260A; F243A and R301A; K246A and T260A; K246A and R301A; or T260A and R301A.

In some embodiments, the modified glycan has an altered glycan composition (e.g., an altered glycan composition described herein) relative to the reference glycan.

In some embodiments, the modified glycoprotein comprises a modified glycan that is sulfated at a higher level relative to the reference glycan.

In some embodiments, the glycoprotein is provided in a population of glycoproteins, wherein at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 40%, at least about 50%, at least about 60%, at least about 70%, at least about 80%, at least about 90%, at least about 95%, or at least about 100% of the glycoproteins of the population comprise a sulfated glycan.

In certain embodiments, the glycan is singly sulfated. In other embodiments, the glycan is doubly sulfated.

In some embodiments, the glycoprotein comprises two Fc regions, wherein the sulfated glycan is linked to one of the Fc regions. In other embodiments, the glycoprotein comprises two Fc regions wherein sulfated glycans are linked to both Fc regions.

In other embodiments, the glycoprotein comprising a sulfated glycan, or the modified glycoprotein (e.g., comprising one or more amino acid substitutions) comprising a sulfated glycan, has a different, e.g., a detectably higher or lower, activity, such as an immune cell activating activity, e.g., Fc receptor affinity, Fc receptor specificity, complement activation activity, signaling activity, targeting activity, effector function, half-life, clearance, pro-inflammatory, anti-inflammatory, or transcytosis activity than a corresponding wild type or reference glycoprotein without a sulfated glycan. In some embodiments, the effector function is antibody dependent cellular cytotoxicity, complement dependent cytotoxicity, programmed cell death, or cellular phagocytosis.

In certain embodiments, the Fc receptor is an FcγRI, FcγRIIA, FcγRIIB, FcγRIIIA, FcγRIIIB, FcγRIV, or FcRn receptor. In some embodiments, the glycoprotein binds to an immune cell, e.g., a macrophage, neutrophil, dendritic cell, B cell, natural killer cell (NKC), or eosinophil.

In some embodiments, the glycoprotein comprising a sulfated glycan is an antibody comprising a sulfated glycan. In certain embodiments, the antibody is an IgA, IgD, IgE, IgG, or IgM antibody. In particular embodiments, the antibody is an IgG1, IgG2, or IgG3 antibody.

In certain embodiments, the antibody comprising a sulfated glycan is a sulfated version of abciximab, adalimumab, alemtuzumab, basiliximab, bevacizumab, cetuximab, certolizumab, daclizumab, eculizumab, efalizumab, gemtuzumab, ibritumomab, infliximab, muromonab, natalizumab, omalizumab, palivizumab, panitumumab, ranibizumab, rituximab, tositumomab, or trastuzumab, comprising a sulfated glycan.

In yet other embodiments, the glycoprotein comprising a sulfated glycan is conjugated to a heterologous moiety. In some embodiments, the heterologous moiety is a polypeptide, nucleic acid, or small molecule. In particular embodiments, the glycoprotein conjugated to a heterologous moiety is a sulfated version of alefacept, abatacept, etanercept, rilonacept, or denileukin diftitox, comprising a sulfated glycan.

In another aspect, the invention features a method of modifying activity of a glycoprotein. The method comprises providing a glycoprotein comprising an immunoglobulin Fc region, or Fc fragment, comprising a glycan; and sulfating the glycan, the sulfated glycoprotein having a different, e.g., a detectably higher or lower, activity, such as an immune cell activating activity, e.g., Fc receptor affinity, Fc receptor specificity, complement activation activity, signaling activity, targeting activity, effector function, half-life, clearance, pro-inflammatory, anti-inflammatory, or transcytosis activity than a corresponding wild type or reference glycoprotein without a sulfated glycan. In some embodiments, the effector function is antibody dependent cellular cytotoxicity, complement dependent cytotoxicity, programmed cell death, or cellular phagocytosis.

In certain embodiments, the Fc receptor is an FcγRI, FcγRIIA, FcγRIIB, FcγRIIIA, FcγRIIIB, FcγRIV, or FcRn receptor. In some embodiments, the glycoprotein binds to an immune cell, e.g., a macrophage, neutrophil, dendritic cell, B cell, natural killer cell (NKC), or eosinophil.

In some embodiments, the sulfating step comprises contacting the glycoprotein with a glycan sulfotransferase, the sulfotransferase sulfating the glycan of the glycoprotein. In some embodiments, the glycoprotein is an isolated glycoprotein. In other embodiments, the glycoprotein is a purified glycoprotein. In other embodiments, the glycoprotein is a non-naturally occurring or a synthetic glycoprotein.

In some embodiments, the glycan sulfotransferase is a CHST2, CHST4, CHST5, or CHST7 sulfotransferase.

In other embodiments, the glycan is linked to one or more of a CH2 immunoglobulin domain, a CH3 immunoglobulin domain, and a CH4 immunoglobulin domain of the Fc region. In particular embodiments, the glycan is linked to a CH2 domain of an IgG heavy chain. In some embodiments, the glycan is linked to one or more N-glycosylation sites of an IgA, IgD, IgE, IgG, or IgM antibody heavy chain. In yet other embodiments, the glycan is linked to Asn297 of an IgG heavy chain.

In some embodiments, the glycan comprises a branched glycan. In certain embodiments, the glycan comprises one or more of a N-acetylglucosamine, a galactose, or a N-acetylgalactosamine.

In some embodiments, the glycoprotein is a modified glycoprotein comprising one or more amino acid substitutions of a reference glycoprotein. In some embodiments, the modified glycoprotein comprises a modified amino acid sequence of a reference glycoprotein and comprises a modified glycan, wherein the reference glycoprotein comprises an immunoglobulin Fc region, or Fc fragment, comprising a reference glycan, wherein the modified glycoprotein comprises one or more amino acid substitutions of the Fc region, or Fc fragment, of the reference glycoprotein. In some embodiments, the one or more amino acid substitutions result in increased sulfation of the modified glycan relative to the reference glycan.

In some embodiments, at least one of the amino acids substituted is F241, F243, K246, T260, or R301 of an IgG heavy chain. In some embodiments, at least one of the amino acid substitutions is F241A, F243A, K246A, T260A, or R301A.

In some embodiments, the modified glycoprotein comprises two or more amino acid substitutions of the Fc region, or Fc fragment, of the reference glycoprotein. In some embodiments, the two or more amino acid substitutions result in increased sulfation of the modified glycan relative to the reference glycan. In some embodiments, at least two of the amino acid substitutions are selected from F241A, F243A, K246A, T260A, and R301A. In particular embodiments, at least two of the amino acid substitutions are F241A and F243A; F241A and K246A; F241A and T260A; F241A and R301A; F243A and K246A; F243A and T260A; F243A and R301A; K246A and T260A; K246A and R301A; or T260A and R301A.

In some embodiments, the modified glycan has an altered glycan composition (e.g., an altered glycan composition described herein) relative to the reference glycan.

In some embodiments, the modified glycoprotein comprises a modified glycan that is sulfated at a higher level relative to the reference glycan.

In some embodiments, the glycoprotein is provided in a population of glycoproteins, and wherein at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 40%, at least about 50%, at least about 60%, at least about 70%, at least about 80%, at least about 90%, at least about 95%, or at least about 100% of the glycoproteins are sulfated.

In certain embodiments, the glycan is singly sulfated. In other embodiments, the glycan is doubly sulfated.

In some embodiments, the glycoprotein comprises two Fc regions a glycan linked to one of the Fc regions is sulfated. In other embodiments, the glycoprotein comprises two Fc regions and glycans linked to both Fc regions are sulfated.

In some embodiments, the glycoprotein is an antibody. In certain embodiments, the antibody is an IgA, IgD, IgE, IgG, or IgM antibody. In particular embodiments, the antibody is an IgG1, IgG2, or IgG3 antibody.

In certain embodiments, the antibody is abciximab, adalimumab, alemtuzumab, basiliximab, bevacizumab, cetuximab, certolizumab, daclizumab, eculizumab, efalizumab, gemtuzumab, ibritumomab, infliximab, muromonab, natalizumab, omalizumab, palivizumab, panitumumab, ranibizumab, rituximab, tositumomab, or trastuzumab.

In yet other embodiments, the glycoprotein is conjugated to a heterologous moiety. In some embodiments, the heterologous moiety is a polypeptide, nucleic acid, or small molecule. In particular embodiments, the glycoprotein conjugated to a heterologous moiety is alefacept, abatacept, etanercept, rilonacept, or denileukin diftitox.

In another aspect, the invention features a method of treating a subject with a therapeutic glycoprotein. The method comprises providing a therapeutic glycoprotein comprising a sulfated immunoglobulin Fc region, or a sulfated Fc fragment; and administering the sulfated therapeutic glycoprotein to a subject in need thereof, the sulfated therapeutic glycoprotein having a level of activity different than a corresponding therapeutic glycoprotein not comprising a sulfated Fc region or sulfated Fc fragment, thereby treating the subject. In some embodiments, the sulfated Fc region or the sulfated Fc fragment comprises one or more N-glycosylation sites of an Fc region. In certain embodiments, the sulfated Fc region comprises one or more of a CH2 immunoglobulin domain, a CH3 immunoglobulin domain, and a CH4 immunoglobulin domain. In particular embodiments, the sulfated Fc region comprises a CH2 domain of an IgG heavy chain. In some embodiments, the sulfated Fc region comprises one or more N-glycosylation sites of an IgA, IgD, IgE, IgG, or IgM antibody heavy chain. In yet other embodiments, the Fc region comprises Asn297 of an IgG heavy chain.

In some embodiments, the glycoprotein is an isolated glycoprotein. In other embodiments, the glycoprotein is a purified glycoprotein. In other embodiments, the glycoprotein is a non-naturally occurring or a synthetic glycoprotein.

In certain embodiments, the glycoprotein comprises an Fc region or an Fc fragment comprising a sulfated glycan. In certain embodiments, the sulfated glycan is linked to one or more of a CH2 immunoglobulin domain, a CH3 immunoglobulin domain, and a CH4 immunoglobulin domain. In particular embodiments, the sulfated glycan is linked to a CH2 domain of an IgG heavy chain. In some embodiments, the sulfated glycan is linked to one or more N-glycosylation sites of an IgA, IgD, IgE, IgG, or IgM antibody heavy chain. In yet other embodiments, the sulfated glycan is linked to Asn297 of an IgG heavy chain.

In some embodiments, the sulfated glycan comprises a branched glycan. In certain embodiments, the sulfated glycan comprises one or more of a sulfated N-acetylglucosamine, a sulfated galactose, or a sulfated N-acetylgalactosamine.

In some embodiments, the glycoprotein is a modified glycoprotein comprising one or more amino acid substitutions of a reference glycoprotein. In some embodiments, the modified glycoprotein comprises a modified amino acid sequence of a reference glycoprotein and comprises a modified glycan, wherein the reference glycoprotein comprises an immunoglobulin Fc region, or Fc fragment, comprising a reference glycan, wherein the modified glycoprotein comprises one or more amino acid substitutions of the Fc region, or Fc fragment, of the reference glycoprotein. In some embodiments, the one or more amino acid substitutions result in increased sulfation of the modified glycan relative to the reference glycan.

In some embodiments, at least one of the amino acids substituted is F241, F243, K246, T260, or R301 of an IgG heavy chain. In some embodiments, at least one of the amino acid substitutions is F241A, F243A, K246A, T260A, or R301A.

In some embodiments, the modified glycoprotein comprises two or more amino acid substitutions of the Fc region, or Fc fragment, of the reference glycoprotein. In some embodiments, the two or more amino acid substitutions result in increased sulfation of the modified glycan relative to the reference glycan. In some embodiments, at least two of the amino acid substitutions are selected from F241A, F243A, K246A, T260A, and R301A. In particular embodiments, at least two of the amino acid substitutions are F241A and F243A; F241A and K246A; F241A and T260A; F241A and R301A; F243A and K246A; F243A and T260A; F243A and R301A; K246A and T260A; K246A and R301A; or T260A and R301A.

In some embodiments, the modified glycan has an altered glycan composition (e.g., an altered glycan composition described herein) relative to the reference glycan.

In some embodiments, the modified glycoprotein comprises a modified glycan that is sulfated at a higher level relative to the reference glycan.

In some embodiments, the therapeutic glycoprotein is provided in a population of glycoproteins, wherein at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 40%, at least about 50%, at least about 60%, at least about 70%, at least about 80%, at least about 90%, at least about 95%, or at least about 100% of the glycoproteins comprise a sulfated Fc region or a sulfated Fc fragment.

In certain embodiments, the glycan is singly sulfated. In other embodiments, the glycan is doubly sulfated.

In some embodiments, the glycoprotein comprises two Fc regions, wherein one of the Fc regions is sulfated. In other embodiments, the glycoprotein comprises two Fc regions wherein both Fc regions are sulfated.

In other embodiments, the glycoprotein comprising a sulfated Fc region or sulfated Fc fragment, or the modified glycoprotein (e.g., comprising one or more amino acid substitutions) comprising a sulfated Fc region or sulfated Fc fragment, has a different, e.g., a detectably higher or lower, activity, such as an immune cell activating activity, e.g., Fc receptor affinity, Fc receptor specificity, complement activation activity, signaling activity, targeting activity, effector function, half-life, clearance, pro-inflammatory, anti-inflammatory, or transcytosis activity than a corresponding wild type or reference glycoprotein without a sulfated Fc region or a sulfated Fc fragment. In some embodiments, the effector function is antibody dependent cellular cytotoxicity, complement dependent cytotoxicity, programmed cell death, or cellular phagocytosis.

In certain embodiments, the Fc receptor is an FcγRI, FcγRIIA, FcγRIIB, FcγRIIIA, FcγRIIIB, FcγRIV, or FcRn receptor. In some embodiments, the glycoprotein binds to an immune cell, e.g., a macrophage, neutrophil, dendritic cell, B cell, natural killer cell (NKC), or eosinophil.

In some embodiments, the glycoprotein comprising a sulfated Fc region or sulfated Fc fragment is an antibody comprising a sulfated Fc region or sulfated Fc fragment. In certain embodiments, the antibody is an IgA, IgD, IgE, IgG, or IgM antibody. In particular embodiments, the antibody is an IgG1, IgG2, or IgG3 antibody.

In certain embodiments, the antibody comprising a sulfated Fc region or sulfated Fc fragment is a sulfated version of abciximab, adalimumab, alemtuzumab, basiliximab, bevacizumab, cetuximab, certolizumab, daclizumab, eculizumab, efalizumab, gemtuzumab, ibritumomab, infliximab, muromonab, natalizumab, omalizumab, palivizumab, panitumumab, ranibizumab, rituximab, tositumomab, or trastuzumab, comprising a sulfated Fc region or sulfated Fc fragment.

In yet other embodiments, the glycoprotein comprising a sulfated Fc region or sulfated Fc fragment is conjugated to a heterologous moiety. In some embodiments, the heterologous moiety is a polypeptide, nucleic acid, or small molecule. In particular embodiments, the glycoprotein conjugated to a heterologous moiety is a sulfated version of alefacept, abatacept, etanercept, rilonacept, or denileukin diftitox, comprising a sulfated Fc region or sulfated Fc fragment.

In some embodiments, the subject is a mammal, e.g., a human or non-human primate (such as an ape, monkey, orangutan, or chimpanzee), a dog, cat, guinea pig, rabbit, rat, mouse, horse, cattle, or cow.

In some embodiments, the glycoprotein is formulated as a pharmaceutical composition.

In another aspect, the invention features a method of treating a subject with a therapeutic glycoprotein. The method comprises providing a therapeutic glycoprotein comprising an immunoglobulin Fc region comprising a sulfated glycan; and administering the sulfated therapeutic glycoprotein to a subject in need thereof, the sulfated therapeutic glycoprotein having a level of activity different than a corresponding therapeutic glycoprotein not comprising a sulfated glycan, thereby treating the subject.

In some embodiments, the providing step comprises sulfating the glycan. In certain embodiments, sulfating comprises contacting the glycoprotein with a glycan sulfotransferase, the sulfotransferase sulfating the glycan of the glycoprotein. In some embodiments, the glycan sulfotransferase is a CHST2, CHST4, CHST5, or CHST7 sulfotransferase. In some embodiments, the glycoprotein is an isolated glycoprotein. In other embodiments, the glycoprotein is a purified glycoprotein. In other embodiments, the glycoprotein is a non-naturally occurring or a synthetic glycoprotein.

In certain embodiments, the sulfated glycan is linked to one or more of a CH2 immunoglobulin domain, a CH3 immunoglobulin domain, and a CH4 immunoglobulin domain of the Fc region. In particular embodiments, the sulfated glycan is linked to a CH2 domain of an IgG heavy chain. In some embodiments, the sulfated glycan is linked to one or more N-glycosylation sites of an IgA, IgD, IgE, IgG, or IgM antibody heavy chain. In yet other embodiments, the sulfated glycan is linked to Asn297 of an IgG heavy chain.

In some embodiments, the sulfated glycan comprises a branched glycan. In certain embodiments, the sulfated glycan comprises one or more of a sulfated N-acetylglucosamine, a sulfated galactose, or a sulfated N-acetylgalactosamine.

In some embodiments, the glycoprotein is a modified glycoprotein comprising one or more amino acid substitutions of a reference glycoprotein. In some embodiments, the modified glycoprotein comprises a modified amino acid sequence of a reference glycoprotein and comprises a modified glycan, wherein the reference glycoprotein comprises an immunoglobulin Fc region, or Fc fragment, comprising a reference glycan, wherein the modified glycoprotein comprises one or more amino acid substitutions of the Fc region, or Fc fragment, of the reference glycoprotein. In some embodiments, the one or more amino acid substitutions result in increased sulfation of the modified glycan relative to the reference glycan.

In some embodiments, at least one of the amino acids substituted is F241, F243, K246, T260, or R301 of an IgG heavy chain. In some embodiments, at least one of the amino acid substitutions is F241A, F243A, K246A, T260A, or R301A.

In some embodiments, the modified glycoprotein comprises two or more amino acid substitutions of the Fc region, or Fc fragment, of the reference glycoprotein. In some embodiments, the two or more amino acid substitutions result in increased sulfation of the modified glycan relative to the reference glycan. In some embodiments, at least two of the amino acid substitutions are selected from F241A, F243A, K246A, T260A, and R301A. In particular embodiments, at least two of the amino acid substitutions are F241A and F243A; F241A and K246A; F241A and T260A; F241A and R301A; F243A and K246A; F243A and T260A; F243A and R301A; K246A and T260A; K246A and R301A; or T260A and R301A.

In some embodiments, the modified glycan has an altered glycan composition (e.g., an altered glycan composition described herein) relative to the reference glycan.

In some embodiments, the modified glycoprotein comprises a modified glycan that is sulfated at a higher level relative to the reference glycan.

In some embodiments, the therapeutic glycoprotein is provided in a population of glycoproteins, wherein at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 40%, at least about 50%, at least about 60%, at least about 70%, at least about 80%, at least about 90%, at least about 95%, or at least about 100% of the glycoproteins of the population comprise a sulfated glycan.

In certain embodiments, the glycan is singly sulfated. In other embodiments, the glycan is doubly sulfated.

In some embodiments, the glycoprotein comprises two Fc regions, wherein the sulfated glycan is linked to one of the Fc regions. In other embodiments, the glycoprotein comprises two Fc regions wherein sulfated glycans are linked to both Fc regions.

In other embodiments, the glycoprotein comprising a sulfated glycan, or the modified glycoprotein (e.g., comprising one or more amino acid substitutions) comprising a sulfated glycan, has a different, e.g., a detectably higher or lower, activity, such as an immune cell activating activity, e.g., Fc receptor affinity, Fc receptor specificity, complement activation activity, signaling activity, targeting activity, effector function, half-life, clearance, pro-inflammatory, anti-inflammatory, or transcytosis activity than a corresponding wild type or reference glycoprotein without a sulfated glycan. In some embodiments, the effector function is antibody dependent cellular cytotoxicity, complement dependent cytotoxicity, programmed cell death, or cellular phagocytosis.

In certain embodiments, the Fc receptor is an FcγRI, FcγRIIA, FcγRIIB, FcγRIIIA, FcγRIIIB, FcγRIV, or FcRn receptor. In some embodiments, the glycoprotein binds to an immune cell, e.g., a macrophage, neutrophil, dendritic cell, B cell, natural killer cell (NKC), or eosinophil.

In some embodiments, the glycoprotein comprising a sulfated glycan is an antibody comprising a sulfated glycan. In certain embodiments, the antibody is an IgA, IgD, IgE, IgG, or IgM antibody. In particular embodiments, the antibody is an IgG1, IgG2, or IgG3 antibody.

In certain embodiments, the antibody comprising a sulfated glycan is a sulfated version of abciximab, adalimumab, alemtuzumab, basiliximab, bevacizumab, cetuximab, certolizumab, daclizumab, eculizumab, efalizumab, gemtuzumab, ibritumomab, infliximab, muromonab, natalizumab, omalizumab, palivizumab, panitumumab, ranibizumab, rituximab, tositumomab, or trastuzumab, comprising a sulfated glycan.

In yet other embodiments, the glycoprotein comprising a sulfated glycan is conjugated to a heterologous moiety. In some embodiments, the heterologous moiety is a polypeptide, nucleic acid, or small molecule. In particular embodiments, the glycoprotein conjugated to a heterologous moiety is a sulfated version of alefacept, abatacept, etanercept, rilonacept, or denileukin diftitox, comprising a sulfated glycan.

In some embodiments, the subject is a mammal, e.g., a human or non-human primate (such as an ape, monkey, orangutan, or chimpanzee), a dog, cat, guinea pig, rabbit, rat, mouse, horse, cattle, or cow.

In some embodiments, the glycoprotein is formulated as a pharmaceutical composition.

In another aspect, the invention features a method of sulfating a branched glycan. The method comprises providing a branched glycan; and contacting the branched glycan with a sulfotransferase selected from the group consisting of CHST2, CHST4, CHST5, and CHST7, wherein the sulfotransferase sulfates the glycan.

In some embodiments, the glycan is an N-acetylglucosamine, a galactose, or a N-acetylgalactosamine.

In another aspect, the invention features a cell comprising a nucleic acid encoding an exogenous glycan sulfotransferase; and a nucleic acid encoding a recombinant glycoprotein comprising an immunoglobulin Fc region, e.g., an antibody or Fc-fusion protein, e.g., an antibody or Fc-fusion protein described herein. In some embodiments, the cell is an animal cell, a mammalian cell, a bacterial cell, an insect cell, a fungal cell, or a yeast cell.

In another aspect, the invention features a glycoprotein comprising a sulfated Fc region, a sulfated Fc fragment, or a sulfated glycan, produced by a method or a cell described herein.

In another aspect, the invention features an antibody, or a portion thereof, comprising a sulfated immunoglobulin Fc region, or sulfated Fc fragment. In some embodiments, the sulfated Fc region or the sulfated Fc fragment comprises one or more N-glycosylation sites of an Fc region. In certain embodiments, the sulfated Fc region comprises one or more of a CH2 immunoglobulin domain, a CH3 immunoglobulin domain, and a CH4 immunoglobulin domain. In particular embodiments, the sulfated Fc region comprises a CH2 domain of an IgG heavy chain. In some embodiments, the sulfated Fc region comprises one or more N-glycosylation sites of an IgA, IgD, IgE, IgG, or IgM antibody heavy chain. In yet other embodiments, the Fc region comprises Asn297 of an IgG heavy chain.

In some embodiments, the antibody, or portion thereof, is an isolated antibody, or portion thereof. In other embodiments, the antibody, or portion thereof, is a purified antibody, or portion thereof. In other embodiments, the antibody, or portion thereof, is a non-naturally occurring or a synthetic antibody, or portion thereof.

In certain embodiments, the antibody, or portion thereof, comprises an Fc region or an Fc fragment comprising a sulfated glycan. In certain embodiments, the sulfated glycan is linked to one or more of a CH2 immunoglobulin domain, a CH3 immunoglobulin domain, and a CH4 immunoglobulin domain. In particular embodiments, the sulfated glycan is linked to a CH2 domain of an IgG heavy chain. In some embodiments, the sulfated glycan is linked to one or more N-glycosylation sites of an IgA, IgD, IgE, IgG, or IgM antibody heavy chain. In yet other embodiments, the sulfated glycan is linked to Asn297 of an IgG heavy chain.

In some embodiments, the sulfated glycan comprises a branched glycan. In certain embodiments, the sulfated glycan comprises one or more of a sulfated N-acetylglucosamine, a sulfated galactose, or a sulfated N-acetylgalactosamine.

In some embodiments, the antibody, or portion thereof, is a modified antibody or portion thereof comprising one or more amino acid substitutions of a reference antibody or portion thereof. In some embodiments, the modified antibody or portion thereof comprises a modified amino acid sequence of a reference antibody or portion thereof and comprises a modified glycan, wherein the reference antibody or portion thereof comprises an immunoglobulin Fc region, or Fc fragment, comprising a reference glycan, wherein the modified antibody or portion thereof comprises one or more amino acid substitutions of the Fc region, or Fc fragment, of the reference antibody or portion thereof. In some embodiments, the one or more amino acid substitutions result in increased sulfation of the modified glycan relative to the reference glycan.

In some embodiments, at least one of the amino acids substituted is F241, F243, K246, T260, or R301 of an IgG heavy chain. In some embodiments, at least one of the amino acid substitutions is F241A, F243A, K246A, T260A, or R301A.

In some embodiments, the modified antibody or portion thereof comprises two or more amino acid substitutions of the Fc region, or Fc fragment, of the reference antibody or portion thereof. In some embodiments, the two or more amino acid substitutions result in increased sulfation of the modified glycan relative to the reference glycan. In some embodiments, at least two of the amino acid substitutions are selected from F241A, F243A, K246A, T260A, and R301A. In particular embodiments, at least two of the amino acid substitutions are F241A and F243A; F241A and K246A; F241A and T260A; F241A and R301A; F243A and K246A; F243A and T260A; F243A and R301A; K246A and T260A; K246A and R301A; or T260A and R301A.

In some embodiments, the modified glycan has an altered glycan composition (e.g., an altered glycan composition described herein) relative to the reference glycan.

In some embodiments, the antibody or portion thereof is present in a population of antibodies, portions thereof, or both, wherein at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 40%, at least about 50%, at least about 60%, at least about 70%, at least about 80%, at least about 90%, at least about 95%, or at least about 100% of the antibodies, portions thereof, or both, of the population comprise a sulfated Fc region or a sulfated Fc fragment.

In certain embodiments, the glycan is singly sulfated. In other embodiments, the glycan is doubly sulfated.

In some embodiments, the antibody or portion thereof comprises two Fc regions, wherein one of the Fc regions is sulfated. In other embodiments, the antibody or portion thereof comprises two Fc regions wherein both Fc regions are sulfated.

In other embodiments, the antibody or portion thereof comprising a sulfated Fc region or sulfated Fc fragment, or the modified antibody (e.g., comprising one or more amino acid substitutions), or portion thereof, comprising a sulfated Fc region or sulfated Fc fragment, has a different, e.g., a detectably higher or lower, activity, such as an immune cell activating activity, e.g., Fc receptor affinity, Fc receptor specificity, complement activation activity, signaling activity, targeting activity, effector function, half-life, clearance, pro-inflammatory, anti-inflammatory, or transcytosis activity than a corresponding wild type or reference antibody or portion thereof without a sulfated Fc region or a sulfated Fc fragment. In some embodiments, the effector function is antibody dependent cellular cytotoxicity, complement dependent cytotoxicity, programmed cell death, or cellular phagocytosis.

In certain embodiments, the Fc receptor is an FcγRI, FcγRIIA, FcγRIIB, FcγRIIIA, FcγRIIIB, FcγRIV, or FcRn receptor. In some embodiments, the antibody or portion thereof binds to an immune cell, e.g., a macrophage, neutrophil, dendritic cell, B cell, natural killer cell (NKC), or eosinophil.

In some embodiments, the antibody, or portion thereof, comprising a sulfated Fc region or sulfated Fc fragment is an IgA, IgD, IgE, IgG, or IgM antibody, or portion thereof. In particular embodiments, the antibody, or portion thereof, is an IgG1, IgG2, or IgG3 antibody, or portion thereof.

In certain embodiments, the antibody, or portion thereof, comprising a sulfated Fc region or sulfated Fc fragment is a sulfated version of abciximab, adalimumab, alemtuzumab, basiliximab, bevacizumab, cetuximab, certolizumab, daclizumab, eculizumab, efalizumab, gemtuzumab, ibritumomab, infliximab, muromonab, natalizumab, omalizumab, palivizumab, panitumumab, ranibizumab, rituximab, tositumomab, or trastuzumab, or a portion thereof, comprising a sulfated Fc region or sulfated Fc fragment.

In another aspect, the invention features an antibody, or a portion thereof, comprising an immunoglobulin Fc region, or Fc fragment, comprising a sulfated glycan. In some embodiments, the antibody, or portion thereof is an isolated antibody, or portion thereof. In other embodiments, the antibody, or portion thereof, is a purified antibody, or portion thereof. In other embodiments, the antibody, or portion thereof, is a non-naturally occurring or a synthetic antibody, or portion thereof.

In certain embodiments, the sulfated glycan is linked to one or more of a CH2 immunoglobulin domain, a CH3 immunoglobulin domain, and a CH4 immunoglobulin domain of the Fc region. In particular embodiments, the sulfated glycan is linked to a CH2 domain of an IgG heavy chain. In some embodiments, the sulfated glycan is linked to one or more N-glycosylation sites of an IgA, IgD, IgE, IgG, or IgM antibody heavy chain. In yet other embodiments, the sulfated glycan is linked to Asn297 of an IgG heavy chain.

In some embodiments, the sulfated glycan comprises a branched glycan. In certain embodiments, the sulfated glycan comprises one or more of a sulfated N-acetylglucosamine, a sulfated galactose, or a sulfated N-acetylgalactosamine.

In some embodiments, the antibody, or portion thereof, is a modified antibody, or portion thereof, comprising one or more amino acid substitutions of a reference antibody, or portion thereof. In some embodiments, the modified antibody, or portion thereof, comprises a modified amino acid sequence of a reference antibody, or portion thereof, and comprises a modified glycan, wherein the reference antibody, or portion thereof, comprises an immunoglobulin Fc region, or Fc fragment, comprising a reference glycan, wherein the modified antibody, or portion thereof, comprises one or more amino acid substitutions of the Fc region, or Fc fragment, of the reference antibody, or portion thereof. In some embodiments, the one or more amino acid substitutions result in increased sulfation of the modified glycan relative to the reference glycan.

In some embodiments, at least one of the amino acids substituted is F241, F243, K246, T260, or R301 of an IgG heavy chain. In some embodiments, at least one of the amino acid substitutions is F241A, F243A, K246A, T260A, or R301A.

In some embodiments, the modified antibody, or portion thereof, comprises two or more amino acid substitutions of the Fc region, or Fc fragment, of the reference antibody, or portion thereof. In some embodiments, the two or more amino acid substitutions result in increased sulfation of the modified glycan relative to the reference glycan. In some embodiments, at least two of the amino acid substitutions are selected from F241A, F243A, K246A, T260A, and R301A. In particular embodiments, at least two of the amino acid substitutions are F241A and F243A; F241A and K246A; F241A and T260A; F241A and R301A; F243A and K246A; F243A and T260A; F243A and R301A; K246A and T260A; K246A and R301A; or T260A and R301A.

In some embodiments, the modified glycan has an altered glycan composition (e.g., an altered glycan composition described herein) relative to the reference glycan.

In some embodiments, the antibody, or portion thereof, is present in a population of antibodies, portions thereof, or both, wherein at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 40%, at least about 50%, at least about 60%, at least about 70%, at least about 80%, at least about 90%, at least about 95%, or at least about 100% of the antibodies, portions thereof, or both, of the population comprise a sulfated glycan.

In certain embodiments, the glycan is singly sulfated. In other embodiments, the glycan is doubly sulfated.

In some embodiments, the antibody, or portion thereof, comprises two Fc regions, wherein the sulfated glycan is linked to one of the Fc regions. In other embodiments, the antibody, or portion thereof, comprises two Fc regions wherein sulfated glycans are linked to both Fc regions.

In other embodiments, the antibody, or portion thereof, comprising a sulfated glycan, or the modified antibody (e.g., comprising one or more amino acid substitutions), or portion thereof, comprising a sulfated glycan, has a different, e.g., a detectably higher or lower, activity, such as an immune cell activating activity, e.g., Fc receptor affinity, Fc receptor specificity, complement activation activity, signaling activity, targeting activity, effector function, half-life, clearance, pro-inflammatory, anti-inflammatory, or transcytosis activity than a corresponding wild type or reference antibody, or portion thereof, without a sulfated glycan. In some embodiments, the effector function is antibody dependent cellular cytotoxicity, complement dependent cytotoxicity, programmed cell death, or cellular phagocytosis.

In certain embodiments, the Fc receptor is an FcγRI, FcγRIIA, FcγRIIB, FcγRIIIA, FcγRIIIB, FcγRIV, or FcRn receptor. In some embodiments, the antibody binds to an immune cell, e.g., a macrophage, neutrophil, dendritic cell, B cell, natural killer cell (NKC), or eosinophil.

In some embodiments, the antibody, or portion thereof, comprising a sulfated glycan is an IgA, IgD, IgE, IgG, or IgM antibody. In particular embodiments, the antibody, or portion thereof, is an IgG1, IgG2, or IgG3 antibody, or portion thereof.

In certain embodiments, the antibody, or portion thereof, comprising a sulfated glycan is a sulfated version of abciximab, adalimumab, alemtuzumab, basiliximab, bevacizumab, cetuximab, certolizumab, daclizumab, eculizumab, efalizumab, gemtuzumab, ibritumomab, infliximab, muromonab, natalizumab, omalizumab, palivizumab, panitumumab, ranibizumab, rituximab, tositumomab, or trastuzumab, or a portion thereof, comprising a sulfated glycan.

In yet other embodiments, the antibody, or portion thereof, comprising a sulfated glycan is conjugated to a heterologous moiety. In some embodiments, the heterologous moiety is a polypeptide, nucleic acid, or small molecule. In particular embodiments, the antibody, or portion thereof, conjugated to a heterologous moiety is a sulfated version of alefacept, abatacept, etanercept, rilonacept, or denileukin diftitox, or portion thereof, comprising a sulfated glycan.

In another aspect, the invention features an IgG molecule, or portion thereof, comprising a sulfated N-linked glycan at Asn297 of the CH2 domain. In some embodiments, the IgG molecule, or portion thereof, is an isolated IgG molecule, or portion thereof. In other embodiments, the IgG molecule, or portion thereof, is a purified IgG molecule, or portion thereof. In other embodiments, the IgG molecule, or portion thereof, is a non-naturally occurring or a synthetic IgG molecule, or portion thereof.

In some embodiments, the sulfated glycan comprises a branched glycan. In certain embodiments, the sulfated glycan comprises one or more of a sulfated N-acetylglucosamine, a sulfated galactose, or a sulfated N-acetylgalactosamine.

In some embodiments, the IgG molecule, or portion thereof, is a modified IgG molecule, or portion thereof, comprising one or more amino acid substitutions of a reference IgG molecule, or portion thereof. In some embodiments, the modified IgG molecule, or portion thereof, comprises a modified amino acid sequence of a reference IgG molecule, or portion thereof, and comprises a modified glycan, wherein the reference IgG molecule, or portion thereof, comprises an immunoglobulin Fc region, or Fc fragment, comprising a reference glycan, wherein the modified IgG molecule, or portion thereof, comprises one or more amino acid substitutions of the Fc region, or Fc fragment, of the reference IgG molecule, or portion thereof. In some embodiments, the one or more amino acid substitutions result in increased sulfation of the modified glycan relative to the reference glycan.

In some embodiments, at least one of the amino acids substituted is F241, F243, K246, T260, or R301 of an IgG heavy chain. In some embodiments, at least one of the amino acid substitutions is F241A, F243A, K246A, T260A, or R301A.

In some embodiments, the modified IgG molecule, or portion thereof, comprises two or more amino acid substitutions of the Fc region, or Fc fragment, of the reference IgG molecule, or portion thereof. In some embodiments, the two or more amino acid substitutions result in increased sulfation of the modified glycan relative to the reference glycan. In some embodiments, at least two of the amino acid substitutions are selected from F241A, F243A, K246A, T260A, and R301A. In particular embodiments, at least two of the amino acid substitutions are F241A and F243A; F241A and K246A; F241A and T260A; F241A and R301A; F243A and K246A; F243A and T260A; F243A and R301A; K246A and T260A; K246A and R301A; or T260A and R301A.

In some embodiments, the modified glycan has an altered glycan composition (e.g., an altered glycan composition described herein) relative to the reference glycan.

In some embodiments, the IgG molecule, or portion thereof, is present in a population of IgG molecules, portions thereof, or both, wherein at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 40%, at least about 50%, at least about 60%, at least about 70%, at least about 80%, at least about 90%, at least about 95%, or at least about 100% of the IgG molecules, portions thereof, or both, comprise a sulfated glycan.

In certain embodiments, the glycan is singly sulfated. In other embodiments, the glycan is doubly sulfated.

In some embodiments, the IgG molecule, or portion thereof, comprises two CH2 domains, wherein the sulfated glycan is linked to one of the CH2 domains. In other embodiments, the IgG molecule, or portion thereof, comprises two CH2 domains, wherein sulfated glycans are linked to both CH2 domains.

In other embodiments, the IgG molecule, or portion thereof, comprising a sulfated glycan, or the modified IgG molecule (e.g., comprising one or more amino acid substitutions), or portion thereof, comprising a sulfated glycan, has a different, e.g., a detectably higher or lower, activity, such as an immune cell activating activity, e.g., Fc receptor affinity, Fc receptor specificity, complement activation activity, signaling activity, targeting activity, effector function, half-life, clearance, pro-inflammatory, anti-inflammatory, or transcytosis activity than a corresponding wild type or reference IgG molecule, or portion thereof, without a sulfated glycan. In some embodiments, the effector function is antibody dependent cellular cytotoxicity, complement dependent cytotoxicity, programmed cell death, or cellular phagocytosis.

In certain embodiments, the Fc receptor is an FcγRI, FcγRIIA, FcγRIIB, FcγRIIIA, FcγRIIIB, FcγRIV, or FcRn receptor. In some embodiments, the IgG molecule, or portion thereof, binds to an immune cell, e.g., a macrophage, neutrophil, dendritic cell, B cell, natural killer cell (NKC), or eosinophil.

In some embodiments, the IgG molecule, or portion thereof, comprising a sulfated glycan is an IgG1, IgG2, or IgG3 antibody, or portion thereof.

In certain embodiments, the IgG molecule, or portion thereof, comprising a sulfated glycan is a sulfated version of abciximab, adalimumab, alemtuzumab, basiliximab, bevacizumab, cetuximab, certolizumab, daclizumab, eculizumab, efalizumab, gemtuzumab, ibritumomab, infliximab, muromonab, natalizumab, omalizumab, palivizumab, panitumumab, ranibizumab, rituximab, tositumomab, or trastuzumab, or portion thereof, comprising a sulfated glycan.

In yet other embodiments, the IgG molecule, or portion thereof, comprising a sulfated glycan is conjugated to a heterologous moiety. In some embodiments, the heterologous moiety is a polypeptide, nucleic acid, or small molecule.

In another aspect, the invention features a sulfated version of abciximab comprising a sulfated Fc region or sulfated Fc fragment, a sulfated version of adalimumab comprising a sulfated Fc region or sulfated Fc fragment, a sulfated version of alemtuzumab comprising a sulfated Fc region or sulfated Fc fragment, a sulfated version of basiliximab comprising a sulfated Fc region or sulfated Fc fragment, a sulfated version of bevacizumab comprising a sulfated Fc region or sulfated Fc fragment, a sulfated version of cetuximab comprising a sulfated Fc region or sulfated Fc fragment, a sulfated version of certolizumab comprising a sulfated Fc region or sulfated Fc fragment, a sulfated version of daclizumab comprising a sulfated Fc region or sulfated Fc fragment, a sulfated version of eculizumab comprising a sulfated Fc region or sulfated Fc fragment, a sulfated version of efalizumab comprising a sulfated Fc region or sulfated Fc fragment, a sulfated version of gemtuzumab comprising a sulfated Fc region or sulfated Fc fragment, a sulfated version of ibritumomab comprising a sulfated Fc region or sulfated Fc fragment, a sulfated version of infliximab comprising a sulfated Fc region or sulfated Fc fragment, a sulfated version of muromonab comprising a sulfated Fc region or sulfated Fc fragment, a sulfated version of natalizumab comprising a sulfated Fc region or sulfated Fc fragment, a sulfated version of omalizumab comprising a sulfated Fc region or sulfated Fc fragment, a sulfated version of palivizumab comprising a sulfated Fc region or sulfated Fc fragment, a sulfated version of panitumumab comprising a sulfated Fc region or sulfated Fc fragment, a sulfated version of ranibizumab comprising a sulfated Fc region or sulfated Fc fragment, a sulfated version of rituximab comprising a sulfated Fc region or sulfated Fc fragment, a sulfated version of tositumomab comprising a sulfated Fc region or sulfated Fc fragment, or a sulfated version of trastuzumab comprising a sulfated Fc region or sulfated Fc fragment.

In another aspect, the invention features a sulfated version of abciximab comprising a sulfated glycan, a sulfated version of adalimumab comprising a sulfated glycan, a sulfated version of alemtuzumab comprising a sulfated glycan, a sulfated version of basiliximab comprising a sulfated glycan, a sulfated version of bevacizumab comprising a sulfated glycan, a sulfated version of cetuximab comprising a sulfated glycan, a sulfated version of certolizumab comprising a sulfated glycan, a sulfated version of daclizumab comprising a sulfated glycan, a sulfated version of eculizumab comprising a sulfated glycan, a sulfated version of efalizumab comprising a sulfated glycan, a sulfated version of gemtuzumab comprising a sulfated glycan, a sulfated version of ibritumomab comprising a sulfated glycan, a sulfated version of infliximab comprising a sulfated glycan, a sulfated version of muromonab comprising a sulfated glycan, a sulfated version of natalizumab comprising a sulfated glycan, a sulfated version of omalizumab comprising a sulfated glycan, a sulfated version of palivizumab comprising a sulfated glycan, a sulfated version of panitumumab comprising a sulfated glycan, a sulfated version of ranibizumab comprising a sulfated glycan, a sulfated version of rituximab comprising a sulfated glycan, a sulfated version of tositumomab comprising a sulfated glycan, or a sulfated version of trastuzumab comprising a sulfated glycan.

In another aspect, the invention features a sulfated version of alefacept comprising a sulfated Fc region or sulfated Fc fragment, a sulfated version of abatacept comprising a sulfated Fc region or sulfated Fc fragment, a sulfated version of etanercept comprising a sulfated Fc region or sulfated Fc fragment, a sulfated version of rilonacept comprising a sulfated Fc region or sulfated Fc fragment, or a sulfated version of denileukin diftitox comprising a sulfated Fc region or sulfated Fc fragment.

In another aspect, the invention features a sulfated version of alefacept comprising a sulfated glycan, a sulfated version of abatacept comprising a sulfated glycan, a sulfated version of etanercept comprising a sulfated glycan, a sulfated version of rilonacept comprising a sulfated glycan, or a sulfated version of denileukin diftitox comprising a sulfated glycan.

In another aspect, the invention features a population of glycoproteins, wherein at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 40%, at least about 50%, at least about 60%, at least about 70%, at least about 80%, at least about 90%, at least about 95%, or at least about 100% of the glycoproteins comprise a sulfated Fc region, a sulfated Fc fragment, and/or a sulfated glycan.

In yet another aspect, the invention features a glycoprotein comprising one or more of the amino acid sequence of SEQ ID NO:1, 2, 3, 4, or 5, or a portion or variant thereof. In some embodiments, the glycoprotein comprises one or more sulfated Fc regions, one or more sulfated Fc fragments, and/or one or more sulfated glycans.

BRIEF DESCRIPTION OF THE DRAWINGS

The present teachings described herein will be more fully understood from the following description of various illustrative embodiments, when read together with the accompanying drawings. It should be understood that the drawings described below are for illustration purposes only and are not intended to limit the scope of the present teachings in any way.

DETAILED DESCRIPTION

Figure 1:
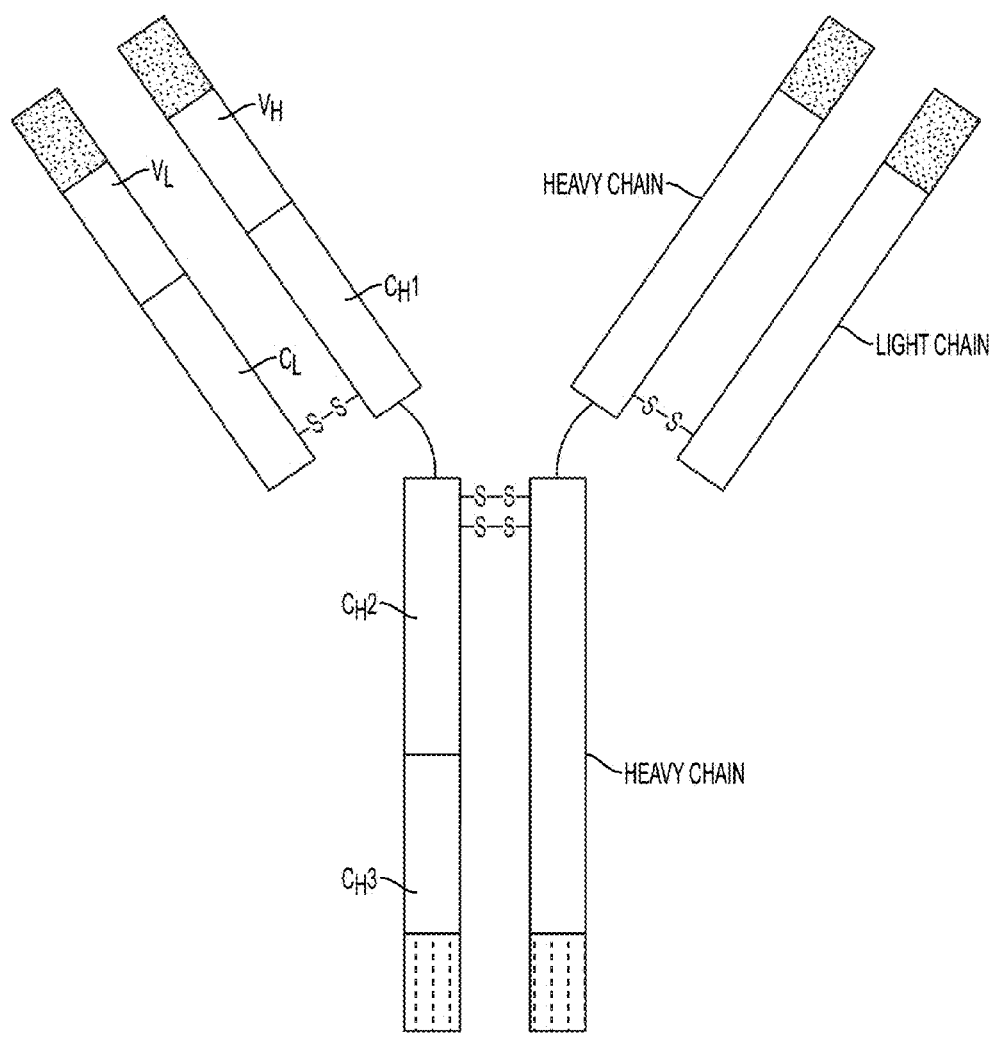
FIG. 1 is a schematic illustration of an IgG antibody molecule.

The constant regions (Fc regions) of antibodies interact with cellular binding partners to mediate antibody function and activity, such as antibody-dependent effector functions and complement activation. For IgG type antibodies, binding sites for complement C1q and Fc receptors (FcγRs) are located in the CH2 domain of the Fc region.

Coexpression of activating and inhibitory FcRs on different target cells modulates antibody-mediated immune responses. In addition to their involvement in the efferent phase of an immune response, FcRs are also important for regulating B cell and dendritic cell (DC) activation. For example, in the case of IgG type antibodies, different classes of FcγR mediate various cellular responses, such as phagocytosis by macrophages, antibody-dependent cell-mediated cytotoxicity by NK cells, and degranulation of mast cells. Each FcγR displays different binding affinities and IgG subclass specificities. Lectin receptors also play a role. For example, Dc-SIGN has been shown to play a role in the anti-inflammatory activity of Fc, e.g., in IVIG (see, e.g., WO2008057634; WO2009132130).

Antibodies are glycosylated at conserved positions in the constant regions of their heavy chain. For example, IgG antibodies have a single N-linked glycosylation site at Asn297 of the CH2 domain. Each antibody isotype has a distinct variety of N-linked carbohydrate structures in the constant regions. For human IgG, core oligosaccharides normally consists of GlcNAc$_2$Man$_3$GlcNAc, with differing numbers of outer residues. Variation among individual IgG's can occur via attachment of galactose and/or galactose-sialic acid at two terminal GlcNAc or via attachment of a third GlcNAc arm (bisecting GlcNAc). Sulfation at this glycosylation site has not previously been reported.

The inventors have discovered that sulfation at the CH2 glycosylation site has effects on antibody function and/or activity, e.g., on one or more of: Fc receptor binding, Fc receptor affinity, Fc receptor specificity, complement activation, signaling activity, targeting activity, effector function (such as programmed cell death or cellular phagocytosis), half-life, clearance, and transcytosis. Described herein are glycoproteins (e.g., IVIG, antibodies or fusion proteins, such as Fc fusion proteins) that include a sulfated constant region of an immunoglobulin, and have an altered activity and/or function relative to unsulfated glycoproteins. Methods of making and using such compositions are also described.

Definitions

As used herein, "glycan" is a sugar, which can be a monomer or a polymer of sugar residues, such as at least three sugars, and can be linear or branched. A "glycan" can include natural sugar residues (e.g., glucose, N-acetylglucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6'sulfo N-acetylglucosamine, etc.). The term "glycan" includes homo and heteropolymers of sugar residues. The term "glycan" also encompasses a glycan component of a glycoconjugate (e.g., of a glycoprotein, glycolipid, proteoglycan, etc.). The term also encompasses free glycans, including glycans that have been cleaved or otherwise released from a glycoconjugate.

As used herein, the term "glycoprotein" refers to a protein that contains a peptide backbone covalently linked to one or more sugar moieties (i.e., glycans). Sugar moiety(ies) may be in the form of monosaccharides, disaccharides, oligosaccharides, and/or polysaccharides. Sugar moiety(ies) may comprise a single unbranched chain of sugar residues or may comprise one or more branched chains. Glycoproteins can contain O-linked sugar moieties and/or N-linked sugar moieties.

By "purified" (or "isolated") refers to a nucleic acid sequence (e.g., a polynucleotide) or an amino acid sequence (e.g., a polypeptide) that is removed or separated from other components present in its natural environment. For example, an isolated polypeptide is one that is separated from other components of a cell in which it was produced (e.g., the endoplasmic reticulum or cytoplasmic proteins and RNA). An isolated polynucleotide is one that is separated from other nuclear components (e.g., histones) and/or from upstream or downstream nucleic acid sequences. An isolated nucleic acid sequence or amino acid sequence can be at least 60% free, or at least 75% free, or at least 90% free, or at least 95% free from other components present in natural environment of the indicated nucleic acid sequence or amino acid sequence.

As used herein, "polynucleotide" (or "nucleotide sequence" or "nucleic acid molecule") refers to an oligonucleotide, nucleotide, or polynucleotide, and fragments or portions thereof, and to DNA or RNA of genomic or synthetic origin, which may be single- or double-stranded, and represent the sense or anti-sense strand.

As used herein, "polypeptide" (or "amino acid sequence" or "protein") refers to an oligopeptide, peptide, polypeptide, or protein sequence, and fragments or portions thereof, and to naturally occurring or synthetic molecules. "Amino acid sequence" and like terms, such as "polypeptide" or "protein", are not meant to limit the indicated amino acid sequence to the complete, native amino acid sequence associated with the recited protein molecule.

The articles "a" and "an" are used herein to refer to one or to more than one (i.e., to at least one) of the grammatical object of the article. By way of example, "an element" means one element or more than one element.

The term "about" is used herein to mean a value – or +20% of a given numerical value. Thus, "about 60%" means a value of between 60-(20% of 60) and 60+(20% of 60) (i.e., between 48 and 70).

The term "pharmaceutically effective amount" or "therapeutically effective amount" refers to an amount (e.g., dose) effective in treating a patient, having a disorder or condition described herein. It is also to be understood herein that a "pharmaceutically effective amount" may be interpreted as an amount giving a desired therapeutic effect, either taken in one dose or in any dosage or route, taken alone or in combination with other therapeutic agents.

The term "treatment" or "treating", as used herein, refers to administering a therapy in an amount, manner, and/or mode effective to improve a condition, symptom, or parameter associated with a disorder or condition or to prevent or reduce progression of a disorder or condition, to a degree detectable to one skilled in the art. An effective amount, manner, or mode can vary depending on the subject and may be tailored to the subject.

The term "subject", as used herein, means any subject for whom diagnosis, prognosis, or therapy is desired. For example, a subject can be a mammal, e.g., a human or non-human primate (such as an ape, monkey, orangutan, or chimpanzee), a dog, cat, guinea pig, rabbit, rat, mouse, horse, cattle, or cow.

As used herein, the term "antibody" refers to a polypeptide that includes at least one immunoglobulin variable region, e.g., an amino acid sequence that provides an immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab, F(ab')$_2$, Fd, Fv, and dAb fragments) as well as complete antibodies, e.g., intact immunoglobulins of types IgA, IgG, IgE, IgD, IgM (as well as subtypes thereof). Light chains of the immunoglobulin can be of types kappa or lambda.

As used herein, the term "constant region" refers to a polypeptide that corresponds to, or is derived from, one or more constant region immunoglobulin domains of an antibody. A constant region can include any or all of the following immunoglobulin domains: a CH1 domain, a hinge region, a CH2 domain, a CH3 domain (derived from an IgA, IgD, IgG, IgE, or IgM), and a CH4 domain (derived from an IgE or IgM).

As used herein, the term "Fc region" refers to a polypeptide comprising a constant region of an antibody excluding the first constant region immunoglobulin domain. "Fc region" refers to the last two constant region immunoglobulin domains of IgA, IgD, and IgG, and the last three constant region immunoglobulin domains of IgE and IgM, and may also include part or all of the flexible hinge N-terminal to these domains. For IgG, "Fc region" comprises immunoglobulin domains Cgamma2 (Cγ2) and Cgamma3 (Cγ3) and the lower part of the hinge between Cgamma1 (Cγ1) and Cγ2. Although the boundaries of the Fc region may vary, the human IgG heavy chain Fc region is usually defined to comprise residues starting at T223 or C226 or P230, to its carboxyl-terminus, wherein the numbering is according to the EU index as in Kabat et al. (1991, NIH Publication 91-3242, National Technical Information Services, Spring-field, Va.). For IgA, Fc region comprises immunoglobulin domains Calpha2 (Cα2) and Calpha3 (Cα3) and the lower part of the hinge between Calpha1 (Cα1) and Cα2.

As used herein, the term "Fc region variant" refers to an analog of an Fc region that possesses one or more Fc-mediated activities described herein. This term includes Fc regions comprising one or more amino acid modifications relative to a wild type or naturally existing Fc region. For example, variant Fc regions can possess at least about 50% homology, at least about 75% homology, at least about 80% homology, at least about 85%, homology, at least about 90% homology, at least about 95% homology, or more, with a naturally existing Fc region. Fc region variants also include Fc regions comprising one or more amino acid residues added to or deleted from the N- or C-terminus of a wild type Fc region.

As used herein, an "N-glycosylation site of an Fc region" refers to an amino acid residue within an Fc region to which a glycan is N-linked.

As used herein, the terms "coupled", "linked", "joined", "fused", and "fusion" are used interchangeably. These terms refer to the joining together of two more elements or components by whatever means, including chemical conjugation or recombinant means.

The terms "overexpress," "overexpression" or "overexpressed" interchangeably refer to a protein or nucleic acid that is transcribed or translated at a detectably greater level, such as in a cancer cell, in comparison to a control cell. The term includes expression due to transcription, post transcriptional processing, translation, post-translational processing, cellular localization (e.g., organelle, cytoplasm, nucleus, cell surface), and RNA and protein stability, as compared to a control cell. Overexpression can be detected using conventional techniques, e.g., for detecting mRNA (i.e., RT-PCR, PCR, hybridization) or proteins (i.e., ELISA, immunohistochemical techniques). Overexpression can be expression in an amount greater than about 10%, 20%, 30%, 40%, 50%, 60%, 70%, 80%, 90% or more compared to a control cell. In certain instances, overexpression is 1-fold, 2-fold, 3-fold, 4-fold, or more, higher level of transcription or translation compared to a control cell.

I. Glycoproteins

As described herein, antibodies have been sulfated at N-glycosylation sites to affect specific binding to Fc receptors and to affect antibody effector function. Accordingly, glycoproteins are described herein that include an immunoglobulin Fc region, wherein the N-linked glycosylation site in the Fc region contains a sulfate moiety, e.g., a non-naturally occurring sulfate moiety. In one instance, a glycoprotein that includes an Fc region (e.g., a glycoprotein that includes a CH2 domain of an Fc region of an antibody heavy chain) can be sulfated using methods disclosed herein to modify antibody-mediated functions, such as Fc-mediated effector functions. Further, the particular modification (i.e., increased or decreased effector function) can be controlled by controlling sulfation pattern. Such methods can be used, for example, to modulate one or more activity, such as one or more therapeutic activity, of a glycoprotein.

Glycoproteins include, for example, any of a variety of hematologic agents (including, for instance, erythropoietin, blood-clotting factors, etc.), interferons, colony stimulating factors, antibodies, enzymes, and hormones. The identity of a particular glycoprotein is not intended to limit the present disclosure, and any glycoprotein of interest can be sulfated using methods described herein.

In addition to an Fc region or fragment thereof having a sulfated glycan, a glycoprotein described herein can also include a target-binding domain that binds to a target of interest (e.g., binds to an antigen). For example, a glycoprotein, such as an antibody, can bind to a transmembrane polypeptide (e.g., receptor) or ligand (e.g., a growth factor). Exemplary molecular targets (e.g., antigens) for glycoproteins described herein (e.g., antibodies) include CD proteins such as CD2, CD3, CD4, CD8, CD11, CD19, CD20, CD22, CD25, CD33, CD34, CD40, CD52; members of the ErbB receptor family such as the EGF receptor (EGFR, HER1, ErbB1), HER2 (ErbB2), HER3 (ErbB3) or HER4 (ErbB4) receptor; macrophage receptors such as CRIg; tumor necrosis factors such as TNFα or TRAIL/Apo-2; cell adhesion molecules such as LFA-1, Mac1, p150,95, VLA-4, ICAM-1, VCAM and αvβ integrin including either α or β subunits thereof (e.g., anti-CD11a, anti-CD18 or anti-CD1 lb antibodies); growth factors and receptors such as EGF, FGFR (e.g., FGFR3) and VEGF; IgE; cytokines such as IL1; cytokine receptors such as IL2 receptor; blood group antigens; flk2/flt3 receptor; obesity (OB) receptor; mpl receptor; CTLA-4; protein C; neutropilins; ephrins and receptors; netrins and receptors; slit and receptors; chemokines and chemokine receptors such as CCL5, CCR4, CCR5; amyloid beta; complement factors, such as complement factor D; lipoproteins, such as oxidized LDL (oxLDL); lymphotoxins, such as lymphotoxin alpha (LTa). Other molecular targets include Tweak, B7RP-1, proprotein convertase subtilisin/kexin type 9 (PCSK9), sclerostin, c-kit, Tie-2, c-fms, and anti-M1.

Nonlimiting, exemplary glycoproteins that include an Fc region of an antibody heavy chain and that can be sulfated according to methods described herein include abatacept (Orencia®, Bristol-Myers Squibb), abciximab (ReoPro®, Roche), adalimumab (Humira®, Bristol-Myers Squibb), alefacept (Amevive®, Astellas Pharma), alemtuzumab (Campath®, Genzyme/Bayer), basiliximab (Simulect®, Novartis), bevacizumab (Avastin®, Roche), certolizumab (CIMZIA®, UCB, Brussels, Belgium), cetuximab (Erbitux®, Merck-Serono), daclizumab (Zenapax®, Hoffmann-La Roche), denileukin diftitox (Ontak®, Eisai), eculizumab (Soliris®, Alexion Pharmaceuticals), efalizumab (Raptiva®, Genentech), etanercept (Enbrel®, Amgen-Pfizer), gemtuzumab (Mylotarg®, Pfizer), ibritumomab (Zevalin®, Spectrum Pharmaceuticals), infliximab (Remicade®, Centocor), muromonab (Orthoclone OKT3®, Janssen-Cilag), natalizumab (Tysabri®, Biogen Idec, Elan), omalizumab (Xolair®, Novartis), palivizumab (Synagis®, MedImmune), panitumumab (Vectibix®, Amgen), ranibizumab (Lucentis®, Genentech), rilonacept (Arcalyst®, Regeneron Pharmaceuticals), rituximab (MabThera®, Roche), tositumomab (Bexxar®, GlaxoSmithKline), and trastuzumab (Herceptin®, Roche).

A. N-Linked Glycosylation

N-linked oligosaccharide chains are added to a protein in the lumen of the endoplasmic reticulum (see Molecular Biology of the Cell, Garland Publishing, Inc. (Alberts et al., 1994)). Specifically, an initial oligosaccharide (typically 14-sugar) is added to the amino group on the side chain of an asparagine residue contained within the target consensus sequence of Asn-X-Ser/Thr, where X may be any amino acid except proline. The structure of this initial oligosaccharide is common to most eukaryotes, and contains 3 glucose, 9 mannose, and 2 N-acetylglucosamine residues. This initial oligosaccharide chain can be trimmed by specific glycosidase enzymes in the endoplasmic reticulum, resulting in a short, branched core oligosaccharide composed of two N-acetylglucosamine and three mannose residues.

N-glycans can be subdivided into three distinct groups called "high mannose type", "hybrid type", and "complex type", with a common pentasaccharide core (Man (alpha1, 6)-(Man(alpha1,3))-Man(beta1,4)-GlcpNAc(beta1,4)-Glcp-NAc(beta 1,N)-Asn) occurring in all three groups.

After initial processing in the endoplasmic reticulum, the glycoprotein is transported to the Golgi where further processing may take place. If the glycan is transferred to the Golgi before it is completely trimmed to the core pentasaccharide structure, it results in a "high-mannose glycan".

Additionally or alternatively, one or more monosaccharides units of N-acetylglucosamine may be added to core mannose subunits to form a "complex glycan". Galactose may be added to N-acetylglucosamine subunits, and sialic acid subunits may be added to galactose subunits, resulting in chains that terminate with any of a sialic acid, a galactose or an N-acetylglucosamine residue. Additionally, a fucose residue may be added to an N-acetylglucosamine residue of the core oligosaccharide. Each of these additions is catalyzed by specific glycosyl transferases, known in the art.

"Hybrid glycans" comprise characteristics of both high-mannose and complex glycans. For example, one branch of a hybrid glycan may comprise primarily or exclusively mannose residues, while another branch may comprise N-acetylglucosamine, sialic acid, galactose, and/or fucose sugars.

N-Linked Glycosylation in Antibodies

Antibodies are glycosylated at conserved, N-linked glycosylation sites in constant regions of immunoglobulin heavy chains. For example, IgG antibodies have a single N-linked glycosylation site at Asn297 of the CH2 domain (see Jefferis, Nature Reviews 8:226-234 (2009)). IgA antibodies have N-linked glycosylation sites within the CH2 and CH3 domains, IgE antibodies have N-linked glycosylation sites within the CH3 domain, and IgM antibodies have N-linked glycosylation sites within the CH1, CH2, CH3, and CH4 domains (see Arnold et al., J. Biol. Chem. 280:29080-29087 (2005); Mattu et al., J. Biol. Chem. 273:2260-2272 (1998); Nettleton et al., Int. Arch. Allergy Immunol. 107: 328-329 (1995)).

Each antibody isotype has a distinct variety of N-linked carbohydrate structures in the constant regions. For example, IgG has a single N-linked biantennary carbohydrate at Asn297 of the CH2 domain in the Fc region, which also contains binding sites for C1q and FcγR (see Jefferis et al., Immunol. Rev. 163:59-76 (1998); and Wright et al., Trends Biotech 15:26-32 (1997)). For human IgG, a core oligosaccharide normally consists of $GlcNAc_2Man_3GlcNAc_2$, with differing numbers of outer residues. Variation among individual IgG can occur via attachment of galactose and/or galactose-sialic acid at two terminal GlcNAc or via attachment of a third GlcNAc arm (bisecting GlcNAc). Although accounting for only 2-3% of antibody mass, glycosylation of IgG-Fc has been shown to be important for effector functions.

B. Antibodies

The basic structure of an IgG antibody is illustrated in FIG. 1. As shown in FIG. 1, an IgG antibody consists of two identical light polypeptide chains and two identical heavy polypeptide chains linked together by disulphide bonds. The first domain located at the amino terminus of each chain is variable in amino acid sequence, providing antibody binding specificities found in each individual antibody. These are known as variable heavy (VH) and variable light (VL) regions. The other domains of each chain are relatively invariant in amino acid sequence and are known as constant heavy (CH) and constant light (CL) regions. As shown in FIG. 1, for an IgG antibody, the light chain includes one variable region (VL) and one constant region (CL). An IgG heavy chain includes a variable region (VH), a first constant region (CH1), a hinge region, a second constant region (CH2), and a third constant region (CH3). In IgE and IgM antibodies, the heavy chain includes an additional constant region (CH4).

Antibodies described herein can include, for example, monoclonal antibodies, polyclonal antibodies, multispecific antibodies, human antibodies, humanized antibodies, camelized antibodies, chimeric antibodies, single-chain Fvs (scFv), disulfide-linked Fvs (sdFv), and anti-idiotypic (anti-Id) antibodies, and antigen-binding fragments of any of the above. Antibodies can be of any type (e.g., IgG, IgE, IgM, IgD, IgA and IgY), class (e.g., IgG1, IgG2, IgG3, IgG4, IgA1 and IgA2) or subclass.

The term "Fc fragment", as used herein, refers to one or more fragments of an Fc region that retains an Fc function and/or activity described herein, such as binding to an Fc receptor. Examples of such fragments include fragments that include an N-linked glycosylation site of an Fc region (e.g., an Asn297 of an IgG heavy chain or homologous sites of other antibody isotypes), such as a CH2 domain. The term "antigen binding fragment" of an antibody, as used herein, refers to one or more fragments of an antibody that retain the ability to specifically bind to an antigen. Examples of binding fragments encompassed within the term "antigen binding fragment" of an antibody include a Fab fragment, a F(ab')$_2$ fragment, a Fd fragment, a Fv fragment, a scFv fragment, a dAb fragment (Ward et al., (1989) Nature 341:544-546), and an isolated complementarity determining region (CDR). These antibody fragments can be obtained using conventional techniques known to those with skill in the art, and fragments can be screened for utility in the same manner as are intact antibodies.

Antibodies or fragments (e.g., wild type or reference antibodies or fragments to be sulfated as described herein) can be produced by any method known in the art for synthesizing antibodies (see, e.g., Harlow et al., Antibodies: A Laboratory Manual, (Cold Spring Harbor Laboratory Press, 2nd ed. 1988); Brinkman et al., 1995, J. Immunol. Methods 182:41-50; WO 92/22324; WO 98/46645). Chimeric antibodies can be produced using methods described in, e.g., Morrison, 1985, Science 229:1202, and humanized antibodies by methods described in, e.g., U.S. Pat. No. 6,180,370.

Additional antibodies of compositions and methods described herein are bispecific antibodies and multivalent antibodies, as described in, e.g., Segal et al., J. Immunol. Methods 248:1-6 (2001); and Tutt et al., J. Immunol. 147: 60 (1991).

C. Amino Acid Modifications of the Fc Region

The amino acid sequence of a glycoprotein described herein can be modified to produce an Fc region variant, such as an Fc region having at least one (e.g., 1, 2, 3, 4, 5, 6, 7, 8, 9, 10, or more) addition, substitution, or deletion of a wild-type amino acid residue. Amino acid residue(s) to be modified can be one or more amino acid residue(s) involved in or proximate to an interaction of an Fc region and a glycan, and/or involved in an effector function described herein. For example, crystal structures for Fc dimers with glycans bound to FcγRIII are known (see, e.g., Mizushima et al., Genes to Cells 16:1071-1080 (2011); Ferrara et al., PNAS 108:12669-12674 (2011)). Accordingly, one or more amino acids of the Fc region near or proximal to a bound glycan (e.g., an Fc region amino acid putatively involved in hydrogen bonding and/or Van Der Waals forces with a glycan) can be modified.

Specific, nonlimiting amino acid residues that can be modified include, e.g., F241, F243, K246, T260, Y296, S298, and R301 (Kabat numbering) of an IgG1 immunoglobulin heavy chain, or corresponding amino acid residues of other immunoglobulins. These amino acid residues can be substituted with any amino acid or amino acid analog. For example, substitutions at the recited positions can be made with any naturally-occurring amino acid (e.g., alanine, aspartic acid, asparagine, arginine, cysteine, glycine, glutamic acid, glutamine, histidine, leucine, valine, isoleucine, lysine, methionine, proline, threonine, serine, phenylalanine, tryptophan, or tyrosine). In particular instances, an amino acid residue is substituted with alanine.

Glycoproteins described herein can include additional modifications of Fc regions. For example, binding sites on human and murine antibodies for FcγR have been mapped to the "lower hinge region" consisting of residues 233-239 (EU index numbering as in Kabat et al., Sequences of Proteins of Immunological Interest, 5th Ed. Public Health Service, National Institutes of Health, Bethesda, Md. (1991); see Woof et al., Molec. Immunol. 23:319-330 (1986); Duncan et al., Nature 332:563 (1988)). Accordingly, an Fc region variant can include a modification of one or more of amino acids 233-239. Other amino acids that can be modified include G316-K338; K274-R301; and Y407-R416 (Shields et al., J. Biol. Chem. 9:6591-6604 (2001)).

Additionally, a number of different Fc region amino acids that may comprise a binding site for C1q have been identified. These include residues 231-238, 318, 320, 322, and 331 (Kabat numbering) (see, e.g., U.S. Pat. No. 6,194,551; WO 99/51642; Idusogie et al., J. Immunol. 164:4178-4184 (2000). Thus, an Fc region variant can include a modification of one or more of these amino acids (e.g., a modification of 1, 2, 3, 4, 5, 6, 7, 8, 9, 10, or more of these amino acids).

Glycoproteins having one or more amino acid residue modifications described herein can be produced according to molecular biology and recombinant gene expression methods known in the art and described herein.

D. Glycan Modifications

IgG1 glycosylation typically includes complex type N-glycans with variable galactosylation and low levels of sialylation, as well as low levels of high mannose and hybrid glycans. The lack of complexity can be, in part, the result of steric hindrance, which may limit access of some glycosyltransferase enzymes. While not wishing to be bound by theory, it is believed that the introduction of certain amino acid modifications to a glycoprotein, such as amino acid modifications described herein, may relieve the hydrogen bonding and Van Der Waals forces between the glycans of the glycoprotein and the backbone amino acids, resulting in the ability to produce modifications to glycan composition during protein expression, e.g., by a host cell expressing the glycoprotein, and/or by post-production, in vitro methods.

In some instances, glycoproteins modified by one or more amino acid residues described herein have modified glycan compositions relative to corresponding wild type or reference glycoproteins. For example, in the case of IgG antibodies, a mutated glycoprotein described herein can have altered (e.g., increased or decreased) levels of mannose, N-acetylglucosamine, sialic acid, galactose, and/or fucose sugars, relative to a corresponding wild type or reference IgG antibody. Altered levels can be measured on an individual glycan (e.g., an increase or decrease in the number or type of sugars on a particular glycan), or the overall composition of a preparation of glycoproteins can be modified (e.g., a higher or lower number or percentage of a preparation of modified glycoproteins can have a particular glycan composition relative to a corresponding wild type or reference glycoprotein).

In some embodiments, glycoproteins modified by one or more amino acid residues described herein are transfected and expressed in a host cell, wherein endogenous cellular glycosylation machinery of the host cell produces a glycoprotein having modified glycans relative to a corresponding wild type or reference glycoprotein expressed under the same conditions in the same host cell.

In other embodiments, glycoproteins modified by one or more amino acid residues described herein are transfected and expressed in a host cell engineered to express one or more exogenous glycosylation enzymes, e.g., one or more glycosyltransferase, e.g., one or more glycosyltransferase described herein, wherein cellular glycosylation machinery of the engineered host cell produces a glycoprotein having modified glycans relative to a corresponding wild type or reference glycoprotein expressed under the same conditions in the same engineered host cell.

In yet other embodiments, glycoproteins modified by one or more amino acid residues described herein are transfected and expressed in a host cell engineered to over-express or under-express one or more endogenous glycosylation enzymes, e.g., one or more glycosyltransferase, e.g., one or more glycosyltransferase described herein, wherein cellular glycosylation machinery of the engineered host cell produces a glycoprotein having modified glycans relative to a corresponding wild type or reference glycoprotein expressed under the same conditions in the same engineered host cell.

In other embodiments, glycoproteins modified by one or more amino acid residues described herein are expressed in a host cell and purified from the host cell, and purified glycoproteins are modified, e.g., enzymatically modified in-vitro with one or more glycosylation enzymes, e.g., one or more glycosyltransferases, e.g., one or more glycosyltransferases disclosed herein, to produce glycoproteins having modified glycans relative to corresponding wild type or reference glycoproteins expressed under the same conditions in the same host cell.

E. Glycoprotein Conjugates

The disclosure includes sulfated glycoproteins (or Fc regions or Fc fragments containing a sulfated N-glycosylation site thereof) that are conjugated or fused to one or more heterologous moieties. Sulfation of such glycoprotein conjugates modifies one or more Fc-mediated functions described herein. Heterologous moieties include, but are not limited to, peptides, polypeptides, proteins, fusion proteins, nucleic acid molecules, small molecules, mimetic agents, synthetic drugs, inorganic molecules, and organic molecules. In some instances, methods described herein sulfate a fusion protein that comprises a peptide, polypeptide, protein scaffold, scFv, dsFv, diabody, Tandab, or an antibody mimetic fused to an Fc region, such as a glycosylated Fc region. A fusion protein can include a linker region connecting an Fc region to a heterologous moiety (see, e.g., Hallewell et al. (1989), J. Biol. Chem. 264, 5260-5268; Alfthan et al. (1995), Protein Eng. 8, 725-731; Robinson & Sauer (1996)).

Exemplary, nonlimiting fusion proteins that can be sulfated according to methods described herein include abatacept (Orencia®, Bristol-Myers Squibb), alefacept (Amevive®, Astellas Pharma), denileukin diftitox (Ontak®, Eisai), etanercept (Enbrel®, Amgen-Pfizer), and rilonacept (Arcalyst®, Regeneron Pharmaceuticals).

In some instances, a sulfated Fc region (or an Fc fragment containing a sulfated N-glycosylation site thereof) is conjugated to a heterologous polypeptide of at least 10, at least 20, at least 30, at least 40, at least 50, at least 60, at least 70, at least 80, at least 90 or at least 100 amino acids.

In some instances, a fusion protein can include an Fc region (or an Fc fragment containing an N-glycosylation site thereof) conjugated to marker sequences, such as a peptide to facilitate purification. A particular marker amino acid sequence is a hexa-histidine peptide, such as the tag provided in a pQE vector (QIAGEN, Inc., 9259 Eton Avenue, Chatsworth, Calif., 91311). Other peptide tags useful for purification include, but are not limited to, the hemagglutinin "HA" tag, which corresponds to an epitope derived from the influenza hemagglutinin protein (Wilson et al., 1984, Cell 37:767) and the "Flag" tag.

In other instances, methods described herein are used to sulfate a glycoprotein (or an Fc region or Fc fragment containing an N-glycosylation site thereof) that is conjugated to a diagnostic or detectable agent. Such fusion proteins can be useful for monitoring or prognosing development or progression of disease or disorder as part of a clinical testing procedure, such as determining efficacy of a particular therapy. Such diagnosis and detection can be accomplished by coupling a glycoprotein to detectable substances including, but not limited to, various enzymes, such as but not limited to horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as but not limited to iodine ($^{131}$I, $^{125}$I, $^{123}$I), carbon ($^{14}$C), sulfur ($^{35}$S), tritium ($^{3}$H), indium ($^{115}$In, $^{113}$In, $^{112}$In, $^{111}$In), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{153}$Gd, $^{159}$Gd, $^{149}$Pm, $^{140}$La, $^{169}$Yb, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{51}$Cr, $^{54}$Mn, $^{75}$Se, $^{13}$Sn, and $^{117}$Sn; positron emitting metals using various positron emission tomographies, non-radioactive paramagnetic metal ions, and molecules that are radio-labelled or conjugated to specific radioisotopes.

Techniques for conjugating therapeutic moieties to antibodies are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56. (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987)).

II. Sulfated Glycoproteins

A. Characteristics of Sulfated Glycoproteins

The disclosure is based, in part, on the novel finding that glycoproteins, such as antibodies, can be sulfated to affect function, such as antibody effector function. In some instances, a glycoprotein is sulfated on its amino acid backbone. For example, a glycoprotein described herein contains a sulfated amino acid residue within the Fc region.

In other instances, a glycoprotein is sulfated on a sugar moiety. For example, an antibody contains a sulfated glycan, such as a sulfated N-linked glycan, on an amino acid residue of the Fc region of the antibody (e.g., a sulfated glycan linked to Asn297 of an IgG). Such glycans include, for example, monosaccharides, disaccharides, and oligosaccharides (e.g., N-linked biantennary oligosaccharides). Any sugar moiety of a glycoprotein can be sulfated. For example, an antibody glycosylated with an N-linked biantennary oligosaccharide can be sulfated on any of its sugar moieties (e.g., a fucose, a mannose, an N-linked acetylglucosamine, or a galactose). Further, any ring atom of a sugar moiety that is amenable to sulfation can be sulfated. For example, a sugar ring can be sulfated at position 3, 4, or 6.

B. Methods of Sulfation

Glycoproteins can be sulfated using, e.g., enzymatic, metabolic, or chemoenzymatic sulfation.

1. Enzymatic Sulfation

In certain instances, a glycoprotein described herein is sulfated using a sulfating enzyme. Enzymes that sulfate polypeptide and/or glycan substrates are generally known. Particular sulfating enzymes include the family of sulfotransferases.

Sulfotransferases catalyze the transfer of a sulfate (i.e., sulfonate, —$SO_3$) group from an activated donor onto a hydroxyl or less frequently an amino group of the acceptor molecule. The nucleotide-analogue 3' phosphoadenosine 5' phosphosulfate (PAPS) invariably serves as the activated sulfate donor (Klaassen et al., FASEB J. 11:404-418 (1997)). PAPS is generated from ATP and $SO_4^{2-}$ by the sequential action of two enzymes: ATP sulfurylase, which synthesizes adenosine 5' phosphosulfate (APS); and APS kinase, which adds an ATP-derived phosphate to the 3' position of APS. In animal cells, both enzymatic activities are found within a single protein, termed the PAPS synthase (Li et al., J. Biol. Chem. 270:29453-29459; and Girard et al., FASEB J. 12:603-612 (1998)).

Two general classes of sulfotransferases exist: cytosolic sulfotransferases (Falany et al., FASEB J. 11:206-216 (1997)); and the Golgi-localized, usually membrane-bound sulfotransferases (CHSTs) (Bowman et al., Chem. Biol. 6:R9-R22 (1999)). These sulfotransferases are useful to sulfate glycoproteins according to the disclosure.

The CHST family comprises 14 genes in humans and mice (see, e.g., Rikke et al., Biochim. Biophys. Acta 1307: 331-338 (1996); Hemmerich et al., Glycobiology 10:849-856 (2000); Grunwell et al., Biochem. 41:13117-13126 (2002)). Such sulfotransferases are commercially available, e.g., from R&D Systems, Inc. (Minneapolis, Minn.). Non-limiting, exemplary CHST sulfotransferases that can be used in methods disclosed herein include CHST1 (GenBank Accession No. NP_003645), CHST2 (GenBank Accession No. Q9Y4C5), CHST3 (GenBank Accession No. NP_004264), CHST4 (GenBank Accession No. NP_005760), CHST5 (GenBank Accession No. NP_078809), CHST6 (GenBank Accession No. NP_067628), and CHST7 (GenBank Accession No. NP_063939).

Post Production Enzymatic Sulfation

In some embodiments, a glycoprotein, e.g., a glycosylated antibody, is sulfated after a glycoprotein is produced. For example, a glycoprotein can be recombinantly expressed in a host cell (as described herein) and purified using standard methods. The purified glycoprotein is then contacted with a sulfotransferase described herein (e.g., a recombinantly expressed and purified sulfotransferase) under conditions that facilitate sulfation of the purified glycoprotein. In certain embodiments, conditions include contacting the purified glycoprotein with a sulfotransferase in the presence of a sulfur donor, e.g., 3' phosphoadenosine 5' phosphosulfate (PAPS).

In some instances, enzymatic sulfation can be performed in the presence of agents that alter the tertiary structure of the Fc region (such as reducing and/or alkylating agents), in the presence of agents that stabilize enzyme activity (e.g., spermidine, spermatidine, L-lysine, protamine, or lysozyme), and/or can be performed under high pressure (such as in a barocycler).

Cell-Based Enzymatic Sulfation

In other sulfation methods, a glycoprotein and a sulfotransferase are recombinantly co-expressed in a host cell. A glycoprotein and/or a sulfotransferase can be homologous or heterologous to the host cell. Upon co-expression, the sulfotransferase sulfates the glycoprotein, after which the sulfated glycoprotein can be optionally purified. In some instances, the host cell is genetically engineered to increase sulfation of the recombinantly expressed glycoprotein, such as by introducing, overexpressing, or attenuating expression of certain enzymes involved in oligosaccharide or endogenous glycoprotein production (see, e.g., U.S. Pat. Nos. 5,047,335; 5,510,261; 5,278,299).

2. Metabolic Sulfation

Another method of sulfating glycoproteins involves metabolic sulfation. In such methods, sugars are first sulfated chemically and then added to culture media of host cells, which take up the sulfated sugars and incorporate them into glycoproteins.

In one exemplary process, a hydroxyl group of interest is sulfated, and the rest of the hydroxyl groups are acetylated on a carbohydrate. The procedure for the particular sulfated per-acetylated carbohydrate depends on which carbohydrate is of interest and the position of sulfation. Steps can include: 1) protection and de-protection of hydroxyl groups; 2) sulfation of a hydroxyl group using, e.g., pyridine-sulfur trioxide; and 3) per-acetylation of remaining hydroxyl groups. The process can be accomplished with any combination and sequence of these steps. Sugar sulfates are then neutralized as a calcium salt form, which can then be used directly or changed to another salt form.

Per-O-acetylated versions of both D- and L-forms of sugars can be sulfated chemically. Nonlimiting examples include 3, 4, 5, 6, or 7 carbon sugars (e.g., glyceraldehyde, erythrose, arabinose, galactose, mannopentulose); keto-sugars (such as fructose); aldo-sugars (such as Glc, Gal, Man); deoxy-sugars (such as fucose, 2-deoxy-glucose, rhamnose); N-acetylated-sugars (such as GlcNAc, ManNAc, GalNAc); reduced sugars (such as mannitol, sorbitol, glycerol); and polysaccharides (such as sucrose, raffinose, N-Acetyl-lactosamine). Specific, nonlimiting examples of sulfated sugars that can be produced using this method are provided in Table 1.

TABLE 1

| Sulfated sugars | |
| --- | --- |
| Galactose 1-Sulfate | N-Acetyl-Glucosamine 1-Sulfate |
| Galactose 2-Sulfate | N-Acetyl-Glucosamine 3-Sulfate |
| Galactose 3-Sulfate | N-Acetyl-Glucosamine 4-Sulfate |
| Galactose 4-Sulfate | N-Acetyl-Glucosamine 5-Sulfate |
| Galactose 5-Sulfate | N-Acetyl-Glucosamine 6-Sulfate |
| Galactose 6-Sulfate | N-Acetyl-Galactosamine 1-Sulfate |
| Glucose 1-Sulfate | N-Acetyl-Galactosamine 3-Sulfate |
| Glucose 2-Sulfate | N-Acetyl-Galactosamine 4-Sulfate |
| Glucose 3-Sulfate | N-Acetyl-Galactosamine 5-Sulfate |
| Glucose 4-Sulfate | N-Acetyl-Galactosamine 6-Sulfate |
| Glucose 5-Sulfate | N-Acetyl-Mannosamine 1-Sulfate |
| Glucose 6-Sulfate | N-Acetyl-Mannosamine 3-Sulfate |
| Mannose 1-Sulfate | N-Acetyl-Mannosamine 4-Sulfate |
| Mannose 2-Sulfate | N-Acetyl-Mannosamine 5-Sulfate |

TABLE 1-continued

| Sulfated sugars | |
| --- | --- |
| Mannose 3-Sulfate | N-Acetyl-Mannosamine 6-Sulfate |
| Mannose 4-Sulfate | Fucose 1-Sulfate |
| Mannose 5-Sulfate | Fucose 2-Sulfate |
| Mannose 6-Sulfate | Fucose 3-Sulfate |
| Fructose 1-Sulfate | Fucose 4-Sulfate |
| Fructose 3-Sulfate | Fucose 5-Sulfate |
| Fructose 4-Sulfate | |
| Fructose 5-Sulfate | |
| Fructose 6-Sulfate | |

3. Chemoenzymatic Sulfation

Chemoenzymatic sulfation can also be used to sulfate glycoproteins. Briefly, this method involves sulfation of a purified glycan, followed by incorporation of the sulfated glycan en bloc onto a polypeptide to produce a sulfated glycoprotein.

A glycan can be synthesized de novo using standard techniques or can be obtained from a glycoprotein using an appropriate enzyme, such as an endoglycosidase (e.g., EndoH or EndoF). After sulfation of a glycan, the sulfated glycan can be conjugated to a polypeptide using an appropriate enzyme, such as a transglycosidase, to produce a sulfated glycoprotein.

In one exemplary method, a purified N-glycan is obtained from a glycoprotein using an endoglycosidase. The purified N-glycan is then chemically activated on the reducing end to form a chemically active intermediate. The N-glycan is then further processed, trimmed, and/or glycosylated using appropriate known glycosidases. The glycan is then sulfated, such as using a sulfotransferase described herein. After engineering, the desired N-glycan is transferred onto a glycoprotein using a transglycosidase (such as a transglycosidase in which glycosidic activity has been attenuated using genetically engineering).

Production of sulfated sugars can include generation of libraries of sulfated sugars having specific sulfation patterns (for example, sugars sulfated on a single epitope, sugars sulfated on two epitopes of biantennary glycans, or sugars sulfated at a different carbon positions (e.g., 3-O, 4-O, or 6-O). In some methods, production of a sulfated glycoprotein includes selecting a particular sulfated sugar from such libraries and conjugating the sulfated sugar to a polypeptide. In other methods, libraries include mixtures of sulfated sugars, which can be conjugated to polypeptides and the resultant glycoprotein assayed for activity, as described herein.

III. Modulation of Fc Effector Functions

Fc regions of antibodies interact with cellular receptors to mediate antibody-dependent effector functions. For example, in the case of IgGs, different classes of FcγR mediate various cellular responses, such as phagocytosis by macrophages, antibody-dependent cell-mediated cytotoxicity by NK cells, and degranulation of mast cells. Each FcγR displays different binding affinities and IgG subclass specificities.

Sulfation of glycoproteins, e.g., using methods disclosed herein, results in modification of glycoprotein function, e.g., Fc region-mediated functions. Effector functions mediated by an antibody Fc region can be divided into two categories. The first type are effector functions that operate after the binding of antibody to an antigen. Such effector functions are mediated by cells of the immune system and include, for example, antibody-dependent cell-mediated cytotoxicity (ADCC) and complement dependent cytotoxicity (CDC)

(see, e.g., Daeron, Ann. Rev. Immunol. 15:203-234 (1997); Ward et al., Therapeutic Immunol. 2:77-94 (1995); and Ravetch et al., Ann. Rev. Immunol. 9:457-492 (1991)). The second type are effector functions that operate independently of antigen binding. These include functions that affect half-life, clearance, and the ability to be transferred across cellular barriers by transcytosis (see, e.g., Ward and Ghetie, Therapeutic Immunology 2:77-94 (1995)). Glycoproteins described herein that include an Fc region (or an effector-mediated portion thereof), such as antibodies, antibody fragments that include an Fc region, or glycoprotein conjugates that include an Fc region, can mediate these two classes of effector functions. For example, a therapeutic glycoprotein that includes a CH2 region (e.g., an Fc region) containing a sulfated glycan as described herein can modify one or more of these effector functions.

A. Effector Functions Mediated by Fc Receptors

1. Types of Fc Receptors

Several effector functions are mediated by Fc receptors (FcRs), which bind the Fc region of an antibody. It has been found that sulfating an Fc region of a glycoprotein modifies its ability to bind to FcRs and thus modifies its effector function. Accordingly, methods described herein can be used to modify one or more activity of a therapeutic glycoprotein.

FcRs are defined by their specificity for immunoglobulin isotypes; Fc receptors for IgG antibodies are referred to as FcγR, for IgE as FcεR, for IgA as FcαR and so on. Four subclasses of FcγR have been identified: FcγRI (CD64), FcγRII (CD32), FcγRIII (CD16), and FcγRIV (see, e.g., Nimmerjahn et al., Immunity 24:19-28 (2006)). Because each FcγR subclass is encoded by two or three genes, and alternative RNA spicing leads to multiple transcripts, a broad diversity in FcγR isoforms exists. The three genes encoding the FcγRI subclass (FcγRIA, FcγRIB and FcγRIC) are clustered in region 1q21.1 of the long arm of chromosome 1; the genes encoding FcγRII isoforms (FcγRIIA, FcγRIIB and FcγRIIC) and the two genes encoding FcγRIII (FcγRIIIA and FcγRIIIB) are all clustered in region 1q22. These different FcR subtypes are expressed on different cell types (see Ravetch et al., Ann. Rev. Immunol. 9:457-492 (1991)). For example, in humans, FcγRIIIB is found only on neutrophils, whereas FcγRIIIA is found on macrophages, monocytes, natural killer (NK) cells, and a subpopulation of T-cells.

Structurally, FcγRs are all members of the immunoglobulin superfamily, having an IgG-binding α-chain with an extracellular portion comprised of either two (FcγRI) or three (FcγRI) Ig-like domains. In addition, FcγRI and FcγRIII have accessory protein chains (γ, ζ) associated with the α-chain, which function in signal transduction. Receptors are also distinguished by their affinity for IgG. FcγRI exhibits a high affinity for IgG, $K_a = 10^8 - 10^9$ $M^{-1}$ (Ravetch et al., Ann. Rev. Immunol. 19:275-290 (2001)) and can bind monomeric IgG. In contrast FcγRII and FcγRIII show a relatively weaker affinity for monomeric IgG $K_a \leq 10^7$ $M^{-1}$ (Ravetch et al., Ann. Rev. Immunol. 19:275-290 (2001)), and hence only interact effectively with multimeric immune complexes. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see, e.g., Daeron, Ann. Rev. Immunol. 15:203-234 (1997)). NK-cells carry only FcγRIIIA, and binding of antibodies to FcγRIIIA leads to ADCC activity by NK cells.

Allelic variants of several human FcγRs are known to exhibit differences in binding of human and murine IgG, and a number of association studies have correlated clinical outcomes with the presence of specific allelic forms (see Lehrnbecher et al., Blood 94:4220-4232 (1999)). Accordingly, glycoproteins sulfated using methods described herein can have altered binding to these allelic variants and can be used as therapeutics for such conditions.

Another type of Fc receptor is the neonatal Fc receptor (FcRn). FcRn is structurally similar to major histocompatibility complex (MHC) and consists of an α-chain noncovalently bound to β2-microglobulin. FcRn has been proposed to regulate homeostasis of IgG in blood as well as possibly control transcytosis across tissues (Ghetie et al., Ann. Rev. Immunol. 18:739-766 (2000)).

2. Cellular Expression of Fc Receptors

Expression of FcRs varies in different immune cells (see Table 2). It has been found that sulfating a glycoprotein at an N-linked site of a CH2 domain of an Fc region, e.g., using a method described herein, affects FcR-mediated binding of the glycoprotein, thereby modulating its effects on different cell types.

TABLE 2

FcγR cellular distribution and effector function

| Receptor name | Principal antibody ligand | Affinity for ligand | Cell distribution | Effect following binding to antibody |
|---|---|---|---|---|
| FcγRI (CD64) | IgG1 and IgG3 | High (Kd ~$10^{-9}$M) | Macrophages | Phagocytosis |
| (CD64) | | | Neutrophils | Cell activation |
| | | | Eosinophils | Activation of respiratory burst |
| | | | Dendritic cells | Induction of microbe killing |
| FcγRIIA (CD32) | IgG | Low (Kd > $10^{-7}$M) | Macrophages | Phagocytosis |
| | | | Neutrophils | Degranulation (eosinophils) |
| | | | Eosinophils | |
| | | | Platelets | |
| | | | Langerhans cells | |

TABLE 2-continued

FcγR cellular distribution and effector function

| Receptor name | Principal antibody ligand | Affinity for ligand | Cell distribution | Effect following binding to antibody |
|---|---|---|---|---|
| FcγRIIB1 (CD32) | IgG | Low (Kd > $10^{-7}$M) | B Cells | No phagocytosis |
|  |  |  | Mast cells | Inhibition of cell activity |
| FcγRIIB2 (CD32) | IgG | Low (Kd > $10^{-7}$M) | Macrophages | Phagocytosis |
|  |  |  | Neutrophils Eosinophils | Inhibition of cell activity |
| FcγRIIIA (CD16a) | IgG | Low (Kd > $10^{-6}$M) | NK cells | Induction of antibody-dependent cell-mediated cytotoxicity (ADCC) |
|  |  |  | Macrophages (certain tissues) | Induction of cytokine release by macrophages |
| FcγRIIIB (CD16b) | IgG | Low (Kd > $10^{-6}$M) | Eosinophils | Induction of microbe killing |
|  |  |  | Macrophages Neutrophils Mast cells Follicular dendritic cells |  |
| FcγRIV | IgG2 | Intermediate | Neutrophils Monocytes Macrophages Dendritic cells | Activation of cell activity |
| FcRn | IgG |  | Monocytes | Transfers IgG from a mother to fetus through the placenta |
|  |  |  | Macrophages | Transfers IgG from a mother to infant in milk |
|  |  |  | Dendrite cells | Protects IgG from degradation |
|  |  |  | Epithelial cells Endothelial cells Hepatocytes |  |

The 72 kDa extracellular glycoprotein FcγRI is mainly expressed on myeloid cells such as monocytes, macrophages CD4+ progenitor cells and may elicit ADCC, endocytosis, and phagocytosis responses (Siberil et al., 2006, J Immunol Lett 106:111-118). The 40 kDa FcγRII group of receptors (A, B and C isoforms) exhibit extracellular domains but do not contain active signal transduction domains. FcγRIIA is mainly expressed on monocytes, macrophages, neutrophils, and platelets, whereas FcγRIIC receptor has only been identified on NK cells. These two receptors have been shown to initiate ADCC, endocytosis, phagocytosis and inflammatory mediator release (Cassel et al., 1993. Mol Immunol 30:451-60). By contrast, FcγRIIB (B1 and B2 types) receptors are expressed on B cells, Mast cells, basophils, monocytes, macrophages and dendritic cells and have been shown to downregulate immune responses triggered by the A and C isoforms.

The 50 kDa FcγRIIIA is expressed on NK cells, monocytes, macrophages and a subset of T lymphocytes, where it activates ADCC, phagocytosis, endocytosis and cytokine release (Gessner et al., 1998, Ann Hematology 76:231-48). The FcγRIIIB isoform is a glycosyl-phosphatidylinositol (GPI) anchored peripheral membrane protein involved in degranulation and production of reactive oxygen intermediates (Salmon et al., 1995 J. Clin. Inves. 95:2877-2885).

3. Binding Properties of Sulfated Glycoproteins

Sulfated glycoproteins of the disclosure can have altered FcR and/or C1q binding properties (e.g., binding specificity, equilibrium dissociation constant (KD), dissociation and association rates ($K_{off}$ and $K_{on}$ respectively), binding affinity and/or avidity), relative to a nonsulfated glycoprotein. One skilled in the art can determine which kinetic parameter is most important for a given application. For example, methods described herein can be used to modulate one or more activity of a glycoprotein having an Fc region, e.g., can be used to sulfate a glycoprotein to reduce its binding to one or more activating Fc receptor (e.g., FcγRIIIA) and/or to enhance its binding to an inhibitory Fc receptor (e.g., FcγRIIB) and thus to reduce ADCC activity. Alternatively, methods described herein can be used to sulfate a glycoprotein to increase its binding to one or more activating Fc receptor (e.g., FcγRIIIA) and/or to reduce its binding to an inhibitory Fc receptor (e.g., FcγRIIB) and thus to increase ADCC activity. The ratio of binding affinities (e.g., equilibrium dissociation constants (KD)) can indicate if ADCC activity of a sulfated glycoprotein is enhanced or decreased. Additionally, methods described herein can be used to sulfate a glycoprotein to reduce its binding to C1q (and to reduce or eliminate CDC activity), or to increase binding to C1q (and to increase CDC activity).

Affinities and binding properties of an Fc region for an FcR and/or C1q can be measured by a variety of in vitro assay methods known in the art for determining Fc-FcγR interactions. Nonlimiting examples of such methods include equilibrium methods (e.g., enzyme-linked immunoabsorbent assay (ELISA) or radioimmunoassay (RIA)), kinetics (e.g., BIACORE® analysis), indirect binding assays, competitive inhibition assays, fluorescence resonance energy transfer (FRET), gel electrophoresis, and chromatography (e.g., gel filtration). These and other methods can use a label on one or more of the components being examined and/or employ a variety of detection methods including, but not limited to, chromogenic, fluorescent, luminescent, or isotopic labels. In some instances, sulfation of a glycoprotein results in a detectable change in binding of a glycoprotein to an FcR and/or C1q.

In some instances, a sulfated glycoprotein exhibits reduced binding affinity for one or more Fc receptors including, but not limited to FcγRI (CD64) including isoforms FcγRIA, FcγRIB, and FcγRIC; FcγRII (CD32 including isoforms FcγRIIA, FcγRIIB, and FcγRIIC); and FcγRIII (CD16, including isoforms FcγRIIIA and FcγRIIB), relative to an nonsulfated glycoprotein. In certain embodiments, a sulfated glycoprotein does not have increased binding to FcγRIIB receptor as compared to nonsulfated glycoprotein.

In other instances, a sulfated glycoprotein exhibits increased binding affinity for one or more Fc receptors including, but not limited to FcγRI (CD64) including isoforms FcγRIA, FcγRIB, and FcγRIC; FcγRII (CD32 including isoforms FcγRIIA, FcγRIIB, and FcγRIIC); and FcγRIII (CD16, including isoforms FcγRIIIA and FcγRIIB), relative to a nonsulfated glycoprotein. In certain embodiments, a sulfated glycoprotein has increased binding to FcγRIIB receptor as compared to nonsulfated glycoprotein.

In one embodiment, a sulfated glycoprotein exhibits decreased binding affinity to FcγRI relative to a nonsulfated glycoprotein. In another embodiment, a sulfated glycoprotein exhibits a binding affinity for FcγRI receptor that is at least 1.2 fold, 1.5 fold, 1.8 fold, 2 fold, or at least 3 fold, or at least 5 fold, or at least 7 fold, or at least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than a nonsulfated glycoprotein. In another embodiment, a sulfated glycoprotein exhibits an affinity for FcγRI receptor that is at least 90%, at least 80%, at least 70%, at least 60%, at least 50%, at least 40%, at least 30%, at least 20%, at least 10%, or at least 5% less than a nonsulfated glycoprotein.

In other embodiments, a sulfated glycoprotein exhibits increased binding affinity to FcγRI relative to a nonsulfated glycoprotein. In another embodiment, sulfated glycoprotein exhibits a binding affinity for FcγRI receptor that is at least 1.2 fold, 1.5 fold, 1.8 fold, 2 fold, or at least 3 fold, or at least 5 fold, or at least 7 fold, or at least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold higher than a nonsulfated glycoprotein. In another embodiment, a sulfated glycoprotein exhibits an affinity for FcγRI receptor that is at least 5%, at least 10%, at least 20%, at least 30%, at least 40%, at least 50%, at least 60%, at least 70%, at least 80%, or at least 90% higher than a nonsulfated glycoprotein.

In one embodiment, a sulfated glycoprotein exhibits decreased affinity for the FcγRIIIA receptor relative to a nonsulfated glycoprotein. In another embodiment, a sulfated glycoprotein exhibits an affinity for FcγRIIIA receptor that is at least 1.2 fold, 1.5 fold, 1.8 fold, 2 fold, or at least 3 fold, or at least 5 fold, or at least 7 fold, or at least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than a nonsulfated glycoprotein. In another embodiment, a sulfated glycoprotein exhibits an affinity for FcγRIIIA receptor that is at least 90%, at least 80%, at least 70%, at least 60%, at least 50%, at least 40%, at least 30%, at least 20%, at least 10%, or at least 5% less than a nonsulfated glycoprotein.

In other embodiments, a sulfated glycoprotein exhibits increased affinity for the FcγRIIIA receptor relative to a nonsulfated glycoprotein. In another embodiment, a sulfated glycoprotein exhibits an affinity for FcγRIIIA receptor that is at least 1.2 fold, 1.5 fold, 1.8 fold, 2 fold, or at least 3 fold, or at least 5 fold, or at least 7 fold, or at least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold greater than a nonsulfated glycoprotein. In another embodiment, a sulfated glycoprotein exhibits an affinity for FcγRIIIA receptor that is at least 90%, at least 80%, at least 70%, at least 60%, at least 50%, at least 40%, at least 30%, at least 20%, at least 10%, or at least 5% greater than a nonsulfated glycoprotein.

The F158V allelic variant of the FcγRIIIA receptor has altered binding characteristics to antibodies. In one embodiment, a sulfated glycoprotein binds with decreased affinity to FcγRIIIA (F158V) relative to a nonsulfated glycoprotein. In another embodiment, a sulfated glycoprotein exhibits an affinity for FcγRIIIA (F158V) receptor that is at least 1.2 fold, 1.5 fold, 1.8 fold, 2 fold, or at least 3 fold, or at least 5 fold, or at least 7 fold, or at least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than that of a nonsulfated glycoprotein. In another embodiment, a sulfated glycoprotein exhibits an affinity for the FcγRIIIA (F158V) receptor that is at least 90%, at least 80%, at least 70%, at least 60%, at least 50%, at least 40%, at least 30%, at least 20%, at least 10%, or at least 5% less than a nonsulfated glycoprotein.

In other embodiments, a sulfated glycoprotein binds with increased affinity to FcγRIIIA (F158V) relative to a nonsulfated glycoprotein. In another embodiment, a sulfated glycoprotein exhibits an affinity for FcγRIIIA (F158V) receptor that is at least 1.2 fold, 1.5 fold, 1.8 fold, 2 fold, or at least 3 fold, or at least 5 fold, or at least 7 fold, or at least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold higher than that of a nonsulfated glycoprotein. In another embodiment, a sulfated glycoprotein exhibits an affinity for the FcγRIIIA (F158V) receptor that is at least 90%, at least 80%, at least 70%, at least 60%, at least 50%, at least 40%, at least 30%, at least 20%, at least 10%, or at least 5% higher than a nonsulfated glycoprotein.

In another embodiment, a sulfated glycoprotein exhibits an increased affinity for the FcγRIIB receptor as compared to a nonsulfated glycoprotein. In another embodiment, a sulfated glycoprotein exhibits an affinity for the FcγRIIB receptor that is unchanged or increased by at least at least 1.2 fold, 1.5 fold, 1.8 fold, 2 fold, or at least 3 fold, or at least 5 fold, or at least 7 fold, or at least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold than that of a nonsulfated glycoprotein. In another embodiment, a sulfated glycoprotein exhibits an affinity for the FcγRIIB receptor that is increased by at least 5%, at least 10%, at least 20%, at least 30%, at least 40%, at least 50%, at least 60%, at least 70%, at least 80%, at least 90%, or at least 95% relative to a nonsulfated glycoprotein.

In other embodiments, a sulfated glycoprotein exhibits a decreased affinity for the FcγRIIB receptor as compared to a nonsulfated glycoprotein. In another embodiment, a sulfated glycoprotein exhibits an affinity for the FcγRIIB receptor that is decreased by at least at least 1.2 fold, 1.5 fold, 1.8 fold, 2 fold, or at least 3 fold, or at least 5 fold, or at least 7 fold, or at least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold than that of a nonsulfated glycoprotein. In another embodiment, a sulfated glycoprotein exhibits an affinity for the FcγRIIB receptor that is decreased by at least 5%, at least 10%, at least 20%, at least 30%, at least 40%, at least 50%, at least 60%, at least 70%, at least 80%, at least 90%, or at least 95% relative to a nonsulfated glycoprotein.

In another embodiment, a sulfated glycoprotein exhibits an affinity for the FcγRI, FcγRIIIA, or FcγRIIIA (F158V) receptor that is about 100 nM to about 100 μM, or about 100 nM to about 10 μM, or about 100 nM to about 1 μM, or about 1 nM to about 100 μM, or about 10 nM to about 100 μM, or about 1 μM to about 100 μM, or about 10 μM to about 100 μM. In certain embodiments, a sulfated glycoprotein exhibits an affinity for the FcγRI, FcγRIIIA, or FcγRIIIA (F158V) receptor that is greater than about 1 μM, greater than about 5 μM, greater than about 10 μM, greater than about 25 μM, greater than about 50 μM, or greater than about 100 μM.

In another embodiment, a sulfated glycoprotein exhibits an affinity for the FcγRIIB receptor that is about 100 nM to about 100 μM, or about 100 nM to about 10 μM, or about 100 nM to about 1 μM, or about 1 nM to about 100 μM, or about 10 nM to about 100 μM, or about 1 μM to about 100 μM, or about 10 μM to about 100 μM. In certain embodiments, a sulfated glycoprotein exhibits an affinity for the FcγRI, FcγRIIIA, or FcγRIIIA (F158V) receptor that is less than about 100 μM, less than about 50 μM, less than about 10 μM, less than about 5 μM, less than about 2.5 μM, less than about 1 μM, less than about 100 nM, or less than about 10 nM.

In other embodiments, a sulfated glycoprotein exhibits an affinity for the FcγRIIB receptor that is between about 100 nM to about 100 μM, or about 100 nM to about 10 μM, or about 100 nM to about 1 μM, or about 1 nM to about 100 μM, or about 10 nM to about 100 μM, or about 1 μM to about 100 μM, or about 10 μM to about 100 μM. In certain embodiments, a sulfated glycoprotein exhibits an affinity for the FcγRI, FcγRIIIA, or FcγRIIIA (F158V) receptor that is less than about 100 μM, less than about 50 μM, less than about 10 μM, less than about 5 μM, less than about 2.5 μM, less than about 1 μM, less than about 100 nM, or less than about 10 nM.

4. Modification of ADCC Activity

Methods described herein can be used to sulfate a glycoprotein to modify its ability to induce antibody-dependent cell-mediated cytotoxicity ("ADCC"). ADCC refers to a form of cytotoxicity in which secreted Ig bound to Fc receptors (FcRs) present on certain cytotoxic cells (e.g., Natural Killer (NK) cells, neutrophils, and macrophages) enables these cytotoxic effector cells to bind specifically to an antigen-bearing target cell and subsequently kill the target cell with cytotoxins. Specific high-affinity IgG antibodies directed to the surface of target cells "arm" cytotoxic cells and are required for such killing. Lysis of the target cell is extracellular, requires direct cell-to-cell contact, and does not involve complement.

The ability of a glycoprotein (which is sulfated, e.g., using a method disclosed herein) to mediate lysis of a target cell by ADCC can be assayed. To assess ADCC activity, a sulfated glycoprotein described herein can be added to target cells in combination with immune effector cells, which can be activated by an antigen antibody complex, resulting in cytolysis of the target cell. Cytolysis can be detected, such as by detecting release of a label (e.g., radioactive substrates, fluorescent dyes or natural intracellular proteins) from lysed cells. Useful effector cells for such assays include peripheral blood mononuclear cells (PBMC) and Natural Killer (NK) cells. Specific examples of in vitro ADCC assays are described in Wisecarver et al., 1985 79:277-282; Bruggemann et al., 1987, J Exp Med 166:1351-1361; Wilkinson et al., 2001, J Immunol Methods 258:183-191; Patel et al., 1995 J Immunol Methods 184:29-38. ADCC activity can also be assessed in vivo, e.g., in an animal model, such as that disclosed in Clynes et al., 1998, PNAS USA 95:652-656.

In one embodiment, a sulfated glycoprotein exhibits decreased ADCC activity relative to a nonsulfated glycoprotein. In some embodiments, a sulfated glycoprotein exhibits ADCC activity that is at least 1.2 fold, 1.5 fold, 1.8 fold, 2 fold, or at least 3 fold, or at least 5 fold, or at least 10 fold, or at least 50 fold, or at least 100 fold less than that of a nonsulfated glycoprotein. In still another embodiment, a sulfated glycoprotein exhibits ADCC activity that is reduced by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to a nonsulfated glycoprotein. In certain embodiments, a sulfated glycoprotein exhibits no detectable ADCC activity.

In other embodiments, a sulfated glycoprotein exhibits increased ADCC activity relative to a nonsulfated glycoprotein. In some embodiments, a sulfated glycoprotein exhibits ADCC activity that is at least 1.2 fold, 1.5 fold, 1.8 fold, 2 fold, or at least 3 fold, or at least 5 fold, or at least 10 fold, or at least 50 fold, or at least 100 fold higher than that of a nonsulfated glycoprotein. In still another embodiment, a sulfated glycoprotein exhibits ADCC activity that is increased by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to a nonsulfated glycoprotein.

B. Effector Functions Mediated by Complement

Another antibody effector function is "complement dependent cytotoxicity", or "CDC", which refers to a biochemical event of antibody-mediated target cell destruction by the complement system. The complement system is a complex system of proteins found in normal blood plasma that combines with antibodies to destroy pathogenic bacteria and other foreign cells.

1. C1q Binding

C1q and two serine proteases, C1r and C1s, form the complex C1, the first component of the CDC pathway, and Fc binding to C1q mediates CDC (see Ward et al., Therapeutic Immunology 2:77-94 (1995)).

In one embodiment, a sulfated glycoprotein exhibits decreased affinity to C1q relative to a nonsulfated glycoprotein. In another embodiment, a sulfated glycoprotein exhibits an affinity for C1q that is at least 1.2 fold, 1.5 fold, 1.8 fold, 2 fold, or at least 3 fold, or at least 5 fold, or at least 7 fold, or at least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than a nonsulfated glycoprotein. In another embodiment, a sulfated glycoprotein exhibits an affinity for C1q that is at least 90%, at least 80%, at least 70%, at least 60%, at least 50%, at least 40%, at least 30%, at least 20%, at least 10%, or at least 5% less than a nonsulfated glycoprotein.

In other embodiments, a sulfated glycoprotein exhibits increased affinity to C1q relative to a nonsulfated glycoprotein. In another embodiment, a sulfated glycoprotein exhibits an affinity for C1q that is at least 1.2 fold, 1.5 fold, 1.8 fold, 2 fold, or at least 3 fold, or at least 5 fold, or at least 7 fold, or at least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold higher than a nonsulfated glycoprotein. In another embodiment, a sulfated glycoprotein exhibits an affinity for C1q that is at least 90%, at least 80%, at least 70%, at least 60%, at least 50%, at least 40%, at least 30%, at least 20%, at least 10%, or at least 5% higher than a nonsulfated glycoprotein.

In another embodiment, a sulfated glycoprotein exhibits an affinity for C1q that is about 100 nM to about 100 µM, or about 100 nM to about 10 µM, or about 100 nM to about 1 µM, or about 1 nM to about 100 µM, or about 10 nM to about 100 µM, or about 1 µM to about 100 µM, or about 10 µM to about 100 µM. In certain embodiments, a sulfated glycoprotein exhibits an affinity for C1q that is greater than about 1 µM, greater than about 5 µM, greater than about 10 µM, greater than about 25 µM, greater than about 50 µM, or greater than about 100 µM.

2. CDC Activity Mediated by Sulfated Glycoproteins

In some embodiments, a sulfated glycoprotein described herein can exhibit a modified level of complement activation, e.g., relative to a nonsulfated glycoprotein. Any known CDC assay (such as described, e.g., in Gazzano-Santoro et al., 1996, J. Immunol. Methods, 202:163), can be performed to assess complement activation. In one nonlimiting, exemplary method, various concentrations of glycoprotein (sulfated or nonsulfated) and human complement are diluted with buffer. Cells that express an antigen to which a glycoprotein binds are diluted to a density of about $1 \times 10^6$ cells/mL. Mixtures of glycoprotein (sulfated or nonsulfated), diluted human complement, and cells expressing the antigen are added to a flat bottom tissue culture 96 well plate and allowed to incubate for 2 hrs at 37° C. and 5% $CO_2$ to facilitate complement mediated cell lysis. 50 µL of alamar blue (Accumed International) is then added to each well and incubated overnight at 37° C. Absorbance is measured using a 96-well fluorometer with excitation at 530 nm and emission at 590 nm. Results can be expressed in relative fluorescence units (RFU). Sample concentrations can be computed from a standard curve, and percent activity of the sulfated glycoprotein is compared to that of the nonsulfated glycoprotein. A difference in percent activity of the sulfated glycoprotein compared to that of the nonsulfated glycoprotein indicates that the sulfated glycoprotein exhibits a modified level of complement activation, e.g., relative to a corresponding nonsulfated glycoprotein.

In one embodiment, a sulfated glycoprotein exhibits decreased CDC activity relative to a nonsulfated glycoprotein. In another embodiment, a sulfated glycoprotein exhibits its CDC activity that is at least 1.2 fold, 1.5 fold, 1.8 fold, 2 fold, or at least 3 fold, or at least 5 fold, or at least 10 fold, or at least 50 fold, or at least 100 fold less than that of a nonsulfated glycoprotein. In still another embodiment, a sulfated glycoprotein exhibits CDC activity that is reduced by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to a nonsulfated glycoprotein. In certain embodiments, a sulfated glycoprotein exhibits no detectable CDC activity.

In other embodiments, a sulfated glycoprotein exhibits increased CDC activity relative to a nonsulfated glycoprotein. In another embodiment, a sulfated glycoprotein exhibits its CDC activity that is at least 1.2 fold, 1.5 fold, 1.8 fold, 2 fold, or at least 3 fold, or at least 5 fold, or at least 10 fold, or at least 50 fold, or at least 100 fold higher than that of a nonsulfated glycoprotein. In still another embodiment, a sulfated glycoprotein exhibits CDC activity that is increased by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to a nonsulfated glycoprotein.

C. Other Properties of Sulfated Glycoproteins

Sulfating glycoproteins as described herein results in glycoproteins with modified clearance, half-life, apoptosis, and/or phagocytosis, relative to non-sulfated glycoproteins. For example, a glycoprotein can be sulfated to alter its binding affinity for FcRn, and thus alter its clearance/half-life properties (see, e.g., D'Acqua et al., J. Immunol. 169: 1571-1580 (2002)).

IV. Recombinant Gene Expression

In accordance with the present disclosure, there may be employed conventional molecular biology, microbiology, and recombinant DNA techniques within the skill of the art. Such techniques are described in the literature (see, e.g., Sambrook, Fritsch & Maniatis, Molecular Cloning: A Laboratory Manual, Second Edition (1989) Cold Spring Harbor Laboratory Press, Cold Spring Harbor, N.Y.; DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells and Enzymes (IRL Press, (1986)); B. Perbal, A Practical Guide To Molecular Cloning (1984); F. M. Ausubel et al. (eds.), Current Protocols in Molecular Biology, John Wiley & Sons, Inc. (1994).

Recombinant expression of a gene, such as a gene encoding a polypeptide, such as an antibody or a sulfotransferase described herein, can include construction of an expression vector containing a polynucleotide that encodes the polypeptide. Once a polynucleotide has been obtained, a vector for the production of the polypeptide can be produced by recombinant DNA technology using techniques known in the art. Known methods can be used to construct expression vectors containing polypeptide coding sequences and appropriate transcriptional and translational control signals. These methods include, for example, in vitro recombinant DNA techniques, synthetic techniques, and in vivo genetic recombination.

An expression vector can be transferred to a host cell by conventional techniques, and transfected cells can then cultured by conventional techniques to produce polypeptide.

A variety of host expression vector systems can be used (see, e.g., U.S. Pat. No. 5,807,715). Such host-expression systems can be used to produce polypeptides and, where desired, subsequently purified. Such host expression systems include microorganisms such as bacteria (e.g., *E. coli* and *B. subtilis*) transformed with recombinant bacteriophage DNA, plasmid DNA or cosmid DNA expression vectors containing polypeptide coding sequences; yeast (e.g., *Saccharomyces* and *Pichia*) transformed with recombinant yeast expression vectors containing polypeptide coding sequences; insect cell systems infected with recombinant virus expression vectors (e.g., baculovirus) containing polypeptide coding sequences; plant cell systems infected with recombinant virus expression vectors (e.g., cauliflower mosaic virus, CaMV; tobacco mosaic virus, TMV) or transformed with recombinant plasmid expression vectors (e.g. Ti plasmid) containing polypeptide coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

For bacterial systems, a number of expression vectors can be used, including, but not limited to, the $E.\ coli$ expression vector pUR278 (Ruther et al., 1983, EMBO 12:1791); pIN vectors (Inouye & Inouye, 1985, Nucleic Acids Res. 13:3101-3109; Van Heeke & Schuster, 1989, J. Biol. Chem. 24:5503-5509); and the like. pGEX vectors can also be used to express foreign polypeptides as fusion proteins with glutathione 5-transferase (GST).

For expression in mammalian host cells, viral-based expression systems can be utilized (see, e.g., Logan & Shenk, 1984, Proc. Natl. Acad. Sci. USA 8 1:355-359). The efficiency of expression can be enhanced by inclusion of appropriate transcription enhancer elements, transcription terminators, etc. (see, e.g., Bittner et al., 1987, Methods in Enzymol. 153:516-544).

In addition, a host cell strain can be chosen that modulates expression of inserted sequences, or modifies and processes the gene product in the specific fashion desired. Different host cells have characteristic and specific mechanisms for post-translational processing and modification of proteins and gene products. Appropriate cell lines or host systems can be chosen to ensure the correct modification and processing of the polypeptide expressed. Such cells include, for example, established mammalian cell lines and insect cell lines, animal cells, fungal cells, and yeast cells. Mammalian host cells include, but are not limited to, CHO, VERY, BHK, HeLa, COS, MDCK, 293, 3T3, W138, BT483, Hs578T, HTB2, BT20 and T47D, NS0 (a murine myeloma cell line that does not endogenously produce any immunoglobulin chains), CRL7O3O and HsS78Bst cells.

For long-term, high-yield production of recombinant proteins, host cells are engineered to stably express a polypeptide. Host cells can be transformed with DNA controlled by appropriate expression control elements known in the art, including promoter, enhancer, sequences, transcription terminators, polyadenylation sites, and selectable markers. Methods commonly known in the art of recombinant DNA technology can be used to select a desired recombinant clone.

Once a glycoprotein described herein been produced by recombinant expression, it may be purified by any method known in the art for purification, for example, by chromatography (e.g., ion exchange, affinity, and sizing column chromatography), centrifugation, differential solubility, or by any other standard technique for purification of proteins. For example, an antibody can be isolated and purified by appropriately selecting and combining affinity columns such as Protein A column with chromatography columns, filtration, ultra filtration, salting-out and dialysis procedures (see Antibodies: A Laboratory Manual, Ed Harlow, David Lane, Cold Spring Harbor Laboratory, 1988). Further, as described herein, a glycoprotein can be fused to heterologous polypeptide sequences to facilitate purification. Glycoproteins having desired sugar chains can be separated with a lectin column by methods known in the art (see, e.g., WO 02/30954).

V. Pharmaceutical Compositions and Administration

A sulfated glycoprotein described herein can be incorporated into a pharmaceutical composition. Such a pharmaceutical composition is useful as an improved composition for prevention and/or treatment of diseases relative to the nonsulfated glycoprotein. Pharmaceutical compositions comprising a sulfated glycoprotein can be formulated by methods known to those skilled in the art (see, e.g., Remington's Pharmaceutical Sciences pp. 1447-1676 (Alfonso R. Gennaro, ed., 19th ed. 1995)). Pharmaceutical composition can be administered parenterally in the form of an injectable formulation comprising a sterile solution or suspension in water or another pharmaceutically acceptable liquid. For example, a pharmaceutical composition can be formulated by suitably combining a sulfated glycoprotein with pharmaceutically acceptable vehicles or media, such as sterile water and physiological saline, vegetable oil, emulsifier, suspension agent, surfactant, stabilizer, flavoring excipient, diluent, vehicle, preservative, binder, followed by mixing in a unit dose form required for generally accepted pharmaceutical practices. The amount of active ingredient included in pharmaceutical preparations is such that a suitable dose within the designated range is provided.

The sterile composition for injection can be formulated in accordance with conventional pharmaceutical practices using distilled water for injection as a vehicle. For example, physiological saline or an isotonic solution containing glucose and other supplements such as D-sorbitol, D-mannose, D-mannitol, and sodium chloride may be used as an aqueous solution for injection, optionally in combination with a suitable solubilizing agent, for example, alcohol such as ethanol and polyalcohol such as propylene glycol or polyethylene glycol, and a nonionic surfactant such as polysorbate 80™, HCO-50 and the like.

Nonlimiting examples of oily liquid include sesame oil and soybean oil, and it may be combined with benzyl benzoate or benzyl alcohol as a solubilizing agent. Other items that may be included are a buffer such as a phosphate buffer, or sodium acetate buffer, a soothing agent such as procaine hydrochloride, a stabilizer such as benzyl alcohol or phenol, and an antioxidant. The formulated injection can be packaged in a suitable ampule.

Route of administration can be parenteral, for example, administration by injection, transnasal administration, transpulmonary administration, or transcutaneous administration. Administration can be systemic or local by intravenous injection, intramuscular injection, intraperitoneal injection, subcutaneous injection.

A suitable means of administration can be selected based on the age and condition of the subject. A single dose of a pharmaceutical composition containing a sulfated glycoprotein can be selected from a range of 0.001 to 1000 mg/kg of body weight. On the other hand, a dose can be selected in the range of 0.001 to 100000 mg/body weight, but the present disclosure is not limited to such ranges. Dose and method of administration can vary depending on the weight, age, condition, and the like of the subject, and can be suitably selected as needed by those skilled in the art.

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

The disclosure is further illustrated by the following examples. The examples are provided for illustrative purposes only. They are not to be construed as limiting the scope or content of the disclosure in any way.

EXAMPLES

Example 1—Sulfation of Fc Region of IgG and Characterization of Sulfation Pattern A. Methods
1. Generation of Glycosylated Fc Regions The antibody adalimumab was used as a model protein to test the efficacy of sulfation by sulfotransferases. Glycosylated Fc portions of the antibody were generated by proteolytic cleavage of the antibody by papain using a Fab Preparation Kit (Thermo Scientific, Rockford, Ill.). Briefly, 10 mg antibody was incubated with 1 mL of sepharose-bound papain slurry in the presence of digestion buffer containing 20 mM cysteine at pH 7.0. Incubation was performed for 18 hrs at 37° C. in a shaker water bath. Papain was separated from digested protein by centrifugation. Supernatant was collected and the pH was adjusted to 7.5. Fc fragments were purified on an anion exchange column at pH 7.5. Under these conditions, Fc was retained on the column while Fab eluted in the flow through.

2. Sulfation using Sulfotransferases

Intact antibody and Fc fragments were subjected to sulfation by incubation with soluble CHST2 and CHST5 enzymes at pH 6.5 and 7.5. These sulfotransferases were produced in insect cells by introducing a baculovirus vector containing a nucleotide sequence encoding a soluble catalytic domain (where the nucleotide sequence encoding the transmembrane portion was deleted). The sulfotransferases also included a His tag on either C- or N-terminus for purification and detection purposes. The sulfation reactions were conducted at 37° C. in the presence of 2.5 mM PAPS, 50 mM MES buffer, pH 7.2, 1 mM $Mg^{2+}$, 1 mM $Mn^{2+}$, and 1 mM $Ca^{2+}$. Reactions were run for 18 hrs, and PAPS was spiked at 2.5 mM after 6 hrs.

In a separate sulfation method, model antibodies and Fc-fusion proteins (Enbrel® (Amgen-Pfizer), Herceptin® (Roche), MabThera® (Roche), Campath® (Genzyme/Bayer), Erbitux® (Merck-Serono), and Orencia (Bristol-Myers Squibb)) were sulfated using CHST2 and CHST5 under the following reaction conditions. Briefly, 1 mg of each protein was incubated with 40 µg of purified enzyme, in the presence of 10 mM MES, pH 7.3, 2.5 mM $MgCl_2$, 2.5 mM $MnCl_2$ and 2.5 mM PAPS at 37° C. for 18 hrs. After 6 hrs, additional 2.5 mM PAPS and 40 g of purified enzyme were added to the reaction.

3. Structural Analysis of Glycan Sulfation

The resultant sulfated glycoproteins were digested using trypsin, and the tryptic glycopeptides were analyzed by LC-MS/MS.

Figure 2:
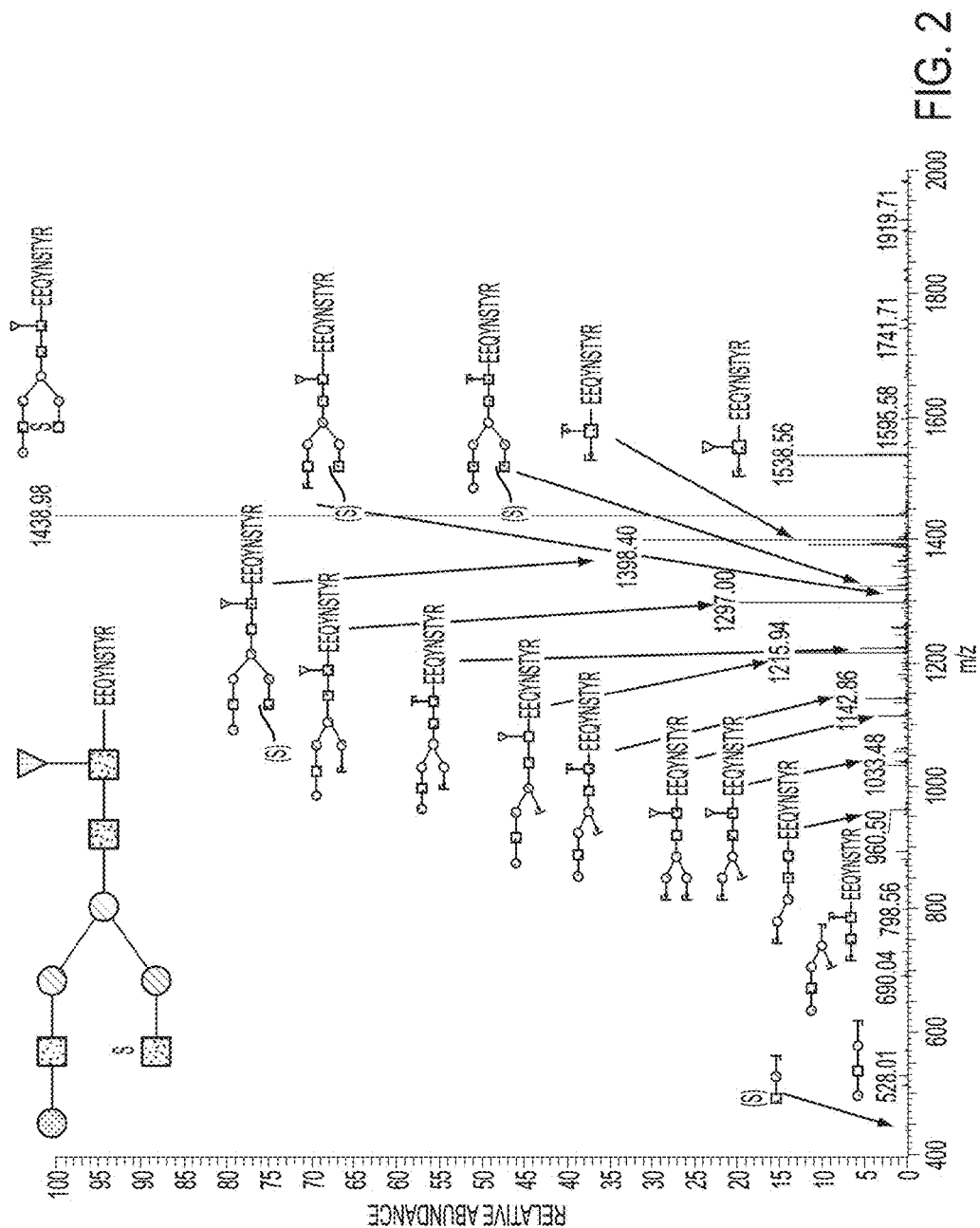
FIG. 2 is a representation of an LC-MS/MS profile of tryptic digests of sulfated glycopeptides.
Figure 3:
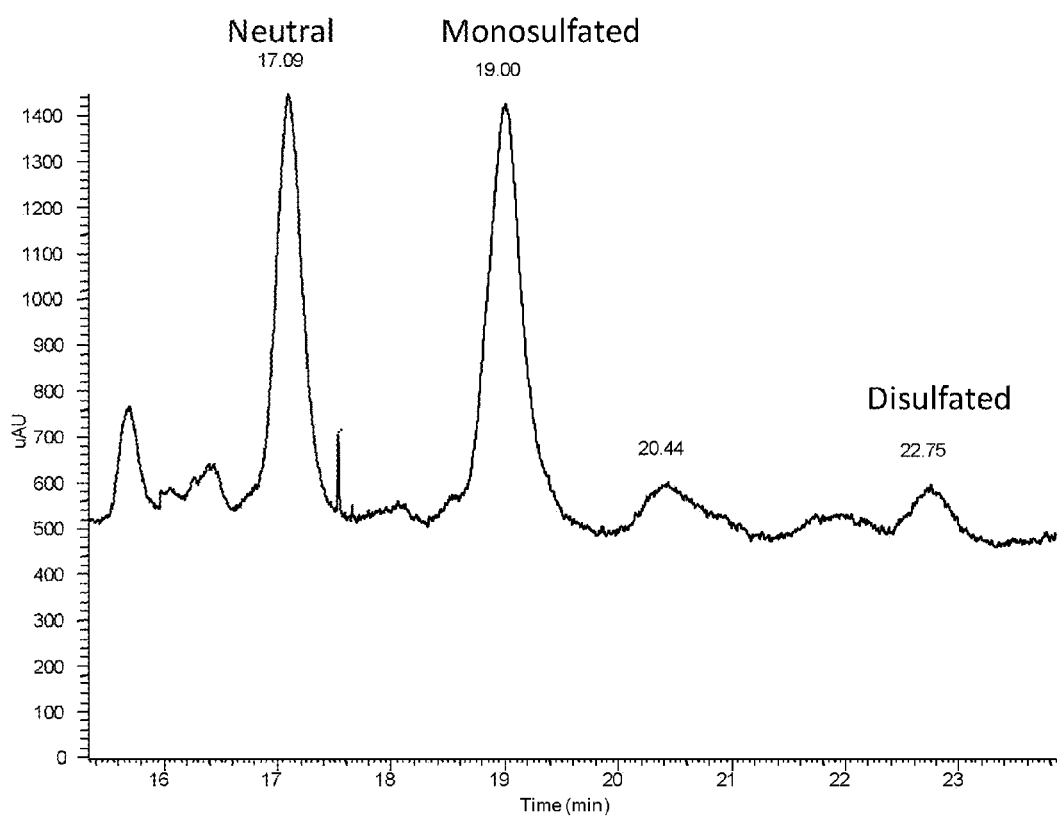
FIG. 3 is a representation a UV A280 trace of sulfated and non-sulfated glycoproteins.

FIG. 2 illustrates an example of a sulfated glycopeptide LC-MS/MS profile obtained from the analysis of sulfated glycoproteins. Based on the fragmentation profile obtained from sulfated glycopeptide RP-LC/MS-MS analysis, a specific method for monitoring sulfation of specific glycopeptides was developed based on LC-MRM-MS (Chen et al., Current Proteomics, 7:158-167 (2010); Stadlmann et al., Proteomics 8:2858-2871 (2008); Kurogochi et al., Mol. Cell. Proteomics 9:2354-2368 (2010)). Daughter ions were selected based on the favored fragmentation of glycosidic bonds and included both B-type (containing the non-reducing end sugars) and Y-type (containing the reducing end and the peptide) fragments. Diagnostic fragments or daughter ions for sulfated glycopeptides ions included 284.2 (Sulfated HexNAc), 446.3 (sulfated LAcNAc), as well as the fragments Peptide+HexNAc and Peptide+HexNAc+Fuc, which were useful for confirming the mass of the peptide backbone (FIG. 2). The chromatographic conditions of the LC/MRM-MS method also enabled the separation of the sulfated glycopeptides from non-sulfated glycopeptides, therefore facilitating the sulfation identification and quantification using UV detection (FIG. 3).

Through these analyses, it was confirmed that both CHST2 and CHST5 were able to sulfate the Fc fragment as well as the intact antibody.

Overall, both CHST2 and CHST5 were active under the same reaction conditions (buffer formulation, reagents concentration), and they had similar affinities for their substrates GlcNAc-Man and PAPS (0.3 mM and 0.5 mM, respectively).

Figure 4:
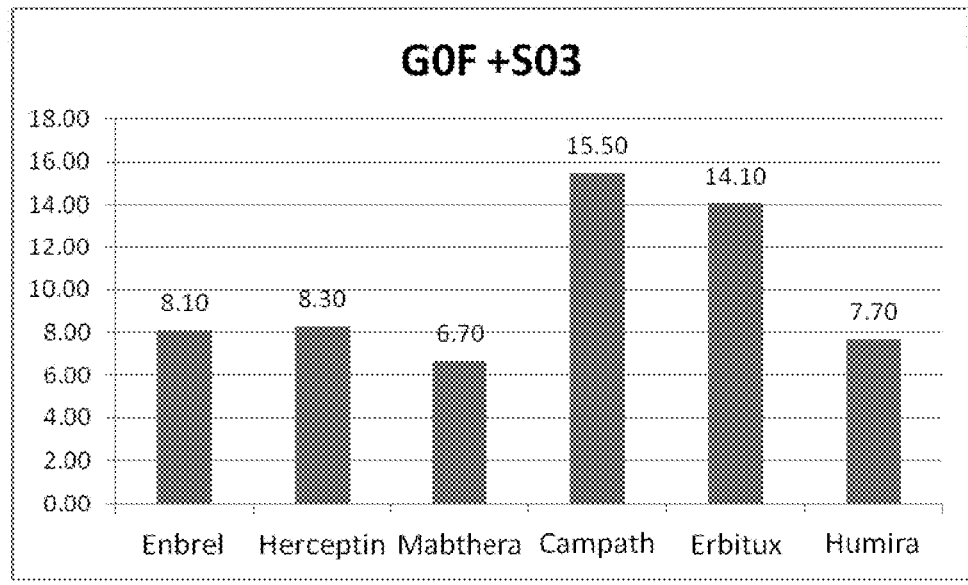
FIG. 4 is a diagrammatic representation of sulfation of intact therapeutic antibodies Enbrel, Herceptin, Mabthera, Campath, Erbitux, and Humira.

The proteins Enbrel®, Herceptin®, Mabthera®, Campath®, and Erbitux® were used as model proteins and were sulfated by CHST5 as described above. The sulfated protein products were analyzed and quantified by LC-MRM-MS, as described above. Sulfation efficiency is represented in FIG. 4 as a fraction of sulfated GOF glycan (the most abundant glycan species) relative to non-sulfated GOF. As depicted in FIG. 4, sulfation of GOF on the intact proteins ranged from 7% to 13%.

Example 2—Characterization of Binding of Sulfated Fc Region to Fc Receptors

The relative balance of engagement of activating and inhibitory FcγRs is important for the overall effector functions of individual IgG subclasses in vivo. This example characterizes FcγR binding of sulfated Fc regions.

FcγR binding of a model antibody (adalimumab), which was sulfated as described in Example 1, was measured using Surface Plasmon Resonance. A Biacore CM4 biosensor chip was conditioned with a mild acid/base treatment to remove non-specifically bound material on the chip surface after manufacturing. Then about 250 RU's of recombinant Protein L, diluted to 10 µg/mL in 10 mM Sodium acetate, pH 4.5, was immobilized on the biosensor chip surface via amine coupling. After immobilization of the recombinant Protein L, sulfated and nonsulfated intact antibodies and Fc fragments were diluted to 5 µg/mL in HBS-EP pH 7.4 and captured over the test flow cell. Then varying dilutions of recombinant human FcγRI, FcγRIIA, FcγRIIB/C, FcγRIIIA, and FcγRIIIB (R&D Systems/Cat: 1257-FC, 1330-CD, 1875-CD, 4325-FC and 1597-FC) were prepared in HBS-EP pH 7.4 and run over the sensor surface to determine their relative binding affinity.

After each cycle (concentration tested), the chip surface was washed with 10 mM glycine pH 1.7 to regenerate the flow cell surface. At the end of the experiment, data was fit using the 1:1 Langmuir binding model.

Sulfated adalimumab binding to FcγRI was saturable and fit to the 1:1 binding model. The binding is described in Table 3:

TABLE 3

| ka (1/Ms) | kd (1/s) | KD (M) | Rmax (RU) |
|---|---|---|---|
| 4.10E+05 | 1.42E−04 | 3.47E−10 | 150.5 | binding of sulfated adalimumab to FcγRI.

Further, sulfated adalimumab had higher affinity towards FcγRI and FcγRIIIa than non-sulfated adalimumab. This finding suggests higher ADCC activity for mononuclear cells and low ADCC for polymorphonuclear cells.

Example 3—Characterization of Golgi Sulfotransferases

A. Methods

Mouse CHST2, CHST5, and CHST7 genes were amplified from mouse clones and cloned into baculoviral transfer vector pAc4NH (Pharmingen). The inserts were co-transfected into Sf9 cells using standard methods. A culture was infected with 0.1 to 0.3% vol/vol of baculoviral stock and monitored using a ViCell over a period of 3 to 5 days. When viability of fully infected cells dropped to about 75% to 85%, the cells were spun down and the spent media was concentrated and dialyzed prior to running over a NiNTA column. The eluted fractions were concentrated via a 10 kDa spin concentrator and washed with TBS or PBS and frozen in aliquots at −20° C. until ready to use.

GlcNAc-Man was used as a simple substrate to determine the enzymes' biochemical characteristics such as kinetics, requirements for divalent cations, substrates stability or optimum pH range. Standard assay conditions were as follows: 50 mM MES buffer pH 7, 2.5 mM $MgCl_2$, 2.5 mM $MnCl_2$, 1.25 mM $CaCl_2$, 2.5 mM PAPS, 1 mM GlcNAc-Man, and 2-5 µg purified enzyme. Reactions were carried out for 18 hrs at 37° C. with spiking additional 2.5 mM of PAPS after 4-5 hrs of reaction initiation. In order to determine kinetics constants for CHST2 and CHST5, reaction series were run with a range of substrate concentrations: GlcNAc-Man (0.01 mM-5 mM) and PAPS (0.01 mM-5 mM). Reactions were incubated for 2 hrs (which was within the initial velocity of the enzyme that was determined prior to the experiment).

N-glycans derived from Herceptin® and Humira® were used as model complex substrates to determine enzyme substrate specificity, as many of these enzymes (including CHST5 and CHST7) had not been previously been characterized as branched sugars sulfotransferases. Both monoclonal antibodies were subjected to deglycosylation by endoglycosidase (PNGase F) followed by labeling with 2AB tag on the non-reducing end. These complex N-glycans were used as substrates to determine substrate specificities of various sulfotransferases (CHSTs). Products and substrates were separated and quantified on a normal phase HILIC-LC chromatography.

B. Results

Figure 5:
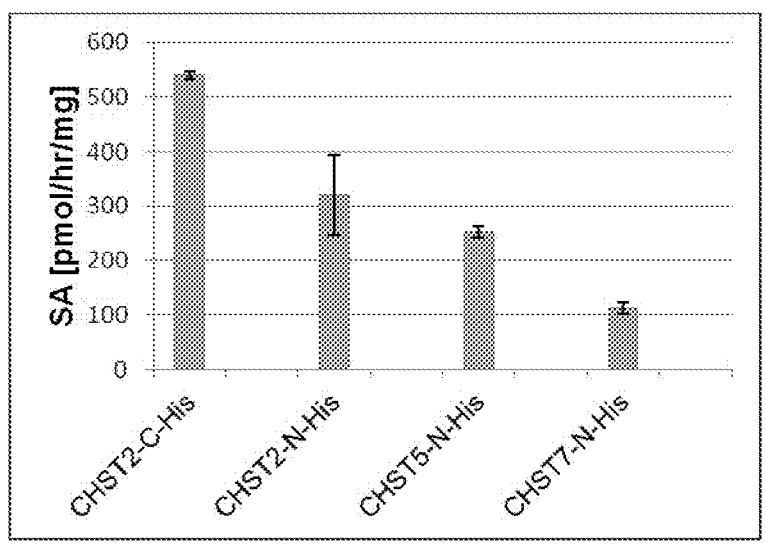
FIG. 5 is a diagrammatic representation of specific activity of different CHSTs with a simple, disaccharide substrate.

Surprisingly, the tested enzymes were able to efficiently sulfate the branched sugars from the model antibodies. Specific activity, as measured by the amount of sulfated GlcNAc-Man per unit of time by one mg of enzyme, was higher for CHST2 (both C- and N-His tagged) and lower for CHST5 and CHST7. This demonstrates that tagging either terminus did not have deleterious effect on enzyme activity (FIG. 5).

Figure 6A:
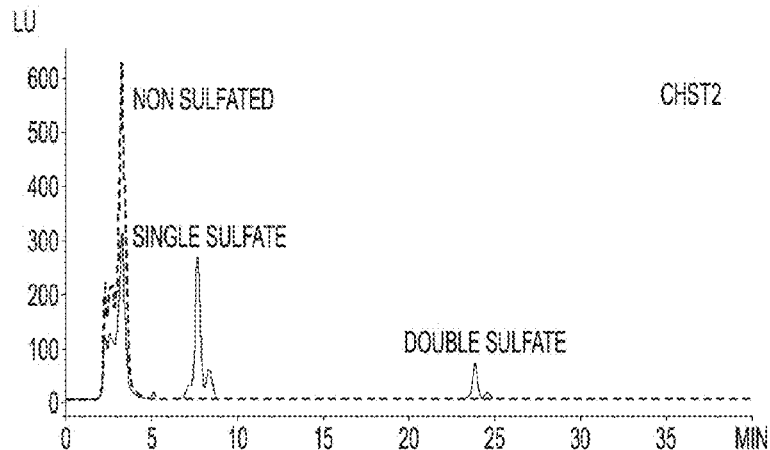
FIG. 6A, FIG. 6B, and FIG. 6C depict a panel of representations of HILIC-LC chromatography of Humira DS glycans sulfated by CHST2 (FIG. 6A), CHST5 (FIG. 6B), or CHST2 and CHST5 (FIG. 6C).
Figure 6B:
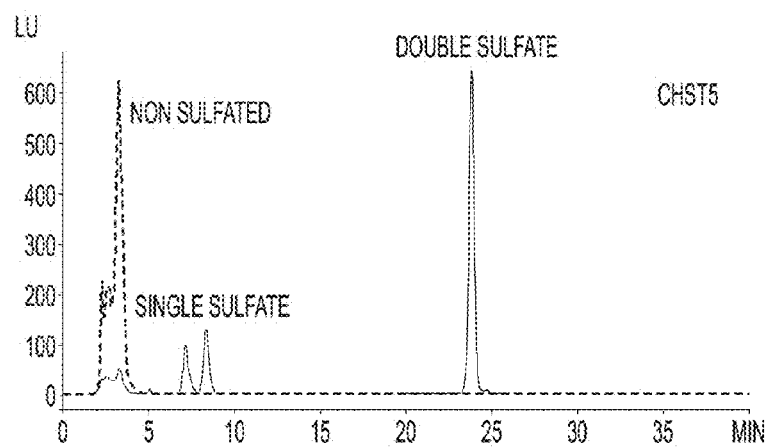
Figure 6C:
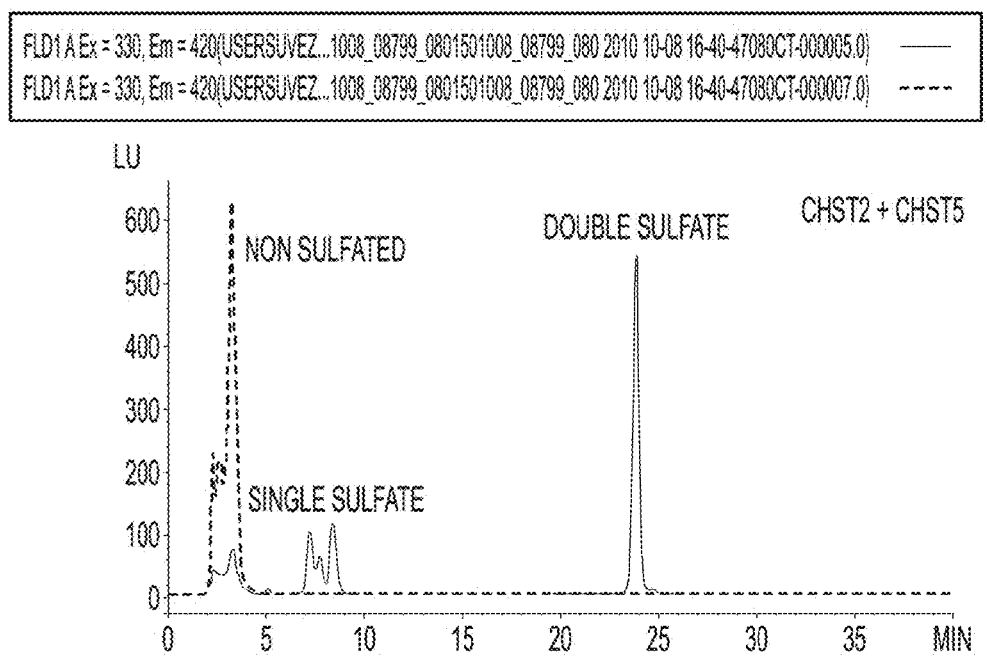
Figure 7:
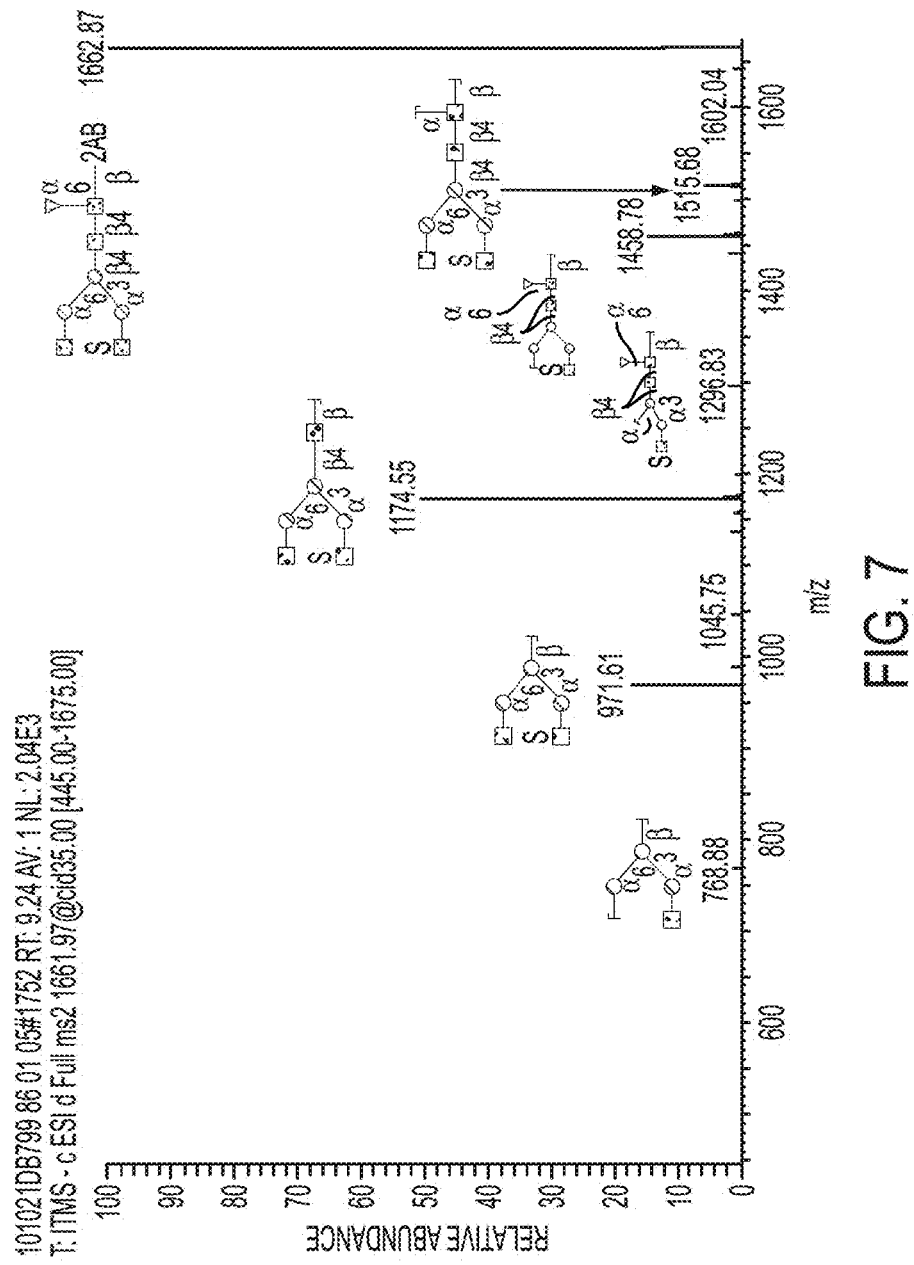
FIG. 7 is a representation of MS/MS analysis of mass species 1662 (4,3,1,0,0+SO$_3$). This mass correlates with G0F with a single sulfate. Fragmentation analysis by MS/MS suggests sulfation of a terminal GlcNAc residue.
Figure 8:
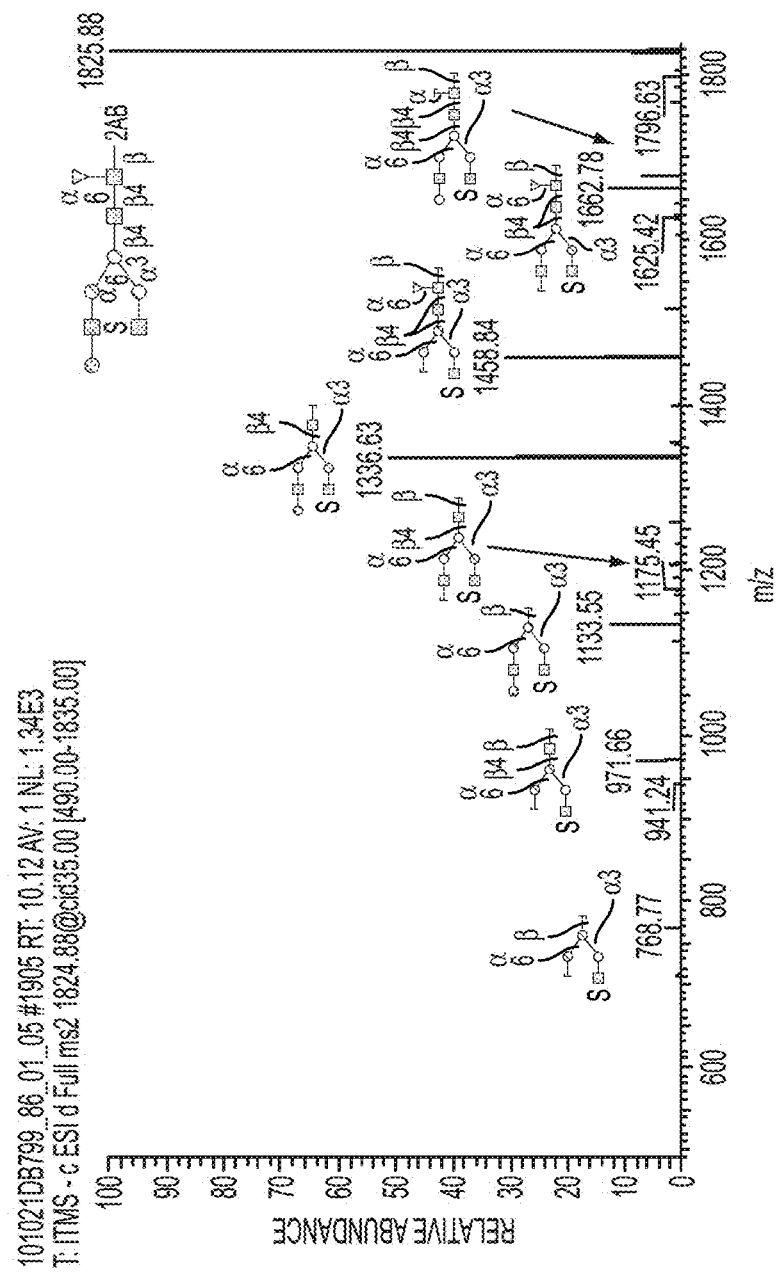
FIG. 8 is a representation of MS/MS analysis of mass species 1825 (4,4,1,0,0+SO$_3$). This mass correlates with G1F with a single sulfate. Fragmentation analysis by MS/MS suggests sulfation of a terminal GlcNAc residue.
Figure 9:
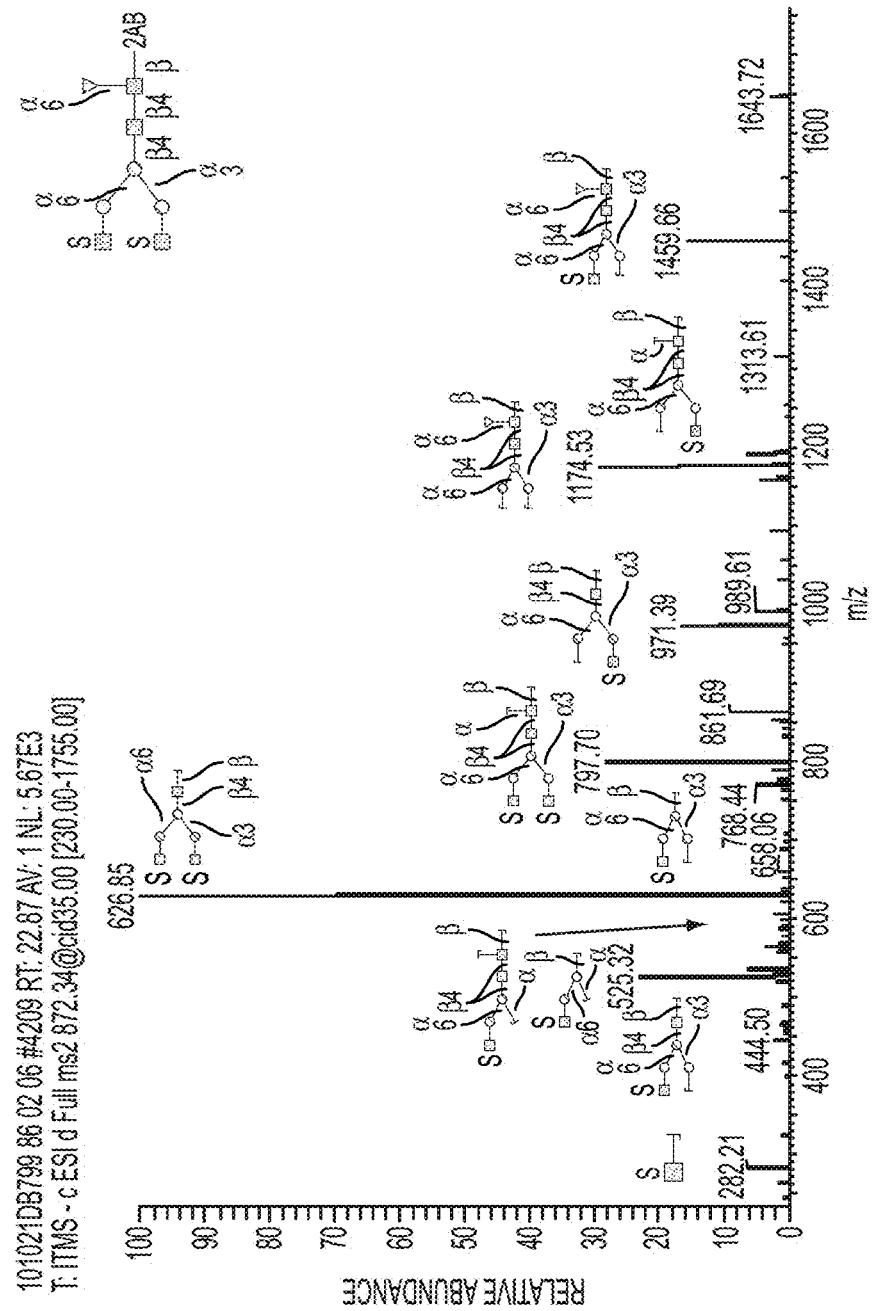
FIG. 9 is a representation of MS/MS analysis of mass species 1743 (4,3,1,0,0+2SO$_3$). This mass correlates with G0F with two sulfate groups. Fragmentation analysis by MS/MS suggests sulfation of a both terminal GlcNAc residues.

The sulfated species from the N-glycan mixture from Humira® were separated by charge-based HILIC-LC chromatography. In all sulfation reactions, there were two distinct charged regions that were absent in control reactions lacking sulfotransferase (FIGS. 6A-C). These regions corresponded to sulfated species. MS analysis identified the earlier eluting species as singly sulfated N-glycans (G0F or G1F with a single sulfate) and the later eluting as doubly sulfated N-glycans species (sulfation of both terminal GlcNAc residues) (FIGS. 7, 8, and 9). Unexpectedly, there were marked differences in the elution patterns between CHTS2, CHST5 and CHST7. These differences were likely result of the substrate preferences for each of the sulfotransferases.

Overall, CHST2 sulfation pattern showed one prominent peak in the region corresponding to the single sulfated species and a low level of doubly sulfated glycans (FIG. 6A). Conversely, CHST5 produced two relatively small peaks with comparable surface area of single sulfated species and one prominent peak of doubly sulfated species (FIG. 6B). When CHST2 and CHST5 were combined in one reaction, all peaks from the corresponding single enzyme reactions were accounted for, but their relative surface area was altered. Single sulfated species present in CHTS2 reaction were reduced, likely being converted to doubly sulfated by CHST5 (FIG. 6C). Two other singly sulfated species seemed to be resistant to the second sulfate transfer. These were possibly the isomers of sulfated G1F. CHST7 activity appeared to follow that of CHST2, but it was distinct from CHST5 (data not shown). CHST5 produced the highest fraction of sulfated N-glycans, (<85% total), mostly doubly sulfated (63%). By contrast, CHST2 sulfated <41% of total N-glycans, producing mostly singly sulfated species (around 34%). Overall level of sulfation for CHST2 and CHST5 when they worked together was comparable to that of CHST5 (82%) (Table 4).

TABLE 4

Total relative N-glycans sulfation [%] by CHST2 and CHST5

| Enzyme | Single sulfate | Double sulfate | Total sulfation |
|---|---|---|---|
| CHST2 | 33.8 | 7.6 | 41.4 |
| CHST5 | 23.3 | 63.4 | 86.7 |
| CHST2 + CHST5 | 27.2 | 54.8 | 82 |

Example 4—Production of Per-acetylated Sugar Sulfates

As described herein, glycoproteins can be sulfated by metabolic sulfation using sulfated sugars. The following describes the production of a per-acetylated sugar sulfate.

Step 1: 1, 6-O-Ditrityl-N-acetyl-D-glucosamine

N-acetyl-D-glucosamine (11 grams; 49.73 mmol) was dissolved in anhydrous pyridine (110 ml) with stirring. Trityl chloride (34.85 grams; 125 mmol) was added portion wise at room temperature. The solution was allowed to stir at room temperature for 20 hrs. The temperature was increased to 50° C. and allowed to stir for at least 24 hrs.

The progress of the reaction was monitored using silica thin layer chromatography (TLC). The TLC solvent used was chloroform:methanol (9:1, v/v). The 6-O-trityl-N-acetyl-D-glucosamine was observed after 20 hrs at room temperature, with the 1,6-O-ditrityl-N-acetyl-D-glucosamine formed at 50° C.

The reaction was cooled to room temperature and slowly poured into ice-water (1 liter) with stirring to quench trityl chloride present. The solution was allowed to warm to room temperature, and sit until the solution was clear. The solids were removed by filtration, washed with water and dissolved in chloroform. The chloroform solution was dried over anhydrous sodium sulfate and concentrated to dryness.

Purification was performed on a silica gel column using a gradient: chloroform:methanol (100:0→5:1). Yield was 17.73 grams; 25 mmol (50%).

Step 2: 1, 6-O-Ditrityl-N-acetyl-D-glucosamine 3(4)-sulfate, Calcium Salt 1,6-O-Ditrityl-N-acetyl-D-glucosamine (3530 mg; 5 mmol) was stirred in dimethylformamide at room temperature until all of the material was in solution. Pyridine-sulfur trioxide complex (1275 mg; 5 mmol) was added portion wise and the reaction stirred at room temperature overnight.

The progress of the reaction was monitored using silica thin layer chromatography (TLC). The TLC solvent used was chloroform:methanol (7.5:2.5, v/v). The 1,6-O-ditrityl-N-acetyl-D-glucosamine 3(4)-sulfate formed running slower than 1,6-O-ditrityl-N-acetyl-D-glucosamine.

The reaction was taken to dryness on a rotary evaporator with the water bath set at 35° C. Water (50 ml) was added and the solution neutralized to between pH 5.0 and pH 6.5 with calcium hydroxide. The solution was concentrated to about 10 ml on the rotary evaporator with the water bath set at 30° C. Water (50 ml) was again added and the solution neutralized to between 5.0 and pH 6.5 with calcium hydroxide. This process was continued until the solution remained constant between pH 5.0 and pH 6.5 with the addition of water. If the solution was greater than pH 7.0, dry ice was placed in the flask to neutralize the excess base.

The solution was taken to dryness a final time on the rotary evaporator. The residue was dissolved in chloroform (300 ml), washed with water (3×100 ml), and taken to dryness. The dough like material was dissolved in acetonitrile and checked by TLC silica gel (chloroform:methanol (7.5:2.5, v/v)) and HPLC-Single Quad Mass Spec analysis.

HPLC: Vydac C18 reverse phase column; Gradient: Water:acetonitrile (60:40→45:55). MS Single Quad: Theoretical masses 785.27 (100%), 786.27 (51.4%), 787.27 (14.7%); Observed 784.2 (100%), 785.2 (52%), 786.1 (15%).

Step 3: N-acetyl-D-glucosamine 3(4)-sulfate, Calcium Salt

The crude 1,6-O-Ditrityl-N-acetyl-D-glucosamine 3(4)-sulfate, calcium salt was dissolved in glacial acetic acid:water (9:1, v/v) (75 ml) and stirred overnight at room temperature. Sufficient solvent was used so that no cloudiness remained.

The progress of the reaction was monitored using silica thin layer chromatography (TLC). The TLC solvent used was chloroform:methanol:water (5:4:1, v/v/v). The N-acetyl-D-glucosamine 3(4)-sulfate product ran near the origin with the 1,6-O-ditrityl-N-acetyl-D-glucosamine 3(4)-sulfate precursor material running near the solvent front.

The solution was concentrated to dryness and the material taken up in water (25 ml). The trityl alcohol was filtered off and washed with water. The filtrate was taken to dryness, azeotroped with water and desiccated.

Step 4: 1,3(4), 6-tri-O-acetyl-N-acetyl-D-glucosamine 3(4)-sulfate, Calcium Salt The N-acetyl-D-glucosamine 3(4)-sulfate (Step 3) was dissolved in acetonitrile (50 ml), with 25 ml taken for per-acetylation. The 25 ml aliquot was taken to dryness and the material taken up in acetic anhydride (50 ml). Triethylamine (2.5 ml) was added and the solution stirred until the solution became yellow. The solution was slowly poured into ice water (500 ml) and stirred until the solution was at room temperature and everything was in solution.

The progress of the reaction was monitored using silica thin layer chromatography (TLC). The TLC solvents used were chloroform:methanol (7.5:2.5, v/v) and ethyl acetate:methanol:water (6:2:1). A preliminary purification was accomplished by passing the material through a silica gel column (100 ml) with ethyl acetate:methanol:water (6:2:1) and 30 ml fractions collected. The fractions containing 1,3(4),6-tri-O-acetyl-N-acetyl-D-glucosamine 3(4)-sulfate were combined and water (20 ml) added. The solution was reduced to about 25 ml and a suspension of calcium carbonate in water added until the solution was between pH 5.5 and pH 6.5. The solution was filtered and concentrated.

Purification was accomplished using an HPLC: Vydac C18 reverse phase column; Gradient: Water:acetonitrile (100:0→90:10).

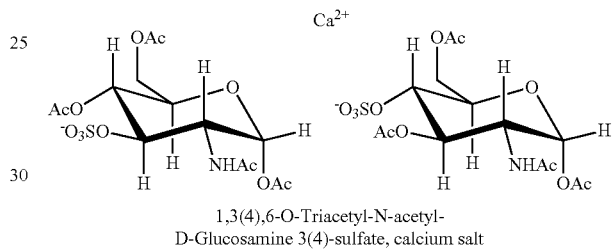

1,3(4),6-O-Triacetyl-N-acetyl-D-Glucosamine 3(4)-sulfate, calcium salt

Example 5—Generation of Mutant Antibodies

Various double mutants were made by synthesizing the heavy chain gene of rituximab, using its nucleotide sequence that was first codon-optimized using DNA2.0. The amino acids to be mutated were picked based on their molecular interactions found in the crystal structures for Fc dimers with glycans bound to Fc-gamma receptor III (Mizushima et al., Genes to Cells 16:1071-1080 (2011), and Ferrara et al., PNAS 108:12669-12674 (2011)). The antibody heavy chain genes were expressed using the CMV promoter in either HEK293 or CHO-S cells along with the synthesized gene for the light chain expressed from a separate plasmid. The antibodies were transiently expressed from the two plasmids and purified by protein G chromatography. The amino acid sequences of wild type rituximab heavy chain and mutants 1, 2, 3, and 4 are depicted in Table 5 (SEQ ID NOs: 1-5; modified amino acid residues are in bold and underlined).

TABLE 5

Amino acid sequences of WT rituximab and mutants

WT rituximab (SEQ ID NO: 1)

MGWSLILLFLVAVATRVLSQVQLQQPGAELVKPGASVKMSCKASGYTFTS

YNMHWVKQTPGRGLEWIGAIYPGNGDTSYNQKFKGKATLTADKSSSTAYM

QLSSLTSEDSAVYYCARSTYYGGDWYFNVWGAGTTVTVSAASTKGPSVFP

LAPSSKSTSGGTAALGCLVKDYFPEPVTVSWNSGALTSGVHTFPAVLQSS

GLYSLSSVVTVPSSSLGTQTYICNVNHKPSNTKVDKKAEPKSCDKTHTCP

TABLE 5-continued

Amino acid sequences of WT rituximab and mutants

PCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKA

LPAPIEKTISKAKGQPREPQVYTLPPSRDELTKNQVSLTCLVKGFYPSDI

AVEWESNGQPENNYKTTPPVLDSDGSFFLYSKLTVDKSRWQQGNVFSCSV

MHEALHNHYTQKSLSLSPGK

Mutant 1 - F241A, F243A (SEQ ID NO: 2)

MGWSLILLFLVAVATRVLSQVQLQQPGAELVKPGASVKMSCKASGYTFTS

YNMHWVKQTPGRGLEWIGAIYPGNGDTSYNQKFKGKATLTADKSSSTAYM

QLSSLTSEDSAVYYCARSTYYGGDWYFNVWGAGTTVTVSAASTKGPSVFP

LAPSSKSTSGGTAALGCLVKDYFPEPVTVSWNSGALTSGVHTFPAVLQSS

GLYSLSSVVTVPSSSLGTQTYICNVNHKPSNTKVDKKAEPKSCDKTHTCP

PCPAPELLGGPSVALAPPKPKDTLMISRTPEVTCVVVDVSHEDPEVKFNW

YVDGVEVHNAKTKPREEQYNSTYRVVSVLTVLHQDWLNGKEYKCKVSNKA

LPAPIEKTISKAKGQPREPQVYTLPPSRDELTKNQVSLTCLVKGFYPSDI

AVEWESNGQPENNYKTTPPVLDSDGSFFLYSKLTVDKSRWQQGNVFSCSV

MHEALHNHYTQKSLSLSPGK

Mutant 2 - F243A, R301A (SEQ ID NO: 3)

MGWSLILLFLVAVATRVLSQVQLQQPGAELVKPGASVKMSCKASGYTFTS

YNMHWVKQTPGRGLEWIGAIYPGNGDTSYNQKFKGKATLTADKSSSTAYM

QLSSLTSEDSAVYYCARSTYYGGDWYFNVWGAGTTVTVSAASTKGPSVFP

LAPSSKSTSGGTAALGCLVKDYFPEPVTVSWNSGALTSGVHTFPAVLQSS

GLYSLSSVVTVPSSSLGTQTYICNVNHKPSNTKVDKKAEPKSCDKTHTCP

PCPAPELLGGPSVFLAPPKPKDTLMISRTPEVTCVVVDVSHEDPEVKFNW

YVDGVEVHNAKTKPREEQYNSTYAVVSVLTVLHQDWLNGKEYKCKVSNKA

LPAPIEKTISKAKGQPREPQVYTLPPSRDELTKNQVSLTCLVKGFYPSDI

AVEWESNGQPENNYKTTPPVLDSDGSFFLYSKLTVDKSRWQQGNVFSCSV

MHEALHNHYTQKSLSLSPGK

Mutant 3 - K246A, T260A (SEQ ID NO: 4)

MGWSLILLFLVAVATRVLSQVQLQQPGAELVKPGASVKMSCKASGYTFTS

YNMHWVKQTPGRGLEWIGAIYPGNGDTSYNQKFKGKATLTADKSSSTAYM

QLSSLTSEDSAVYYCARSTYYGGDWYFNVWGAGTTVTVSAASTKGPSVFP

LAPSSKSTSGGTAALGCLVKDYFPEPVTVSWNSGALTSGVHTFPAVLQSS

GLYSLSSVVTVPSSSLGTQTYICNVNHKPSNTKVDKKAEPKSCDKTHTCP

PCPAPELLGGPSVFLPPPAPKDTLMISRTPEVACVVVDVSHEDPEVKFNW

YVDGVEVHNAKTKPREEQYNSTYRVVSVLTVLHQDWLNGKEYKCKVSNKA

LPAPIEKTISKAKGQPREPQVYTLPPSRDELTKNQVSLTCLVKGFYPSDI

AVEWESNGQPENNYKTTPPVLDSDGSFFLYSKLTVDKSRWQQGNVFSCSV

MHEALHNHYTQKSLSLSPGK

TABLE 5-continued

Amino acid sequences of WT rituximab and mutants

Mutant 4 - T260A, R301A (SEQ ID NO: 5)

MGWSLILLFLVAVATRVLSQVQLQQPGAELVKPGASVKMSCKASGYTFTS

YNMHWVKQTPGRGLEWIGAIYPGNGDTSYNQKFKGKATLTADKSSSTAYM

QLSSLTSEDSAVYYCARSTYYGGDWYFNVWGAGTTVTVSAASTKGPSVFP

LAPSSKSTSGGTAALGCLVKDYFPEPVTVSWNSGALTSGVHTFPAVLQSS

GLYSLSSVVTVPSSSLGTQTYICNVNHKPSNTKVDKKAEPKSCDKTHTCP

PCPAPELLGGPSVFLFPPKPKDTLMISRTPEVACVVVDVSHEDPEVKFNW

YVDGVEVHNAKTKPREEQYNSTYAVVSVLTVLHQDWLNGKEYKCKVSNKA

LPAPIEKTISKAKGQPREPQVYTLPPSRDELTKNQVSLTCLVKGFYPSDI

AVEWESNGQPENNYKTTPPVLDSDGSFFLYSKLTVDKSRWQQGNVFSCSV

MHEALHNHYTQKSLSLSPGK

Figure 10:
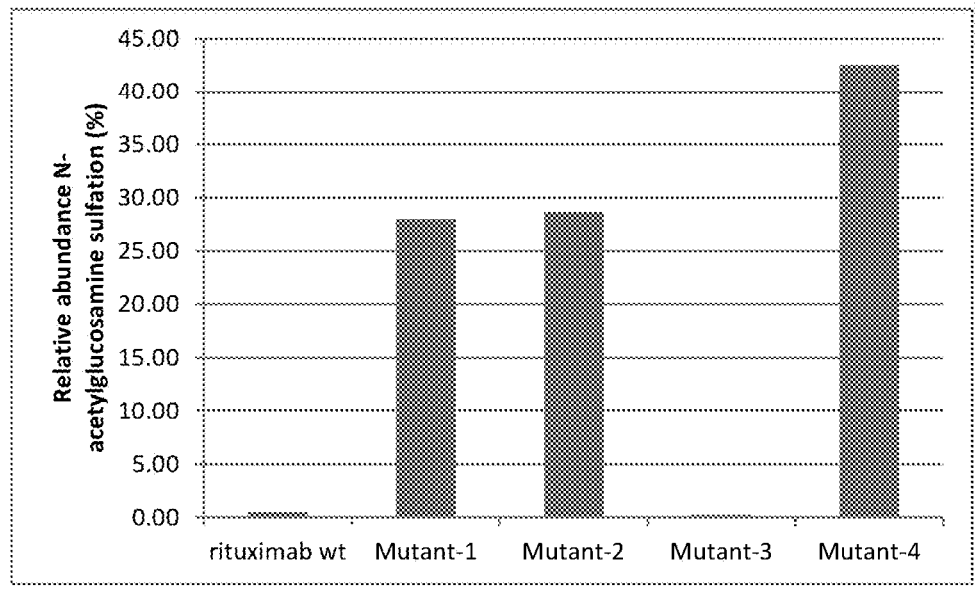
FIG. 10 is a diagrammatic representation of total sulfation of wild type (under chemical denaturation conditions) and mutant rituximab IgG1 antibodies.
Figure 11A:
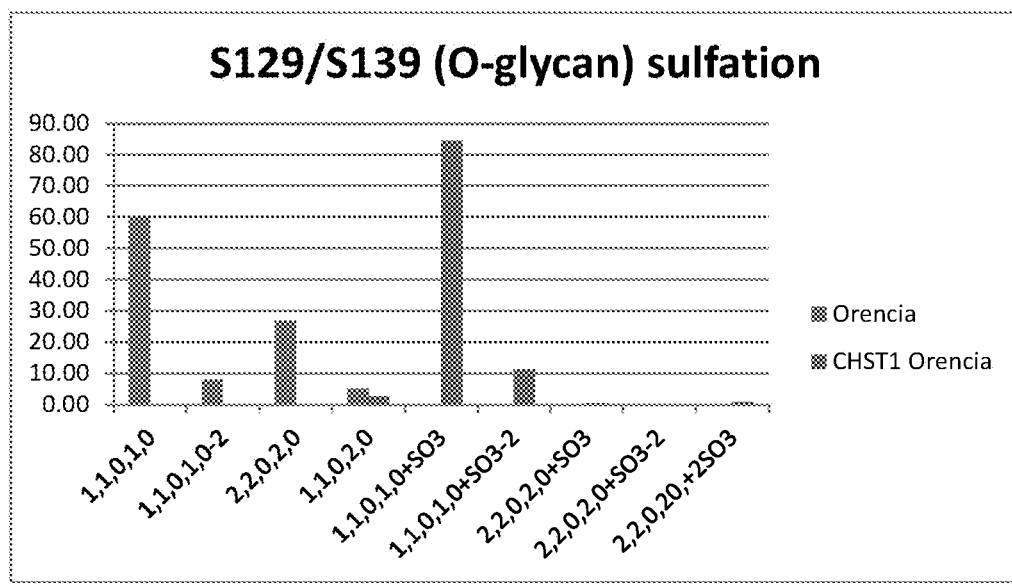
FIG. 11A is a diagrammatic representation of sulfation of Orencia® O-glycans by CHST1. (Naming convention is in the order N-acetylhexosamine, hexose, deoxyhexose, N-acetylneuraminic acid, and N-glycylneuraminic acid. For example, a designation of "1,1,0,1,0" means one N-acetylhexosamine, one hexose, no deoxyhexose, one N-acetylneuraminic acid, and no N-glycoylneuraminic acid.)
Figure 11B:
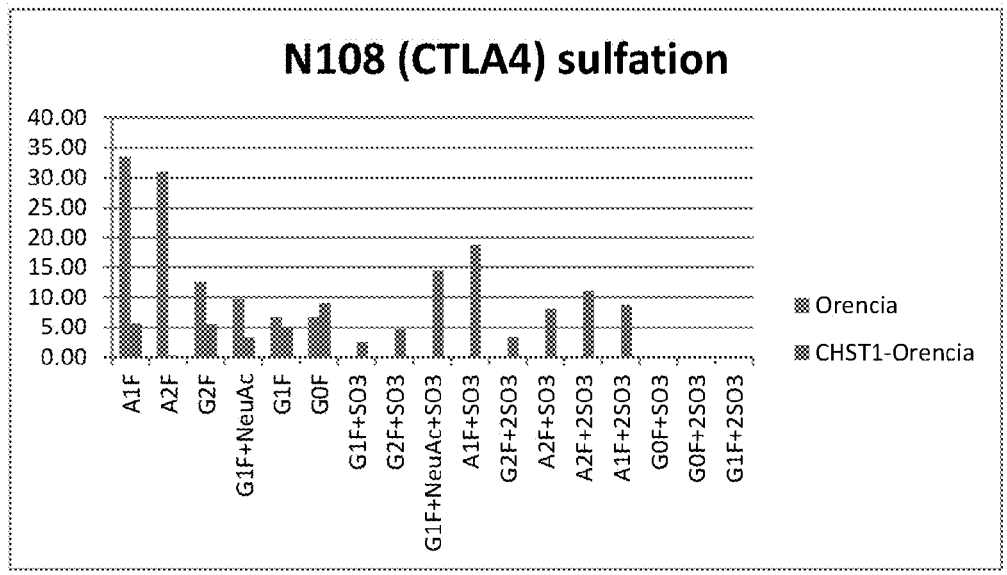
FIG. 11B is a diagrammatic representation of sulfation of Orencia® N-glycans on asparagine 108 by CHST1.
Figure 11C:
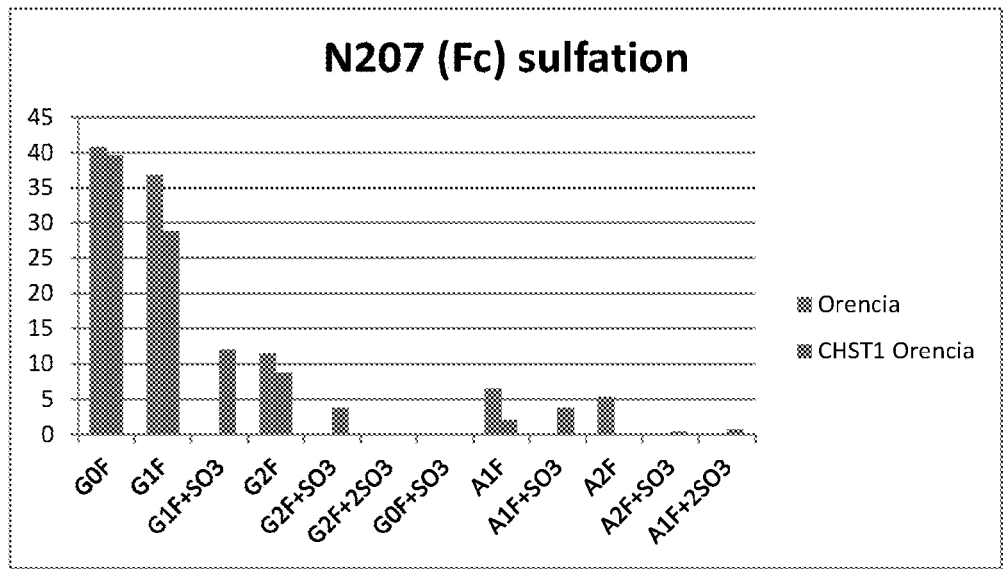
FIG. 11C is a diagrammatic representation of sulfation of Orencia® N-glycans on asparagine 207 with CHST1.
Figure 11D:
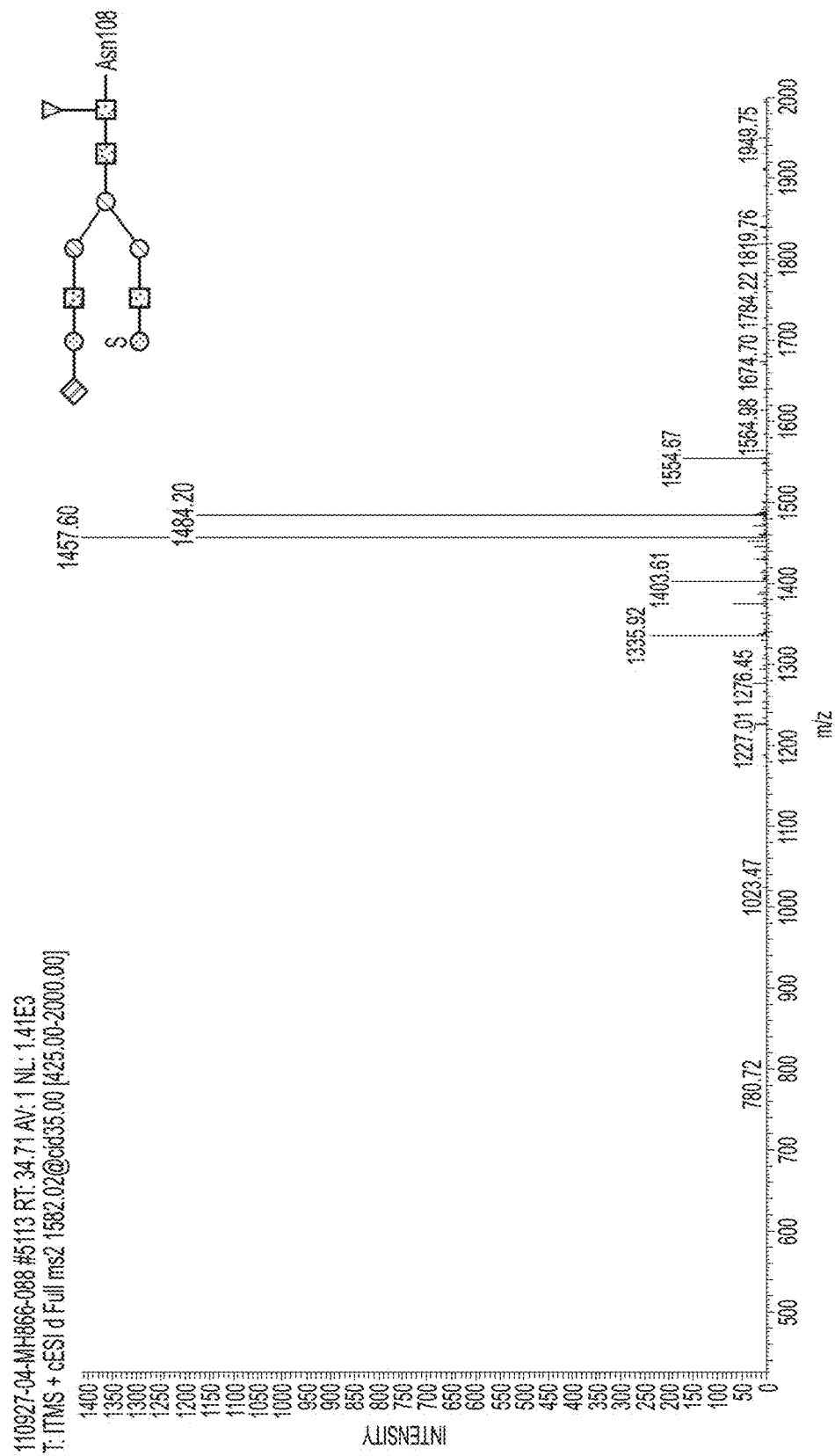
FIG. 11D is a representation of MS/MS analysis of asparagine 108 sulfated A1F glycopeptides.

Example 6—Characterization of Antibody Mutations on "Post Production" Glycosylation Certain modifications of N-glycans in the Fc domain of an IgG1 molecule can be confounded by protein conformation. For example, the ability to sulfate an antibody can be affected by protein conformation. Disrupting the conformation of purified (post-production) wild type rituximab with increasing concentrations of a chemical denaturant (urea), followed by in vitro treatment with a sulfo-transferase, resulted in increasing levels of total sulfation of the antibody glycans. Introducing mutations into the Fc region also resulted in increased levels of sulfation in the presence of a sulfo-transferase in vitro. As shown in FIG. 10, mutants 1, 2, and 4 (but not mutant 3) exhibited increased levels of sulfation (in the absence of urea) compared to that of wild type rituximab (not treated with urea).

Example 7—Down-Regulation of Inflammatory Cell Infiltration Using a Sulfated Version of Abatacept (Orencia®)

The effects of a sulfated version of Orencia® on inflammatory responses associated with arthritis were investigated using a DBA/1 mouse model of collagen antibody-induced arthritis.

Methods

A model Fc-fusion protein, Orencia® (Bristol-Myers Squibb) was sulfated in vitro using CHST1 under the following reaction conditions. Briefly, Orencia® was incubated with purified CHST1 enzyme at an enzyme to substrate ratio of 1:20 (w:w), in the presence of 50 mM MES, pH 6.7, and 5 mM PAPS at 37° C. overnight with gentle rotation. After sulfation, the protein was affinity purified by Protein A.

Relative quantitation of Orencia® sulfation was performed in a site-specific manner at the glycopeptide level. The relative quantities were based on the extracted ion area from positive mode LC-MS analysis for the most abundant charge state for each of the sites of N-glycosylation and O-glycosylation of chymotryptic digests of Orencia®.

A mouse model of collagen induced arthritis was employed. Eight groups of DBA/1 mice (14 mice in each group) were administered an intravenous solution of 5 specific clones of mouse anti-type II collagen antibody (1.5 mg/dose) on day 0. On day 3, mice were administered i.p. a solution of 25 µg lipopolysaccharides (LPS). The vehicle control group did not receive further treatment after day 0.

A mouse model of collagen induced arthritis was employed. Eight groups of DBA/1 mice (14 mice in each group) were administered an intravenous solution of 5 specific clones of mouse anti-type II collagen antibody (1.5 mg/dose) on day 0. On day 3, mice were administered i.p. a solution of 25 µg lipopolysaccharides (LPS). The vehicle control group did not receive further treatment after day 0. Model Fc fusion protein Orencia® (2.5 or 10 mg/kg) or sulfated Orencia® (2.5 or 10 mg/kg) were administered i.p. on days 0, 2, 4, 6, 8, 10, 12 and 18. Prednisolone (1.0 mg/kg) was administered orally and daily from days 0 to 19. Animals were weighed and paw thickness measured each day, and arthritis severity was scored using a 5 point scale. On day 19, all the animals were sacrificed and paws and joints were collected. The paws were digested with Liberase™ and DNAse, and the isolated cells were washed and stained with a cocktail of antibodies containing Ly6G-FITC, Ly6C-PE, F4/80-PerCP, CD19-PE-Cy, Sca1-APC, and CD3-APC-Cγ7. The samples were fixed with 2% paraformaldehyde and acquired by flow cytometry and then analyzed using FlowJo software.

Results

The sulfation patterns of O-linked and N-linked glycans of sulfated Orencia® were analyzed by LC-MS. As shown in FIGS. 11A-11D, CHST1 sulfated galactose residues on N-linked and O-linked glycans of Orencia®.

Figure 12A:
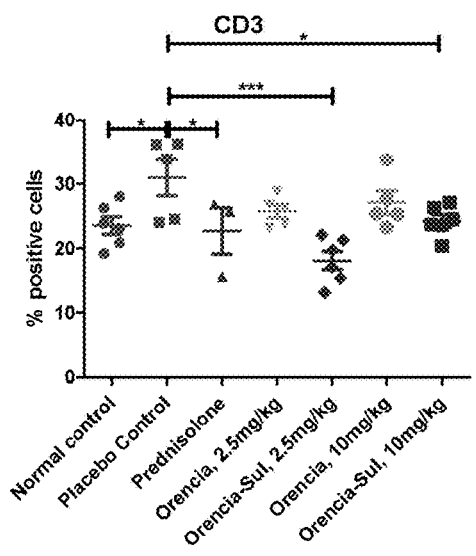
FIG. 12A is a diagrammatic representation of CD3+ cells in normal mice (not treated with collagen antibody), or antibody-induced arthritis mice treated with placebo, prednisolone, Orencia®, or sulfated Orencia®.
Figure 12B:
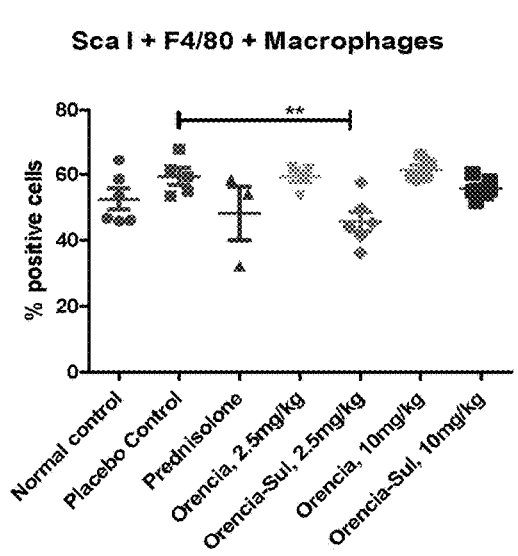
FIG. 12B is a diagrammatic representation of Sca I+ cells in normal mice (not treated with collagen antibody), or antibody-induced arthritis mice treated with placebo, prednisolone, Orencia®, or sulfated Orencia®.
Figure 12C:
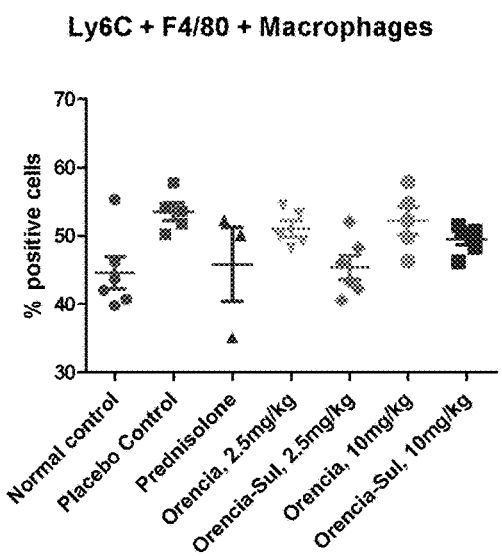
FIG. 12C is a diagrammatic representation of Ly6C+ cells in normal mice (not treated with collagen antibody), or antibody-induced arthritis mice treated with placebo, prednisolone, Orencia®, or sulfated Orencia®.

The levels of various immune cells in the joints of control and treated mice were determined by FACS analysis (FIGS. 12A-12C). Joints from mice treated with anti-type II collagen antibody and LPS to induce arthritis contained, on average, 31% of CD3+ cells, 59% of Sca I positive macrophages, and 54% of Ly6C positive cells (of the total cell population). Joints from arthritis-induced mice that received 2.5 mg/kg sulfated Orencia® exhibited an average of 18% CD3+ cells, a significant decrease from the level of CD3+ cells in control mice. Further, 2.5 mg/kg sulfated Orencia® resulted in a decreased level of CD3+ cells compared to mice that received 2.5 mg/kg Orencia® (average of 26% CD3+ cells). Joints from arthritis-induced mice that received 2.5 mg/kg sulfated Orencia® exhibited a significant decrease in the level of Sca I positive macrophages (average of 46%), relative to control levels. 2.5 mg/kg sulfated Orencia® also resulted in a decreased level of Sca I positive macrophages compared to mice that received 2.5 mg/kg Orencia® (average of 59%). Finally, although neither sulfated nor unsulfated Orencia® at the doses tested resulted in Ly6C positive inflammatory macrophage levels that were significantly different from control, 2.5 mg/kg and 10 mg/kg sulfated Orencia® resulted in Ly6C positive inflammatory macrophage levels (average of 45% and 49%, respectively) that were lower compared to 2.5 mg/kg and 10 mg/kg Orencia® (average of 49% and 52%, respectively).

This example demonstrates that sulfated Orencia® decreased the infiltration of T-lymphocytes and Sca-I positive inflammatory macrophages into arthritic joints and paws of an arthritic DBA/1 mouse model, relative to unsulfated Orencia®. Thus, therapeutic proteins can be sulfated to modulate anti-inflammatory properties of therapeutic proteins.

All mouse groups exhibited symptoms of disease, including increased arthritis scores and paw thickness, body weight loss, and also some mortality. The group that received prednisolone had significantly lower arthritis scores compared to the control group. None of the groups receiving Orencia, either sulfated or non-sulfated, showed significant suppression of mean arthritis score or mean paw thickness score as compared to PBS negative control in this experiment, suggesting that these scores are not good proxies for differences in activities observed at the cellular level.

EQUIVALENTS

It is to be understood that while the disclosure has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A preparation of abatacept, wherein at least 5% of the abatacept of the preparation comprises an Fc region comprising a sulfated glycan.

2. The preparation of claim 1, wherein the sulfated glycan is linked to a CH2 domain of an IgG heavy chain.

3. The preparation of claim 2, wherein the sulfated glycan is linked to Asn297 of the IgG heavy chain.

4. The preparation of claim 1, wherein the sulfated glycan comprises a branched glycan.

5. The preparation of claim 2, wherein the sulfated glycan comprises one or more of a sulfated N-acetylglucosamine, a sulfated galactose, or a sulfated N-acetylgalactosamine.

6. The preparation of claim 1, wherein at least 10% of the abatacept of the preparation comprises an Fc region comprising a sulfated glycan.

7. The preparation of claim 1, wherein the glycan is singly sulfated.

8. The preparation of claim 1, wherein the glycan is doubly sulfated.

9. The preparation of claim 1, wherein the abatacept comprising an Fc region comprising a sulfated glycan has a different Fc receptor affinity, Fc receptor specificity, complement activation activity, signaling activity, targeting activity, effector function, half-life, clearance, pro-inflammatory activity, anti-inflammatory activity, or transcytosis activity than a corresponding abatacept comprising an Fc region that does not comprise a sulfated Fc glycan.

10. The preparation of claim 9, wherein the effector function is antibody dependent cellular cytotoxicity, complement dependent cytotoxicity, programmed cell death, or cellular phagocytosis.

11. The preparation of claim 9, wherein the Fc receptor is an FcγRI, FcγRIIA, FcγRIIB, FcγRIIIA, FcγRIIIB, FcγRIV, or FcRn receptor.

12. The preparation of claim 11, wherein the abatacept comprising an Fc region comprising a sulfated glycan binds to a macrophage, neutrophil, dendritic cell, B cell, natural killer cell, or eosinophil.

13. A method of modifying activity of a preparation of abatacept, the method comprising:
   providing a preparation of abatacept comprising an immunoglobulin Fc region comprising a glycan; and
   sulfating the glycan of at least 5% of the abatacept of the preparation,
   the abatacept comprising the sulfated glycan having a different Fc receptor affinity, Fc receptor specificity, complement activation activity, signaling activity, targeting activity, effector function, half-life, clearance, pro-inflammatory activity, anti-inflammatory activity, or transcytosis activity than a corresponding abatacept that does not comprise a sulfated glycan.

* * * * *